US010633692B2

(12) United States Patent
Iyidogan et al.

(10) Patent No.: US 10,633,692 B2
(45) Date of Patent: Apr. 28, 2020

(54) SEQUENCING METHOD EMPLOYING TERNARY COMPLEX DESTABILIZATION TO IDENTIFY COGNATE NUCLEOTIDES

(71) Applicant: Omniome, Inc., San Diego, CA (US)

(72) Inventors: Pinar Iyidogan, San Diego, CA (US); Kandaswamy Vijayan, San Diego, CA (US)

(73) Assignee: OMNIOME, INC., San Diego, CA (US)

(*) Notice: Subject to any disclaimer, the term of this patent is extended or adjusted under 35 U.S.C. 154(b) by 0 days.

(21) Appl. No.: 16/372,812

(22) Filed: Apr. 2, 2019

(65) Prior Publication Data

US 2019/0226012 A1 Jul. 25, 2019

Related U.S. Application Data

(63) Continuation of application No. 15/581,828, filed on Apr. 28, 2017, now Pat. No. 10,294,514.

(60) Provisional application No. 62/329,933, filed on Apr. 29, 2016, provisional application No. 62/487,586, filed on Apr. 20, 2017.

(51) Int. Cl.
C12P 19/34 (2006.01)
C12Q 1/6809 (2018.01)
C12Q 1/6874 (2018.01)
C12Q 1/6816 (2018.01)
C12Q 1/6848 (2018.01)
C12Q 1/6869 (2018.01)

(52) U.S. Cl.
CPC ......... C12Q 1/6809 (2013.01); C12Q 1/6816 (2013.01); C12Q 1/6848 (2013.01); C12Q 1/6869 (2013.01); C12Q 1/6874 (2013.01)

(58) Field of Classification Search
CPC ........ C12Q 2521/101; C12Q 2527/125; C12Q 2527/137; C12Q 2535/101; C12Q 2535/125; C12Q 2565/518; C12Q 2565/607; C12Q 1/6869; C12Q 1/68; C12Q 1/6816; C12Q 1/6848
See application file for complete search history.

(56) References Cited

U.S. PATENT DOCUMENTS 5,302,509 A   4/1994   Cheeseman
5,614,365 A   3/1997   Tabor et al.
6,485,909 B1  11/2002  Hong et al.
6,720,177 B2  4/2004   Ghadiri et al.
6,828,094 B2  12/2004  Kilger et al.
6,908,736 B1  6/2005   Densham
7,008,766 B1  3/2006   Densham
7,057,026 B2  6/2006   Barnes et al.
7,223,540 B2  5/2007   Pourmand et al.
7,264,934 B2  9/2007   Fuller
7,329,492 B2  2/2008   Hardin et al.
7,414,116 B2  8/2008   Milton et al.
7,427,673 B2  9/2008   Balasubramanian et al.
7,449,297 B2  11/2008  Freije et al.
7,482,120 B2  1/2009   Buzby
7,544,794 B1  6/2009   Benner et al.
7,604,963 B2  10/2009  Densham
7,635,578 B2  12/2009  Ju et al.
7,713,698 B2  5/2010   Ju et al.
7,790,869 B2  9/2010   Ju et al.
7,871,771 B2  1/2011   Fuller et al.
7,939,264 B1  5/2011   Densham
7,956,171 B2  6/2011   Siddiqi et al.
8,034,923 B1  10/2011  Benner et al.
8,071,755 B2  12/2011  Efcavitch et al.
8,088,575 B2  1/2012   Ju et al.
8,133,672 B2  3/2012   Bjornson et al.
8,236,532 B2  8/2012   Ronaghi et al.
8,298,792 B2  10/2012  Ju et al.
8,399,196 B2  3/2013   Hoser
8,481,266 B2  7/2013   Shao et al.
8,535,881 B2  9/2013   Schneider
8,603,741 B2  12/2013  Emig et al.
8,632,975 B2  1/2014   Vander Horn et al.
8,658,365 B2  2/2014   Bjornson et al.
8,703,461 B2  4/2014   Peris et al.
8,808,989 B1  8/2014   Siddiqi et al.
8,911,972 B2  12/2014  Chaisson et al.
8,986,930 B2  3/2015   Fedorov et al.

(Continued)

FOREIGN PATENT DOCUMENTS

EP   1115848      7/2001
WO   1990/013666  11/1990

(Continued)

OTHER PUBLICATIONS

"APCH231: Chemical Analysis Complexometric Titrations EDTA", Notes compiled by Dr. C. Southway, Available Online At: (http://cheminnerweb.ukzn.ac.za/libraries/apch231_h_govender_s_notes/apch231_edta.sflb.ashx)., pp. 30-42.

"International Search Report and Written Opinion", PCT Application No. PCT/US2017/067976, dated Mar. 14, 2018, 13 pages.

U.S. Appl. No. 15/581,828, "Corrected Notice of Allowability", dated Mar. 28, 2019, 4 pages.

U.S. Appl. No. 15/581,828, "Notice of Allowance", dated Feb. 28, 2019, 10 pages.

Agnarsson et al., "On-Chip Modulation of Evanescent Illumination and Live-Cell Imaging With Polymer Waveguides.", Optics Express, vol. 19, Issue No. 23, Nov. 7, 2011, pp. 22929-22935.

(Continued)

Primary Examiner — Cynthia B Wilder
(74) Attorney, Agent, or Firm — Kilpatrick Townsend & Stockton LLP

(57) ABSTRACT

Provided are methods and systems for detecting formation of nucleotide-specific ternary complexes comprising a DNA polymerase, a nucleic acid, and a nucleotide complementary to the templated base of the primed template nucleic acid. The methods and systems facilitate determination of the next correct nucleotide without requiring chemical incorporation of the nucleotide into the primer. These results can even be achieved in procedures employing unlabeled, native nucleotides.

16 Claims, 6 Drawing Sheets

(56) References Cited

U.S. PATENT DOCUMENTS

| | | | |
|---|---|---|---|
| 9,255,258 | B2 | 2/2016 | Vander Horn et al. |
| 9,279,155 | B2 | 3/2016 | Bjornson et al. |
| 9,279,154 | B2 | 6/2016 | Previte et al. |
| 9,399,798 | B2 | 7/2016 | Morris et al. |
| 2006/0051807 | A1 | 3/2006 | Fuller |
| 2006/0292583 | A1 | 12/2006 | Schneider et al. |
| 2007/0009925 | A1 | 1/2007 | Fang et al. |
| 2009/0061447 | A1 | 3/2009 | Schneider |
| 2010/0316999 | A1 | 12/2010 | Densham |
| 2010/0317012 | A1 | 12/2010 | Ju et al. |
| 2011/0008794 | A1 | 1/2011 | Schneider |
| 2011/0160077 | A1 | 6/2011 | Chaisson et al. |
| 2011/0237464 | A1 | 9/2011 | Cunningham et al. |
| 2013/0165328 | A1 | 6/2013 | Previte et al. |
| 2014/0127680 | A1 | 5/2014 | Emig et al. |
| 2014/0234940 | A1 | 8/2014 | Peris et al. |
| 2016/0010150 | A1 | 1/2016 | Emig et al. |
| 2016/0168633 | A1 | 6/2016 | Previte et al. |
| 2016/0177384 | A1 | 6/2016 | Bjornson et al. |
| 2016/0208318 | A1 | 7/2016 | Vander Horn et al. |
| 2017/0022553 | A1 | 1/2017 | Vijayan et al. |
| 2017/0292157 | A1 | 10/2017 | Drmanac |
| 2017/0314064 | A1 | 11/2017 | Iyidogan et al. |

FOREIGN PATENT DOCUMENTS

| | | |
|---|---|---|
| WO | 9106678 | 5/1991 |
| WO | 9506138 | 3/1995 |
| WO | 2001/016375 | 5/2001 |
| WO | 2002/04680 | 1/2002 |
| WO | 2005/121363 | 12/2005 |
| WO | 2007048033 | 4/2007 |
| WO | 2007123744 | 11/2007 |
| WO | 2009061911 | 5/2009 |
| WO | 2009145820 | 12/2009 |
| WO | 2010/068884 | 6/2010 |
| WO | 2010/111690 | 9/2010 |
| WO | 2010141390 | 12/2010 |
| WO | 2011/159942 | 12/2011 |
| WO | 2012/166742 | 12/2012 |
| WO | 2013/096692 | 6/2013 |
| WO | 2014114665 | 6/2014 |
| WO | 2016071689 | 5/2016 |
| WO | 2017014762 | 1/2017 |
| WO | 2017117235 | 7/2017 |
| WO | 2017184996 | 10/2017 |
| WO | 2018034780 | 2/2018 |

OTHER PUBLICATIONS

Anker et al., "Biosensing with Plasmonic Nanosensors", Nature Materials, vol. 7, Issue No. 6, Jun. 2008, pp. 442-453.

Bandwar et al., "Peculiar 2-Aminopurine Fluorescence Monitors the Dynamics of Open Complex Formation by Bacteriophage T7 RNA Polymerase", The Journal of Biological Chemistry, vol. 275, Issue No. 17, 2001, pp. 14075-14082.

Brockman et al., "A Multistep Chemical Modification Procedure to Create DNA Arrays on Gold Surfaces for the Study of Protein—DNA Interactions with Surface Plasmon Resonance Imaging", Journal of the American Chemical Society, vol. 121, 1999, pp. 8044-8051.

Brown et al., "Pre-Steady-State Kinetic Analysis of Truncated and Full-Length *Saccharomyces cerevisiae* DNA Polymerase Eta", Journal of Nucleic Acids, vol. 2010, Article ID 871939, 2010, 11 pages.

Campagnola et al., "High-Throughput Screening Identification of Poliovirus RNA-Dependent RNA Polymerase Inhibitors", Antiviral Res., vol. 91, Issue 3, Sep. 2011, pp. 241-251.

Chan et al., "A General Method for Discovering Inhibitors of Protein-DNA Interactions Using Photonic Crystal Biosensors", ACS Chem Biol, vol. 3, Issue 7, Jul. 18, 2008, pp. 437-448.

Chen et al., "The History and Advances of Reversible Terminators Used in New Generations of Sequencing Technology", Genomics Proteomics Bioinformatics, vol. 11, Issue 1, Feb. 1, 2013, pp. 34-40.

Chin et al., "The Effect of Divalent Nickel (Ni2+) on in Vivo DNA Replication by DNA Polymerase α1", Cancer Research, vol. 54, May 1, 1994, pp. 2337-2341.

Choi et al., "EML4-ALK Mutations in Lung Cancer that Confer Resistance to ALK Inhibitors", The New England Journal of Medicine, vol. 18, Oct. 28, 2010, pp. 1734-1739.

Concepcion et al., "Label-Free Detection of Biomolecular Interactions Using BioLayer Interferometry for Kinetic Characterization", Combinatorial Chemistry and High Throughput Screening, vol. 12, Issue 8, 2009, pp. 791-800.

Crumpacker, "Mechanism of Action of Foscarnet Against Viral Polymerase", American Journal of Medicine, vol. 92, Issue 2, Supplement 2A, Feb. 14, 1992, pp. 2A-3S-2A-7S.

Datta et al., "Salt Dependence of DNA binding by Thermus Aquaticus and *Escherichia coli* DNA Polymerases", Journal of Biological Chemistry, vol. 278, Issue No. 8, Feb. 21, 2003, pp. 5694-5701.

Deredge et al., "The Glutamate Effect on DNA Binding by Pol I DNA Polymerases: Osmotic Stress and the Effective Reversal of Salt Linkage", J. Mol. Biol., vol. 401, 2010, pp. 223-238.

Doublie et al., "An Open and Closed Case for All Polymerases", Structure, vol. 7, Issue 2, Feb. 1999, pp. R31-R35.

Dunlap et al., "Use of 2-Aminopurine and Tryptophan Fluorescence as Probes in Kinetic Analyses of DNA Polymerase Beta", Biochemistry, vol. 41, 2002, pp. 11226-11235.

Dzantiev et al., "A Conformational Change in *E. coli* DNA Polymerase I (Klenow Fragment) Is Induced in the Presence of a dNTP Complementary to the Template Base in the Active Site", Biochemistry, vol. 39, Issue 2, 2000, pp. 356-361.

Engtrom et al., "A Label-Free Continuous Total-Internal-Reflection-Fluorescence-Based Immunosensor", Analytical Biochemistry, 2006, pp. 1-8.

Eriksson et al., "Pyrophosphate Analogues as Inhibitors of DNA Polymerases of Cytomegalovirus, Herpes Simplex Virus and Cellular Origin", Biochimica et Biophysica Acta, vol. 696, Issue 2, 1982, pp. 115-123.

Escobedo et al., "Integrated Nanohole Array Surface Plasmon Resonance Sensing Device Using a Dual-Wavelength Source", Journal of Micromechanics and Microengineering, vol. 21, Issue No. 11, 2011, pp. 1-6.

Espinoza-Herrera et al., "Following DNA Chain Extension and Protein Conformational Changes in Crystals of a Y-Family DNA Polymerase via Raman Crystallography", Biochemistry, vol. 52, Issue 29, Jul. 23, 2013, 22 pages.

Fang et al., "Genome-Wide Mapping of Methylated Adenine Residues in Pathogenic *Escherichia Coli* Using Single-Molecule Real-Time Sequencing", Nature Biotechnology, vol. 30, Issue No. 12, Dec. 2012, pp. 1232-1243.

Favicchio et al., "Fluorescence Spectroscopy and Anisotropy in the Analysis of DNA-Protein Interactions", Methods in Molecular Biology, vol. 543, 2009, pp. 589-611.

Federley, "New Insights Into the Mechanism of DNA Replication on Unmodified and Benzo[a]pyrene Modified Templates Using Surface Plasmon Resonance", Wayne State University Dissertations, Paper 235., 2011, 208 pages.

Fuller et al., "The Challenges of Sequencing by Synthesis", Nature Biotechnology, vol. 27, Issue No. 11, Nov. 2009, pp. 1013-1023.

Gralla et al., "Potassium Glutamate as a Transcriptional Inhibitor During Bacterial Osmoregulation", The EMBO Journal, vol. 25, Issue No. 7, 2006, pp. 1515-1521.

Horn et al., "EML4-ALK: Honing in on a New Target in Non-Small-Cell Lung Cancer", Journal of Clinical Oncology, vol. 27, Issue No. 26, Sep. 10, 2009, pp. 4232-4235.

Hoshino et al., "Effect of Ultrasound on DNA Polymerase Reactions: Monitoring on a 27-MHz Quartz Crystal Microbalance", Biomacromolecules, vol. 7, Issue 3, 2006, pp. 682-685.

Nutter et al., "Labeled Nucleoside Triphosphates with Reversibly Terminating Aminoalkoxyl Groups", Nucleosides, Nucleotides and Nucleic Acids, vol. 29, Issue 11-12, 2010, pp. 879-895.

Ion Torrent, "Ion Torrent Amplicon Sequencing", Internet, Available Online at http://www.iontorrent.com/lib/images/PDFs/amplicon_application_note_040411.pdf, Apr. 4, 2011, pp. 1-5.

(56) References Cited

OTHER PUBLICATIONS

Jindal et al., "Suramin Affects DNA Synthesis in HeLa Cells by Inhibition of DNA Polymerases", Cancer Research, vol. 50, Dec. 15, 1990, pp. 7754-7757.

Jochmans et al., "Indolopyridones Inhibit Human Immunodeficiency Virus Reverse Transcriptase with a Novel Mechanism of Action", Journal of Virology, vol. 80, Issue No. 24, Dec. 2006, pp. 12283-12292.

Kaplan et al., "Photolabile Chelators for the Rapid Photorelease of Divalent Cations", Proc. Natl. Acad. Sci., vol. 85, Sep. 1988, pp. 6571-6575.

Kaushik et al., "Biochemical Analysis of Catalytically Crucial Aspartate Mutants of Human Immunodeficiency Virus Type 1 Reverse Transcriptase", Biochemistry, vol. 35, 1996, pp. 11536-11546.

Kim, "An FET-type Charge Sensor for Highly Sensitive Detection of DNA Sequence", Biosensors and Bioelectronics, vol. 20, Issue No. 1, 2004, pp. 69-74.

Klenow et al., "Effect of Monovalent Cations on the Activity of the DNA Polymerase of *Escherichia coli* B", European J. Biochem., vol. 9, 1969, pp. 133-141.

Kumar et al., "Altered Order of Substrate Binding by DNA Polymerase X from African Swine Fever Virus", Biochemistry, vol. 47, 2008, pp. 7875-7887.

Leinbach et al., "Mechanism of Phosphonoacetate Inhibition of Herpesvirus-Induced DNA Polymerase", Biochemistry, vol. 15, Issue 2, 1976, pp. 426-430.

Lutz et al., "An in Vitro Screening Technique for DNA Polymerases that can Incorporate Modified Nucleotides. Pseudothymidine as a Substrate for Thermostable Polymerases", Nucleic Acids Research, vol. 27, Issue No. 13, 1999, pp. 2792-2798.

Maga et al., "HIV-1 RT Inhibitors with a Novel Mechanism of Action: NNRTIs that Compete with the Nucleotide Substrate", Viruses, vol. 2, Issue 4, 2010, pp. 880-899.

Maga et al., "Selective Interaction of the Human Immunodeficiency Virus Type 1 Reverse Transcriptase Nonnucleoside Inhibitor Efavirenz and Its Thio-Subsitituted Analog with Different Enzyme-Substrate Complexes", Antimicrobial Agents and Chemotherapy, vol. 44, Issue No. 5, May 2000, pp. 1186-1194.

Mano, "Non-Solid Oncogenes in Solid Tumors: EML4-ALK Fusion Genes in Lung Cancer", Cancer Sci., vol. 99, Issue No. 12, Dec. 2008, pp. 2349-2355.

Markiewicz et al., "Single-Molecule Microscopy Reveals New Insights into Nucleotide Selection by DNA Polymerase I", Nucleic Acids Research, vol. 40, Issue No. 16, Jun. 4, 2012, pp. 7975-7984.

Mashayekhi, "Analysis of read length limiting factors in Pyrosequencing chemistry", Analytical Biochemistry, vol. 363, No. 2, Apr. 15, 2007, pp. 275-287.

Maxwell et al., "DNA Lesion Alters Global Conformational Dynamics of Y-family DNA Polymerase During Catalysis", The Journal of Biological Chemistry, vol. 287, Issue No. 16, Apr. 13, 2012, pp. 13040-13047.

Namasivayam, "Light-Induced Molecular Cutting: Localized Reaction on a Single DNA Molecule", Anal. Chem., vol. 75, Issue No. 16, Aug. 15, 2003, pp. 4118-4194.

Nath et al., "Label Free Colorimetric Biosensing Using Nanoparticles", Journal of Fluorescence, vol. 14, Issue 4, Jul. 2004, pp. 377-389.

Nazirizadeh et al., "Low-Cost Label-Free Biosensors Using Photonic Crystals Embedded Between Crossed Polarizers", Optics Express, vol. 18, Issue No. 18, Aug. 30, 2010, pp. 19120-19128.

Nikiforov, "Oligonucleotides Labeled With Single Fluorophores as Sensors for Deoxynucleotide Triphosphate Binding by DNA Polymerases", Analytical Biochemistry, vol. 444, 2014, pp. 60-66.

Patel, "Insights into DNA Polymerization Mechanisms from Structure and Function Analysis of HIV-1 Reverse Transcriptase.", Biochemistry, vol. 34, 1995, pp. 5351-5363.

PCT/US2017/030143, "International Preliminary Report on Patentability", dated Nov. 8, 2018, 7 pages.

PCT/US2017/030143, "International Search Report and Written Opinion", dated Jul. 28, 2017, 10 pages.

PCT/US2017/042843, "PCT Search Report", dated Oct. 2, 2017, 15 pages.

Peletskaya et al., "Cross-Linking of the Fingers Subdomain of Human Immunodeficiency Virus Type 1 Reverse Transcriptase to Template-Primer", Journal of Virology, vol. 75, Issue No. 19, Oct. 2001, pp. 9435-9445.

Pitta et al., "Synthesis and HIV-1 RT Inhibitory Action of Novel (4/6-substituted Benzo[d]thiazol-2-yl) Thiazolidin-4-ones. Divergence From the Non-competitive Inhibition Mechanism", Journal of Enzyme Inhibition and Medicinal Chemistry, vol. 28, Issue 1, 2013, pp. 113-122.

Potapova et al., "Interaction of dNTP, Pyrophosphate and their Analogs With the dNTP-binding Sites of *E. Coli* DNA Polymerase I Klenow Fragment and Human DNA Polymerase", FEBS letters, vol. 277, Issues 1-2, Dec. 1990, pp. 194-196.

Previte et al., "DNA Sequencing Using Polymerase Substrate-binding Kinetics", Nature Communication, vol. 6, Jan. 23, 2015, 12 pages.

Puttaswamy, "Optical Method for Measuring Spatial pH Change on Conductive Microelectrodes", Submitted in fulfillment for the International Master's Program (IMP) Nanomaterials and Nanotechnology, KTH, Royal Institute of Technology, 66 pages.

Ren et al., "Inhibition of Klenow DNA Polymerase and Poly(a)-Specific Ribonuclease by Aminoglycosides", RNA, vol. 8, 2002, pp. 1393-1400.

Richard et al., "Thermal Stability Landscape for Klenow DNA Polymerase as a Function of pH and Salt Concentration", Biochemica et Biophysica Acta, vol. 1764, 2006, pp. 1546-1552.

Roettger et al., "Mismatched and Matched dNTP Incorporation by DNA Polymerase β Proceed via Analogues Kinetic Pathways", Biochemistry, vol. 47, Issue No. 37, 2008, pp. 9718-9727.

Santoso et al., "Conformational Transitions in DNA Polymerase I Revealed by Single-Molecule Fret", Proceedings of the National Academy of Sciences, vol. 107, Issue No. 2, Jan. 12, 2010, pp. 715-720.

Schadt et al., "Modeling Kinetic Rate Variation in Third Generation DNA Sequencing Data to Detect Putative Modifications to DNA Bases", Genome Research, 2013, pp. 129-141.

Schultz et al., "Single-Target Molecule Detection With Nonbleaching Multicolor Optical Immunolabels", PNAS, vol. 96, Issue No. 3, Feb. 1, 2000, pp. 996-1001.

Sen et al., "Intrinsic Fluorescence of *E. coli* RNA Polymerase as a Probe for Its Conformational Changes During Transcription Initiation", Biochem Biophys Res Commun, vol. 201, Issue 2, Jun. 15, 1994, pp. 820-828.

Soda et al., "Identification of the Transforming EML4-ALK Fusion Gene in Non-Small-Cell Lung Cancer", Nature, vol. 228, Aug. 2, 2007, pp. 561-566.

Star et al., "Electronic Detection of Specific Protein Binding Using Nanotube FET Devices", Nano Letters, vol. 3, Issue No. 4, Apr. 1, 2003, pp. 459-463.

Su et al., "Surface Plasmon Resonance Spectroscopy and Quartz Crystal Microbalance Study of Streptavidin Film Structure Effects on Biotinylated Dna Assembly and Target DNA Hybridization", Langmuir, vol. 21, Issue 1, 2005, pp. 348-353.

Tsai, "Kinetics of DNA Polymerase Conformational Changes during Nucleotide Binding and Incorporation", Dissertation, May 2005, pp. 1-48.

Tsai et al., "Site-Specific Labeling of T7 DNA Polymerase with a Conformationally Sensitive Flurophore and its Use in Detecting Single-Nucleotide Polymorphisms", Analytical Biochemistry, vol. 384, No. 1, Academic Press Inc., New York, Jan. 1, 2009, pp. 136-144.

Vaidyanathan et al., "Binary and Ternary Binding Affinities Between Exonuclease-Deficient Klenow Fragment (Kf-exo-) and Various Arylamine DNA Lesions Characterized by Surface Plasmon Resonance", Chem Res Toxicol, vol. 25, Issue 8, Aug. 20, 2012, pp. 1568-1570.

Vaidyanathan et al., "Binding Kinetics of DNA-Protein Interaction Using Surface Plasmon Resonance", Protocol Exchange, May 22, 2013, 11 pages.

(56) References Cited

OTHER PUBLICATIONS

Vollmer et al., "Whispering-Gallery-Mode Biosensing: Label-Free Detection Down to Single Molecules.", Nature Methods, vol. 5, Issue No. 7, Jul. 2008, pp. 591-596.
Walsh et al., "Synthetic Nucleotides as Probes of DNA Polymerase Specificity", Journal of Nucleic Acids, vol. 2012, Article ID 530963, Jun. 2012, 17 pages.
Washington et al., "Human DNA Polymerase Utilizes Different Nucleotide Incorporation Mechanisms Dependent upon the Template Base", Molecular and Cellular Biology, vol. 24, No. 2, Jan. 2004, 936-943.
Xia et al., "DNA Mismatch Synthesis Complexes Provide Insights into Base Selectivity of a B family DNA Polymerase", J Am Chem Soc. vol. 135, Issue 1, Jan. 9, 2013, pp. 193-202.
Yuzenkova et al., "Tagetitoxin Inhibits Transcription by Stabilizing Pre-Translocated State of the Elongation Complex", Nucleic Acids Research, 2013, pp. 9257-9265.
PCT/US2017/042843, "International Preliminary Report on Patentability", dated Feb. 28, 2019, 8 pages.
CA3,021,769, "Office Action", dated Oct. 10, 2019, 4 pages.

SEQUENCING METHOD EMPLOYING TERNARY COMPLEX DESTABILIZATION TO IDENTIFY COGNATE NUCLEOTIDES

RELATED APPLICATIONS

This application is a continuation of U.S. application Ser. No. 15/581,828, filed on Apr. 28, 2017, which claims the benefit of U.S. Provisional Application No. 62/329,933, filed Apr. 29, 2016, and U.S. Provisional Patent Application No. 62/487,586, filed Apr. 20, 2017. The entire disclosures of these earlier applications are hereby incorporated by reference.

TECHNICAL FIELD

The present invention relates generally to the field of biotechnology. More specifically, the invention concerns nucleic acid sequencing technology.

BACKGROUND

Acquiring accurate nucleic acid sequence information in a rapid and cost-effective manner is essential for the modern era of genomic analysis. Certain automated DNA sequencing platforms require iterative cycles of enzyme-based nucleotide binding, incorporation into an extending primer, detection of incorporation reaction products, and even chemical modification of the extended primer to render it useful in a subsequent cycle. Repeating the cycle for up to four candidate nucleotides to identify the cognate nucleotide at a single position along a DNA template complicates the workflow, and increases reagent costs.

Stretches of more than one of the same base along a strand of nucleic acid are among factors confounding accurate sequence determination. These "homopolymer" stretches can be overlooked by some sequencing approaches, such that a single base will be detected when multiples actually are present. Some sequencing methods further can experience "phasing" issues that can be promoted by the presence of homopolymer stretches. As a consequence of phasing, sequence determination downstream of the homopolymer stretch can be rendered ambiguous.

Despite the many advances reported in the field of nucleic acid sequencing technology, there remains a need for improved systems that deliver accurate results quickly.

BRIEF DESCRIPTION OF THE DRAWINGS

FIG. 5A presents results obtained using Bsu DNA polymerase in the examination steps. FIG. 5B presents results obtained using Bst 2.0 DNA polymerase in the examination steps. All examination cycles were conducted after incorporating the correct reversible terminator nucleotide, and before cleavage of 3'-$ONH_2$ reversible terminator moiety of the primer to reveal an extendable 3'-OH group. Both figures display numerical indicators (1-8) of repetitive process steps, with certain wash or regeneration steps therebetween: (1) incorporation of a reversible terminator nucleotide; (2) contacting with polymerase in the absence of any nucleotide; (3) contacting with the combination of polymerase, dATP, and dTTP; (4) contacting with the combination of polymerase and dATP; (5) contacting with polymerase in the absence of any nucleotide; (6) contacting with the combination of polymerase, dGTP, and dCTP; (7) contacting with the combination of polymerase and dCTP; and (8) chemical cleavage or removal of the reversible terminator moiety.

SUMMARY OF THE DISCLOSURE

Figure 1:
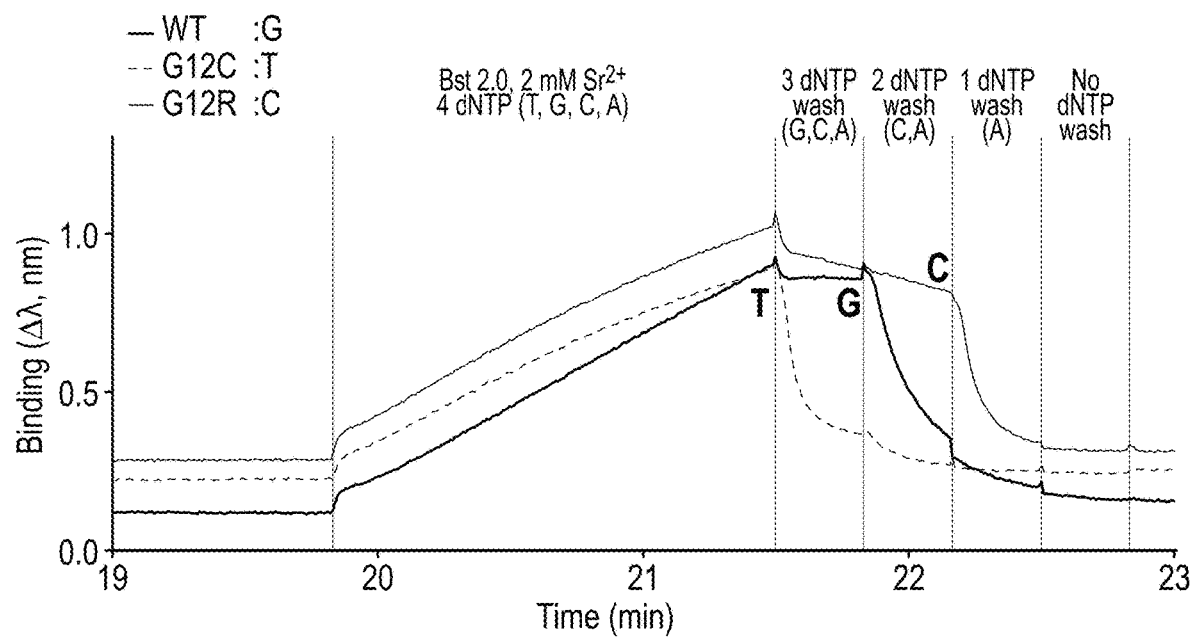
FIG. 1 is an interferometry trace for interrogation of the first base in codon 12 of the KRAS wildtype (WT: GGT) and mutant (G12C: TGT; and G12R: CGT) sequences. Three different correct bases are shown at the same position for the three different template nucleic acids. The next correct nucleotides harboring the correct bases are highlighted in bold.

In one aspect, the disclosure relates to a method of identifying a nucleotide having a base complementary to the next base of a template strand immediately downstream of a primer in a primed template nucleic acid molecule. The method includes the steps of: (a) providing a blocked primed template nucleic acid molecule including a reversible terminator moiety that precludes the 3'-terminus of the blocked primed template nucleic acid molecule from participating in phosphodiester bond formation; (b) contacting the blocked primed template nucleic acid molecule with a first reaction mixture that includes a polymerase, and a plurality of different nucleotide molecules, whereby a stabilized ternary complex forms, the stabilized ternary complex including one of the plurality of different nucleotide molecules; (c) contacting the stabilized ternary complex with a second reaction mixture that includes at least one of the different nucleotide molecules and that does not include a first nucleotide molecule of the plurality of different nucleotide molecules; (d) monitoring interaction of the polymerase and the blocked primed template nucleic acid molecule in contact with the second reaction mixture to detect any of the stabilized ternary complex remaining after step (c); and (e) identifying the nucleotide that includes the base complementary to the next base of the template strand using results from step (d). According to one generally preferred embodiment, the method further includes the step of (f) removing the reversible terminator moiety from the blocked primed template nucleic acid molecule after step (d). More preferably, step (e) can involve determining either that: (i) the first nucleotide molecule in step (c) includes the base complementary to the next base of the template strand if the stabilized ternary complex dissociates in step (d), or (ii) the first nucleotide molecule in step (c) does not include the base complementary to the next base of the template strand if the stabilized ternary complex is retained in step (d). Still more preferably, the polymerase of the first reaction mixture can include an exogenous fluorescent label. Alternatively, the plurality of different nucleotide molecules in the first reaction mixture can be either a plurality of different native nucleotide molecules, or a plurality of different fluorescently labeled nucleotide molecules. When this is the case, the first reaction mixture may further include a catalytic metal ion. Alternatively, the first reaction mixture does not include non-catalytic metal ions that inhibit phosphodiester bond formation by the polymerase of the first reaction mixture, and the first reaction mixture further includes a catalytic metal ion. According to other embodiments, where the method further includes the step of (f) removing the reversible terminator moiety from the blocked primed template nucleic acid molecule after step (d), and where step (e) can involve determining either that: (i) the first nucleotide molecule in step (c) includes the base complementary to the next base of the template strand if the stabilized ternary complex dissociates in step (d), or (ii) the first nucleotide molecule in step (c) does not include the base complementary to the next base of the template strand if the stabilized ternary complex is retained in step (d); step (a) can involve incorporating, with a polymerase, a reversible terminator nucleotide at the 3'-end of the primer of the primed template nucleic acid molecule, whereby there is produced the blocked primed template nucleic acid molecule including the reversible terminator moiety that precludes the 3'-terminus of the blocked primed template nucleic acid molecule from participating in phosphodiester bond formation. According to one preferred embodiment, the method further includes, after step (a) and before step (b), the step of contacting the blocked primed template nucleic acid molecule with the polymerase of the first reaction mixture in the absence the plurality of different nucleotide molecules. According to another preferred embodiment, the second reaction mixture includes the same polymerase that is present in the first reaction mixture. According to yet another preferred embodiment, the method further includes, after step (a) and before step (b), the step of contacting the blocked primed template nucleic acid molecule with the polymerase of the first reaction mixture in the absence of the plurality of different nucleotide molecules. For example, the first reaction mixture can further include a catalytic metal ion. Alternatively, the second reaction mixture can include the same polymerase that is present in the first reaction mixture. According to still other embodiments, where the method further includes the step of (f) removing the reversible terminator moiety from the blocked primed template nucleic acid molecule after step (d), and where step (e) can involve determining either that: (i) the first nucleotide molecule in step (c) includes the base complementary to the next base of the template strand if the stabilized ternary complex dissociates in step (d), or (ii) the first nucleotide molecule in step (c) does not include the base complementary to the next base of the template strand if the stabilized ternary complex is retained in step (d), and where step (a) involves incorporating, with a polymerase, a reversible terminator nucleotide at the 3'-end of the primer of the primed template nucleic acid molecule, whereby there is produced the blocked primed template nucleic acid molecule including the reversible terminator moiety that precludes the 3'-terminus of the blocked primed template nucleic acid molecule from participating in phosphodiester bond formation, the method can further involve repeating steps (b)-(e) a plurality of times. Here, the polymerase used in step (a) and the polymerase of the first reaction mixture in step (b) can be different types of polymerase enzymes. Alternatively, the polymerase of the first reaction mixture includes an exogenous fluorescent label. Alternatively, the plurality of different nucleotide molecules in the first reaction mixture can be either a plurality of different native nucleotide molecules, or a plurality of different fluorescently labeled nucleotide molecules. Alternatively, the first reaction mixture further includes a catalytic metal ion. Alternatively, the first reaction mixture does not include non-catalytic metal ions that inhibit phosphodiester bond formation by the polymerase of the first reaction mixture. Alternatively, step (f) is performed before step (e). Alternatively, the second reaction mixture includes the same polymerase that is present in the first reaction mixture.

In another aspect, the disclosure relates to a method of identifying a nucleotide having a base complementary to the next base of a template strand immediately downstream of a primer in a primed template nucleic acid molecule. The method includes the steps of: (a) providing the primed template nucleic acid molecule; (b) contacting the primed template nucleic acid molecule with a first reaction mixture that includes a polymerase and a plurality of different nucleotide molecules, whereby a stabilized ternary complex forms, the stabilized ternary complex including one of the plurality of different nucleotide molecules; (c) contacting the primed template nucleic acid molecule, after step (b), with a second reaction mixture that includes at least one of the different nucleotide molecules and that does not include a first nucleotide molecule of the plurality of different nucleotide molecules; (d) monitoring interaction of the polymerase and the primed template nucleic acid molecule in the second reaction mixture, without incorporating any nucleotide into the primer, to detect any of the stabilized ternary complex remaining after step (c); and (e) identifying the nucleotide that includes the base complementary to the next base of the template strand using results from step (d). According to one generally preferred embodiment, step (d) includes monitoring the rate of dissociation of the polymerase from the primed template nucleic acid molecule in the stabilized ternary complex. According to a different generally preferred embodiment, the plurality of different nucleotide molecules includes a plurality of different unlabeled nucleotide molecules. More preferably, the polymerase of the first reaction mixture includes an exogenous fluorescent label producing a detectable signal that is substantially unchanged in the presence or absence of the next correct nucleotide. Alternatively, the first reaction mixture includes four different types of native nucleotide molecules, and the second reaction mixture does not include one of the four different types of native nucleotide molecules. Alternatively, the first reaction mixture includes two different types of native nucleotide molecules, and the second reaction mixture does not include one of the two different types of native nucleotide molecules. Alternatively, the method further includes an incorporation step that involves removing any of the plurality of different nucleotide molecules remaining in contact with the primed template nucleic acid after step (d), contacting the primed template nucleic acid with a third reaction mixture that includes a polymerase and at least one reversible terminator, and then incorporating a single reversible terminator into the primer. Preferably, the polymerase of the first reaction mixture and the polymerase of the third reaction mixture are different types of DNA polymerase, and the polymerase of the first reaction mixture includes an exogenous detectable label. More preferably, the exogenous detectable label includes a fluorescent label that is substantially unchanged in the presence or absence of the next correct nucleotide. According to another generally preferred embodiment, the method further includes an incorporation step that involves removing any of the plurality of different nucleotide molecules remaining in contact with the primed template nucleic acid after step (d), contacting the primed template nucleic acid with a third reaction mixture that includes a polymerase and a nucleotide, and then incorporating the nucleotide of the third reaction mixture into the primer. According to another generally preferred embodiment, the method further includes an incorporation step that involves removing any of the plurality of different nucleotide molecules remaining in contact with the primed template nucleic acid after step (d), contacting the primed template nucleic acid with a third reaction mixture that includes a polymerase and at least one reversible terminator, and then incorporating a single reversible terminator into the primer. According to generally preferred embodiments wherein the method further includes an incorporation step that involves removing any of the plurality of different nucleotide molecules remaining in contact with the primed template nucleic acid after step (d), contacting the primed template nucleic acid with a third reaction mixture that includes a polymerase and a nucleotide, and then incorporating the nucleotide of the third reaction mixture into the primer, the method can further include repeating each of steps (b)-(e) and the incorporation step. According to some embodiments, when the method further includes an incorporation step that involves removing any of the plurality of different nucleotide molecules remaining in contact with the primed template nucleic acid after step (d), contacting the primed template nucleic acid with a third reaction mixture that includes a polymerase and at least one reversible terminator, and then incorporating a single reversible terminator into the primer, the polymerase of the first reaction mixture and the polymerase of the third reaction mixture can be different types of DNA polymerase. More preferably, the polymerase of the first reaction mixture can include an exogenous fluorescent label that is not sensitive to nucleotide binding. According to some embodiments, when the method further includes an incorporation step that involves removing any of the plurality of different nucleotide molecules remaining in contact with the primed template nucleic acid after step (d), contacting the primed template nucleic acid with a third reaction mixture that includes a polymerase and at least one reversible terminator, and then incorporating a single reversible terminator into the primer, the at least one reversible terminator can include a plurality of different types of reversible terminators. More preferably, the plurality of different types of reversible terminators can include four different reversible terminators. According to another generally preferred embodiment, step (e) includes determining either that (i) the first nucleotide molecule includes the base complementary to the next base of the template strand if the stabilized ternary complex dissociates in step (d), or (ii) the first nucleotide molecule does not include the base complementary to the next base of the template strand if the stabilized ternary complex is retained in step (d). According to another generally preferred embodiment, after step (b) and before step (c) there is a step (b)(i) that includes monitoring interaction of the primed template nucleic acid molecule with the polymerase in the first reaction mixture, without incorporating any nucleotides molecule into the primer, to detect any of the stabilized ternary complex that formed in step (b). More preferably, step (e) involves determining that the first reaction mixture does not include the base complementary to the next base of the template strand if the stabilized ternary complex was not detected in step (b)(i). According to another generally preferred embodiment, when step (d) includes monitoring the rate of dissociation of the polymerase from the primed template nucleic acid molecule in the stabilized ternary complex, and the plurality of different nucleotide molecules include a plurality of different native nucleotide molecules, the method further includes an incorporation step. The incorporation step can include removing any of the plurality of different nucleotide molecules remaining in contact with the primed template nucleic acid after step (d), contacting the primed template nucleic acid with a third reaction mixture that includes a polymerase and at least one reversible terminator, and then incorporating a single reversible terminator into the primer. Here, the polymerase of the first reaction mixture and the polymerase of the third reaction mixture are different types of DNA polymerase.

In yet another aspect, the disclosure relates to a method of identifying a nucleotide including a base complementary to the next base of a template strand immediately downstream of a primer in a primed template nucleic acid molecule. The method includes the steps of: (a) providing the primed template nucleic acid molecule; (b) contacting the primed template nucleic acid molecule with a first reaction mixture that includes a polymerase, but does not include any nucleotide, whereby a binary complex forms; (c) contacting the binary complex with a second reaction mixture that includes a plurality of different nucleotide molecules, whereby a stabilized ternary complex forms if one of the plurality of different nucleotide molecules includes the base complementary to the next base of the template strand; (d) detecting, without incorporating any nucleotide into the primer, any of the stabilized ternary complex that may have formed; (e) contacting the primed template nucleic acid molecule, after step (d), with a third reaction mixture that includes at least one of the different nucleotide molecules and that does not include a first nucleotide molecule of the plurality of different nucleotide molecules; (f) detecting, without incorporating any nucleotide into the primer, any of the stabilized ternary complex remaining after step (e); and (g) identifying the nucleotide that includes the base complementary to the next base of the template strand using results from both of detecting steps (d) and (f). According to one generally preferred embodiment, the method further includes an incorporation step that involves first replacing the third reaction mixture in contact with the primed template nucleic acid molecule with a fourth reaction mixture that includes a polymerase and at least one reversible terminator, and then incorporating the at least one reversible terminator into the primer. According to a different generally preferred embodiment, step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f). More preferably, the method further includes an incorporation step that involves first replacing the third reaction mixture in contact with the primed template nucleic acid molecule with a fourth reaction mixture that includes a polymerase and at least one reversible terminator, and then incorporating the at least one reversible terminator into the primer. Alternatively, the method further includes an incorporation step that involves first replacing the third reaction mixture in contact with the primed template nucleic acid molecule with a fourth reaction mixture that includes a polymerase and at least one reversible terminator, and then incorporating the at least one reversible terminator into the primer, and wherein the polymerase of the first reaction mixture and the polymerase of the fourth reaction mixture are different types of DNA polymerase. When this is the case, steps (b)-(f) can be repeated two times using different nucleotides before the incorporation step is performed. According to a different generally preferred embodiment, when step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f), steps (b)-(f) can be repeated a plurality of times. According to a different generally preferred embodiment, when step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f), the primed template nucleic acid molecule of step (a) can be immobilized to a surface. When this is the case, the primed template nucleic acid molecule of step (a) can be immobilized to a streptavidin-coated surface. According to a different generally preferred embodiment, when step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f), step (g) can be performed by a computer programmed with software. According to a different generally preferred embodiment, when step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f), detecting steps (d) and (f) can involve optical detection. More preferably, detecting steps (d) and (f) can involve detecting by interferometry. Alternatively, detecting steps (d) and (f) can involve detecting by surface plasmon resonance sensing. According to a different generally preferred embodiment, when step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f); and when the primed template nucleic acid molecule of step (a) is immobilized to a surface, step (c) can involve replacing the first reaction mixture with the second reaction mixture by flowing the second reaction mixture over the primed template nucleic acid molecule that is immobilized to the surface. According to a different generally preferred embodiment, when step (g) involves determining either that (i) the first nucleotide molecule includes the base complementary to the next base of the template strand if the stabilized ternary complex was detected in step (d) but was not detected in step (f), or (ii) the first nucleotide molecule does not include the base complementary to the next base of the template strand if the stabilized ternary complex was detected in both of steps (d) and (f), or (iii) the first reaction mixture does not include the nucleotide including the base complementary to the next base of the template strand if the stabilized ternary complex was not detected in at least one of steps (d) and (f); and when the primed template nucleic acid molecule of step (a) is immobilized to a surface, step (c) can involve replacing the first reaction mixture with the second reaction mixture by physically moving the primed template nucleic acid molecule that is immobilized to the surface from the first reaction mixture to the second reaction mixture. According to still yet another generally preferred embodiment, the primed template nucleic acid molecule of step (a) is immobilized to a surface, and wherein step (d) includes either: replacing the first reaction mixture with the second reaction mixture by flowing the second reaction mixture over the primed template nucleic acid molecule that is immobilized to the surface, or replacing the first reaction mixture with the second reaction mixture by physically moving the primed template nucleic acid molecule that is immobilized to the surface from the first reaction mixture to the second reaction mixture.

DETAILED DESCRIPTION

Disclosed is a technique for detecting ternary complexes that include a primed template nucleic acid molecule, a polymerase, and the next correct nucleotide immediately downstream of the primer and complementary to the template strand of a primed template nucleic acid. Clear and unambiguous detection has been achieved despite interactions between the polymerase and the primed template nucleic acid that promote formation of nucleotide-independent complexes.

The technique involves initial formation of a ternary complex using a plurality of nucleotides, and then subsequently investigating stability of the complex under a series of changed reagent conditions. These changed conditions involve progressive removal of nucleotides from a controlled series of binding reaction mixtures. For example, a ternary complex that includes a particular dNTP will require that dNTP in a first reagent solution to maintain integrity of the complex. Exchanging the first reagent solution with a second reagent solution that does not include the critical dNTP will cause destabilization of the complex, which can be detected as an indicator of nucleotide identity. This approach permits a single incorporation reaction to be performed at the conclusion of multiple examinations, thereby reducing the number of steps and incorporation reagents needed to identify a single position along a primed template nucleic acid.

Advantageously, the technique can be practiced using various types of nucleotides, including native (e.g., unlabeled) nucleotides, nucleotides with detectable labels (e.g., fluorescent or other optically detectable labels), or labeled or unlabeled nucleotide analogs (e.g., modified nucleotides containing reversible terminator moieties). Further, the technique provides controlled reaction conditions, unambiguous determination of sequence, low overall cost of reagents, and low instrument cost.

The disclosed technique can be applied to binding reactions used for determining the identity of the next base of a primed template nucleic acid by any means and for any reason. The technique can be used to monitor specific binding of a DNA polymerase and the next correct nucleotide (e.g., a dNTP) complementary to a primed template nucleic acid, and to distinguish specific binding from non-specific binding. The technique may be applied to single nucleotide determination (e.g., SNP determination), or alternatively to more extensive nucleic acid sequencing procedures employing reiterative cycles that identify one nucleotide at a time. For example, the methods provided herein can be used in connection with sequencing-by-binding procedures, as described in the commonly owned U.S. patent application identified by Ser. No. 14/805,381, the disclosure of which is incorporated by reference herein in its entirety.

Definitions

Unless defined otherwise, all technical and scientific terms used herein have the same meaning as is commonly understood by one of ordinary skill in the art. For clarity, the following specific terms have the specified meanings. Other terms are defined in other sections herein.

The singular forms "a" "an" and "the" include plural referents unless the context clearly dictates otherwise. Approximating language, as used in the description and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the compositions, apparatus, or methods of the present disclosure. At the very least, each numerical parameter should at least be construed in light of the number of reported significant digits and by applying ordinary rounding techniques.

As used herein, "sequencing-by-binding" refers to a sequencing technique wherein specific binding of a polymerase to a primed template nucleic acid is used for identifying the next correct nucleotide to be incorporated into the primer strand of the primed template nucleic acid. The specific binding interaction precedes chemical incorporation of the nucleotide into the primer strand, and so identification of the next correct nucleotide can take place either without or before incorporation of the next correct nucleotide.

As used herein, "nucleic acid" or "oligonucleotide" or "polynucleotide" or grammatical equivalents used herein means at least two nucleotides covalently linked together. Thus, a "nucleic acid" is a polynucleotide, such as DNA, RNA, or any combination thereof, that can be acted upon by a polymerizing enzyme during nucleic acid synthesis. The term "nucleic acid" includes single-, double-, or multiple-stranded DNA, RNA and analogs (derivatives) thereof. Double-stranded nucleic acids advantageously can minimize secondary structures that may hinder nucleic acid synthesis. A double stranded nucleic acid may possess a nick or a single-stranded gap.

As used herein, a "template nucleic acid" is a nucleic acid to be detected or sequenced using any sequencing method disclosed herein.

As used herein, a "primed template nucleic acid" (or alternatively, "primed template nucleic acid molecule") is a template nucleic acid primed with (i.e., hybridized to) a primer, wherein the primer is an oligonucleotide having a 3'-end with a sequence complementary to a portion of the template nucleic acid. The primer can optionally have a free 5'-end (e.g., the primer being noncovalently associated with the template) or the primer can be continuous with the template (e.g., via a hairpin structure). The primed template nucleic acid includes the complementary primer and the template nucleic acid to which it is bound. Unless explicitly stated, a primed template nucleic acid can have either a 3'-end that is extendible by a polymerase, or a 3'-end that is blocked from extension.

As used herein, a "blocked primed template nucleic acid" (or alternatively, "blocked primed template nucleic acid molecule") is a primed template nucleic acid modified to preclude or prevent phosphodiester bond formation at the 3'-end of the primer. Blocking may be accomplished, for example, by chemical modification with a blocking group at either the 3' or 2' position of the five-carbon sugar at the 3' terminus of the primer. Alternatively, or in addition, chemical modifications that preclude or prevent phosphodiester bond formation may also be made to the nitrogenous base of a nucleotide. Reversible terminator nucleotide analogs including each of these types of blocking groups will be familiar to those having an ordinary level of skill in the art. Incorporation of these analogs at the 3' terminus of a primer of a primed template nucleic acid molecule results in a blocked primed template nucleic acid molecule. The blocked primed template nucleic acid includes the complementary primer, blocked from extension at its 3'-end, and the template nucleic acid to which it is bound.

As used herein, a "nucleotide" is a molecule that includes a nitrogenous base, a five-carbon sugar (ribose or deoxyribose), and at least one phosphate group. The term embraces, but is not limited to, ribonucleotides, deoxyribonucleotides, nucleotides modified to include exogenous labels or reversible terminators, and nucleotide analogs.

As used herein, a "native" nucleotide refers to a naturally occurring nucleotide that does not include an exogenous label (e.g., a fluorescent dye, or other label) or chemical modification such as may characterize a nucleotide analog. Examples of native nucleotides useful for carrying out the sequencing-by-binding procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, a "nucleotide analog" has one or more modifications, such as chemical moieties, which replace, remove and/or modify any of the components (e.g., nitrogenous base, five-carbon sugar, or phosphate group(s)) of a native nucleotide. Nucleotide analogs may be either incorporable or non-incorporable by a polymerase in a nucleic acid polymerization reaction. Optionally, the 3'-OH group of a nucleotide analog is modified with a moiety. The moiety may be a 3' reversible or irreversible terminator of polymerase extension. The base of a nucleotide may be any of adenine, cytosine, guanine, thymine, or uracil, or analogs thereof. Optionally, a nucleotide has an inosine, xanthine, hypoxanthine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dUTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP, ddUTP and ddCTP).

As used herein, the "next template nucleotide" (or the "next template base") refers to the next nucleotide (or base) in a template nucleic acid that is located immediately downstream of the 3'-end of a hybridized primer.

As used herein, the "next correct nucleotide" (sometimes referred to as the "cognate" nucleotide) refers to the nucleotide type that will bind and/or incorporate at the 3' end of a primer to complement a base in a template strand to which the primer is hybridized. The base in the template strand is referred to as the "next template nucleotide" and is immediately 5' of the base in the template that is hybridized to the 3' end of the primer. The next correct nucleotide can be, but need not necessarily be, capable of being incorporated at the 3' end of the primer. For example, the next correct nucleotide can be a member of a ternary complex that will complete an incorporation reaction or, alternatively, the next correct nucleotide can be a member of a stabilized ternary complex that does not catalyze an incorporation reaction. A nucleotide having a base that is not complementary to the next template base is referred to as an "incorrect" (or "non-cognate") nucleotide.

As used herein, a "blocking moiety," when used with reference to a nucleotide analog, is a part of the nucleotide that inhibits or prevents the nucleotide from forming a covalent linkage to a second nucleotide (e.g., via the 3'-oxygen of a primer nucleotide) during the incorporation step of a nucleic acid polymerization reaction. The blocking moiety of a "reversible terminator" nucleotide can be removed from the nucleotide analog to allow for nucleotide incorporation. Such a blocking moiety is referred to herein as a "reversible terminator moiety." Exemplary reversible terminator moieties are set forth in U.S. Pat. Nos. 7,427,673; 7,414,116; and 7,057,026 and PCT publications WO 91/06678 and WO 07/123744, each of which is incorporated by reference.

As used herein, a "test nucleotide" is a nucleotide being investigated for its ability to participate in formation of a ternary complex that further includes a primed template nucleic acid and a polymerase.

As used herein, a "polymerase" is a generic term for a nucleic acid synthesizing enzyme, including but not limited to, DNA polymerase, RNA polymerase, reverse transcriptase, primase and transferase. Typically, the polymerase includes one or more active sites at which nucleotide binding and/or catalysis of nucleotide polymerization may occur. The polymerase may catalyze the polymerization of nucleotides to the 3'-end of a primer bound to its complementary nucleic acid strand. For example, a polymerase can catalyze the addition of a next correct nucleotide to the 3' oxygen of the primer via a phosphodiester bond, thereby chemically incorporating the nucleotide into the primer. Optionally, the polymerase used in the provided methods is a processive polymerase. Optionally, the polymerase used in the provided methods is a distributive polymerase. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, a "salt providing monovalent cation" is an ionic compound that dissociates in aqueous solution to produce cations having a single positive charge. For example, the cations can be metal cations where the oxidation state is +1.

As used herein, "a glutamate salt" is an ionic compound that dissociates in aqueous solution to produce glutamate anions.

As used herein, "biphasic" refers to a two-stage process wherein a primed template nucleic acid is contacted with a polymerase and a test nucleotide. The first phase of the process involves contacting the primed template nucleic acid with a polymerase in the presence of a sub-saturating level of nucleotide(s), or even in the absence of nucleotides. The term "sub-saturating," when used in reference to ligand that binds to a receptor (e.g., a nucleotide that binds to a polymerase), refers to a concentration of the ligand that is below that required to result in at least 90% of the receptors being bound to the ligand at equilibrium. For example, a sub-saturating amount of nucleotide can yield at least 90%, 95%, 99% or more polymerases being bound to the nucleotide. The second phase of the process involves contacting the primed template nucleic acid from the first phase with a polymerase in the presence of a higher concentration of nucleotide(s) than used in the first phase, where the higher concentration is sufficient to yield maximal ternary complex formation when a nucleotide in the reaction is the next correct nucleotide.

As used herein, "providing" a template, a primer, a primed template nucleic acid, or a blocked primed template nucleic acid refers to the preparation and delivery of one or many nucleic acid polymers, for example to a reaction mixture or reaction chamber.

As used herein, "monitoring" (or sometimes "measuring") refers to a process of detecting a measurable interaction or binding between two molecular species. For example, monitoring may involve detecting measurable interactions between a polymerase and primed template nucleic acid, typically at various points throughout a procedure. Monitoring can be intermittent (e.g., periodic) or continuous (e.g., without interruption), and can involve acquisition of quantitative results. Monitoring can be carried out by detecting multiple signals over a period of time during a binding event or, alternatively, by detecting signal(s) at a single time point during or after a binding event.

As used herein, the term "solid support" refers to a rigid substrate that is insoluble in aqueous liquid. The substrate can be non-porous or porous. The substrate can optionally be capable of taking up a liquid (e.g., due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, "contacting" refers to the mixing together of reagents (e.g., mixing an immobilized template nucleic acid and either a buffered solution that includes a polymerase, or the combination of a polymerase and a test nucleotide) so that a physical binding reaction or a chemical reaction may take place.

As used herein, "incorporating" or "chemically incorporating" refers to the process of joining a cognate nucleotide to a primer by formation of a phosphodiester bond.

As used herein, a "binary complex" is an intermolecular association between a polymerase and a primed template nucleic acid (or blocked primed template nucleic acid), where the complex does not include a nucleotide molecule such as the next correct nucleotide.

As used herein, a "ternary complex" is an intermolecular association between a polymerase, a primed template nucleic acid (or blocked primed template nucleic acid), and the next correct nucleotide positioned immediately downstream of the primer and complementary to the template strand of the primed template nucleic acid or the blocked primed template nucleic acid. The primed template nucleic acid can include, for example, a primer with a free 3'-OH or a blocked primer (e.g., a primer with a chemical modification on the base or the sugar moiety of the 3' terminal nucleotide, where the modification precludes enzymatic phosphodiester bond formation). The term "stabilized ternary complex" means a ternary complex having promoted or prolonged existence or a ternary complex for which disruption has been inhibited. Generally, stabilization of the ternary complex prevents covalent incorporation of the nucleotide component of the ternary complex into the primed nucleic acid component of the ternary complex.

As used herein, a "catalytic metal ion" refers to a metal ion that facilitates phosphodiester bond formation between the 3'-OH of a nucleic acid (e.g., a primer) and the phosphate of an incoming nucleotide by a polymerase. A "divalent catalytic metal cation" is a catalytic metal ion having a valence of two. Catalytic metal ions can be present at concentrations necessary to stabilize formation of a complex between a polymerase, a nucleotide, and a primed template nucleic acid, referred to as non-catalytic concentrations of a metal ion. Catalytic concentrations of a metal ion refer to the amount of a metal ion sufficient for polymerases to catalyze the reaction between the 3'-OH group of a nucleic acid (e.g., a primer) and the phosphate group of an incoming nucleotide.

As used herein, a "non-catalytic metal ion" refers to a metal ion that, when in the presence of a polymerase enzyme, does not facilitate phosphodiester bond formation needed for chemical incorporation of a nucleotide into a primer. Typically, the non-catalytic metal ion is a cation. A non-catalytic metal ion may inhibit phosphodiester bond formation by a polymerase, and so may stabilize a ternary complex by preventing nucleotide incorporation. Non-catalytic metal ions may interact with polymerases, for example, via competitive binding compared to catalytic metal ions. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein an "exogenous label" refers to a detectable chemical moiety that has been added to a sequencing reagent, such as a nucleotide or a polymerase (e.g., a DNA polymerase). While a native dNTP may have a characteristic limited fluorescence profile, the native dNTP does not include any added colorimetric or fluorescent moiety. Conversely, a dATP (2'-deoxyadenosine-5'-triphosphate) molecule modified to include a chemical linker and fluorescent moiety attached to the gamma phosphate would be said to include an exogenous label because the attached chemical components are not ordinarily a part of the nucleotide. Of course, chemical modifications to add detectable labels to nucleotide bases also would be considered exogenous labels. Likewise, a DNA polymerase modified to include a conformationally sensitive fluorescent dye that changes its properties upon nucleotide binding also would be said to include an exogenous label because the label is not ordinarily a part of the polymerase.

As used herein, "unlabeled" refers to a molecular species free of added or exogenous label(s) or tag(s). Of course, unlabeled nucleotides will not include either of an exogenous fluorescent label, or an exogenous Raman scattering tag. A native nucleotide is another example of an unlabeled molecular species. An unlabeled molecular species can exclude one or more of the labels set forth herein or otherwise known in the art relevant to nucleic acid sequencing or analytical biochemistry.

Sequencing-by-Binding

Described herein are polymerase-based, nucleic acid sequencing-by-binding (SBB) reactions, wherein the polymerase undergoes conformational transitions between open and closed conformations during discrete steps of the reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation including a polymerase, primed template nucleic acid and nucleotide; wherein the bound nucleotide has not been incorporated. This step, also referred to herein as the "examination" step, may be followed by a chemical step wherein a phosphodiester bond is formed with concomitant pyrophosphate cleavage from the nucleotide (i.e., nucleotide incorporation). The polymerase, primed template nucleic acid and newly incorporated nucleotide produce a post-chemistry, pre-translocation conformation. As both the pre-chemistry conformation and the pre-translocation conformation include a polymerase, primed template nucleic acid and nucleotide, wherein the polymerase is in a closed state, either conformation may be referred to herein as a closed-complex or a closed ternary complex. In the closed pre-insertion state, divalent catalytic metal ions, such as $Mg^{2+}$ mediate a rapid chemical reaction involving nucleophilic displacement of a pyrophosphate (PPi) by the 3' hydroxyl of the primer. The polymerase returns to an open state upon the release of PPi, the post-translocation step, and translocation initiates the next round of reaction. While a closed-complex can form in the absence of divalent catalytic metal ions (e.g., $Mg^{2+}$), the polymerase of the closed complex is proficient in chemical addition of nucleotide in the presence of the divalent metal ions when provided with an appropriate substrate having an available 3'hydroxyl group. Low or deficient levels of catalytic metal ions, such as $Mg^{2+}$, lead to non-covalent (e.g., physical) sequestration of the next correct nucleotide in a closed-complex. This closed-complex may be referred to as a stabilized or trapped closed-complex. In any reaction step described above, the polymerase configuration and/or interaction with a nucleic acid may be monitored during an examination step to identify the next correct base in the template nucleic acid sequence. Before or after incorporation, reaction conditions can be changed to disengage the polymerase from the primed template nucleic acid, and changed again to remove from the local environment any reagents that inhibit polymerase binding.

Generally speaking, the SBB procedure includes an "examination" step that identifies the next template base, and optionally an "incorporation" step that adds one or more complementary nucleotides to the 3'-end of the primer component of the primed template nucleic acid. Identity of the next correct nucleotide to be added is determined either without, or before chemical linkage of that nucleotide to the 3'-end of the primer through a covalent bond. The examination step can involve providing a primed template nucleic acid to be used in the procedure, and contacting the primed template nucleic acid with a polymerase enzyme (e.g., a DNA polymerase) and one or more test nucleotides being investigated as the possible next correct nucleotide. Further, there is a step that involves monitoring or measuring the interaction between the polymerase and the primed template nucleic acid in the presence of the test nucleotides. Optionally, the interaction can take place in the presence of stabilizers, whereby the polymerase-nucleic acid interaction is stabilized in the presence of the next correct nucleotide. Again, the examination step identifies or determines the identity of the next correct nucleotide without requiring incorporation of that nucleotide. Stated differently, identity of the next correct nucleotide can be established without chemical incorporation of the nucleotide into the primer when one or more cycles of examination is carried out using labeled or unlabeled nucleotides.

Whereas methods involving a single template nucleic acid molecule may be described for convenience, these methods are exemplary. The sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified. Thus, such sequencing methods are fully disclosed herein.

The Examination Step

An examination step according to the technique described herein typically includes the following substeps: (1) providing a primed template nucleic acid (i.e., a template nucleic acid molecule hybridized with a primer that optionally may be blocked from extension at its 3'-end); (2) contacting the primed template nucleic acid with a reaction mixture that includes a polymerase and at least one nucleotide; (3) monitoring the interaction of the polymerase with the primed template nucleic acid molecule in the presence of the nucleotide(s) and without chemical incorporation of any nucleotide into the primed template nucleic acid; and (4) identifying the next base in the template nucleic acid (i.e., the next correct nucleotide) using the monitored interaction. Optionally, the primed template nucleic acid molecule can be contacted initially with the polymerase in the absence of nucleotide(s) before contacting any nucleotide. The primer of the primed template nucleic acid can be an extendible primer. Alternatively, the primer of the primed template nucleic acid is blocked from extension at its 3'-end. The primed template nucleic acid, the polymerase and the test nucleotide are capable of forming a ternary complex when the base of the test nucleotide is complementary to the next base of the primed template nucleic acid molecule. Under some conditions the primed template nucleic acid and the polymerase may be capable of forming a binary complex when the base of the test nucleotide is not complementary to the next base of the primed template nucleic acid molecule. Optionally, the contacting occurs under conditions that favor formation of the ternary complex over formation of the binary complex. The identifying step can include identifying the base of the nucleotide that is complementary to the next base of the primed template nucleic acid. Optionally, this includes contacting ternary complexes with one or more wash solutions having different nucleotide compositions that permit ternary complexes to be selectively maintained or dissociated.

All of these steps can be repeated one or more times to obtain extensive sequence information. For example, ternary complexes can be formed initially by contacting a primed template nucleic acid (optionally including a blocked 3'-end) with a polymerase (optionally labeled with an exogenous label) and a plurality of nucleotides (optionally including one or more exogenous labels). Solution conditions can be changed such that ternary complexes are contacted with a wash solution that includes only a subset of nucleotides used for forming the ternary complex. Optionally, this solution includes the same polymerase used to form the ternary complex. Monitoring interaction of the polymerase and/or nucleotide in the ternary complex can be carried out to determine whether the ternary complex remains stable (thereby indicating that one of the nucleotides in the wash buffer corresponds to the cognate nucleotide) or becomes destabilized (thereby indicating that the buffer no longer contains the cognate nucleotide). The wash steps can be repeated until the ternary complex becomes destabilized (e.g., to the point of dissociating) by progressively omitting one nucleotide that was present during the preceding wash cycle. Optionally, a cognate nucleotide can be incorporated following one or a plurality of reagent exchanges.

All of these steps can be repeated one or more times to obtain extensive sequence information. For example, the contacting and monitoring steps can be repeated one or more times. Optionally, the contacting and monitoring steps are repeated using a reaction mixture that includes the polymerase and a first test nucleotide. Optionally, the contacting and monitoring steps are repeated using a reaction mixture that includes the polymerase and a second nucleotide. Optionally, the contacting and monitoring steps are repeated using a reaction mixture that includes the polymerase and a third nucleotide. Optionally, the contacting and monitoring steps are repeated using a reaction mixture that includes the polymerase and a fourth nucleotide.

In the sequencing methods provided herein, the reaction mixture used for forming ternary complexes, that includes the DNA polymerase and at least one test nucleotide, can include at least 1, 2, 3, or 4 types of nucleotide molecules (e.g., either labeled or unlabeled nucleotides). Optionally, the nucleotides are native nucleotides selected from dATP, dTTP, dCTP, and dGTP. Optionally, the reaction mixture includes one or more triphosphate nucleotides and one or more diphosphate nucleotides. Optionally, the polymerase includes a detectable label (e.g., a fluorescent label). Optionally, any fluorescent label joined to a nucleotide or a polymerase is not an intercalating dye, a conformational dye, a FRET partner, or other label that substantially changes fluorescent emission as a consequence of participating in a binary or ternary complex, or participating in binding of nucleotide to polymerase. Optionally, a closed-complex is formed between the primed template nucleic acid, the polymerase, and one of four nucleotide molecules included in the reaction mixture. Localization of detectable label to the position of the primed template nucleic acid (e.g., a "nucleic acid feature" on a solid support, such as a microarray) is detected and used for deducing cognate and/or non-cognate nucleotide identity.

In a particular example of the provided method, the primed template nucleic acid (optionally blocked from extension at its 3'-end) is contacted with a reaction mixture that includes polymerase with one or more nucleotides. A ternary complex will form if one or more of the nucleotides is a cognate nucleotide for the position being interrogated.

In another particular example of the provided method, the primed template nucleic acid (optionally blocked at its 3'-end) is initially contacted with a reaction mixture that includes polymerase without added test nucleotide. Thereafter, the primed template nucleic acid is contacted with a reaction mixture that includes polymerase and one or more test nucleotides that may participate in ternary complex formation. Thereafter, the optionally blocked primed template nucleic acid is contacted with a reaction mixture that includes polymerase and one fewer nucleotide than the preceding reaction mixture. Monitoring maintenance or destabilization of any ternary complex can take place continuously, or after each reaction mixture change.

The examination step may be controlled so that nucleotide incorporation is either attenuated or accomplished. If nucleotide incorporation is attenuated during the examination step, then a separate incorporation step may be performed after determining the identity of the next correct nucleotide. The separate incorporation step may be accomplished without the need for monitoring, as the cognate nucleotide has already been identified during the examination step. If nucleotide incorporation proceeds during examination, subsequent nucleotide incorporation may be attenuated by use of a stabilizer that traps the polymerase on the nucleic acid after incorporation. A reversibly terminated nucleotide may also be used to prevent the addition of subsequent nucleotides. The SBB method allows for controlled determination of a template nucleic acid base without requiring the use of labeled nucleotides, as the interaction between the polymerase and template nucleic acid can be monitored without a label on the nucleotide. To be clear, however, the use of a labeled nucleotide (e.g., a fluorescent nucleotide) is optional when performing the presently disclosed procedure to allow for fluorescent detection of bound nucleotide.

In the sequencing methods provided herein, the test nucleotide (e.g., at least one test nucleotide) can include a 3' hydroxyl group, or a blocking moiety that prevents phosphodiester bond formation at the 3'-end of the primer. A 3' terminator moiety or a 2' terminator moiety may be either a reversible terminator or an irreversible terminator. Optionally, the reversible terminator of the at least one nucleotide molecule is replaced or removed at some point after the examination step that employed the test nucleotide that included the reversible terminator.

Contacting Steps

Contacting of the primed template nucleic acid molecule with reaction mixtures that include the polymerase and one or more test nucleotide molecules can occur under conditions that stabilize formation of the ternary complex and/or destabilize formation of the binary complex. Optionally, the reaction mixture includes potassium glutamate. Optionally, the conditions that stabilize formation of the ternary complex include contacting the primed template nucleic acid with a stabilizing agent. Optionally, the reaction mixture includes a stabilizing agent. The stabilizing agent can be one or more non-catalytic metal ions that inhibit polymerase incorporation. Exemplary non-catalytic metal ions include calcium ion, strontium ion, tin ion, nickel ion, and europium ion. For example, the reaction mixture of the examination step that includes the primed template nucleic acid, the polymerase, and the test nucleotide also may include from 0.01 mM to 30 mM strontium chloride as a stabilizing agent.

Alternatively, and particularly when using a blocked primed template nucleic acid to form a ternary complex in the examination step, reaction mixtures used for conducting examination and monitoring steps optionally can include catalytic metal ions (e.g., $Mg^{2+}$ or $Mn^{2+}$). Concentrations of the catalytic metal ions needed to support polymerization activity when using unmodified (i.e., not 3' blocked) primers will be familiar to those having an ordinary level of skill in the art.

In certain embodiments, the primed template nucleic acid is immobilized to the surface of a solid support. The immobilization may employ either a covalent or a noncovalent bond between one or the other, or even both strands of the primed template nucleic acid and the solid support. For example, when the template and primer strands of the primed template nucleic acid are different molecules, the template strand can be immobilized, for example via its 5'-end. What is necessary, however, is that the 3' terminus of the primer is available for interacting with the polymerase, whether the 3'-end is extendible or blocked from extension by a polymerase.

When the primed template nucleic acid is immobilized to a solid support, there are alternatives for how the contacting steps are performed. For example, the solid support can be physically transferred between different vessels (e.g., individual wells of a multiwell plate) containing different reagent solutions. This is conveniently accomplished using an automated or robotic instrument. In another example, the primed template nucleic acid is immobilized to a solid support inside a flow cell or chamber. In this instance, different contacting steps can be executed by controlled flow of different liquid reagents through the chamber, or across the immobilized primed template nucleic acid.

The Monitoring Step

Monitoring or measuring the interaction of the polymerase with the primed template nucleic acid molecule in the presence of a nucleotide molecule may be accomplished in many different ways. For example, monitoring can include measuring association kinetics for the interaction between the primed template nucleic acid, the polymerase, and a nucleotide. Monitoring the interaction of the polymerase with the primed template nucleic acid molecule in the presence of a nucleotide molecule can include measuring equilibrium binding constants between the polymerase and primed template nucleic acid molecule (i.e., equilibrium binding constants of polymerase to the template nucleic acid in the presence of a nucleotide). Thus, for example, the monitoring includes measuring the equilibrium binding constant of the polymerase to the primed template nucleic acid in the presence of a nucleotide. Monitoring the interaction of the polymerase with the primed template nucleic acid molecule in the presence of a nucleotide molecule includes measuring dissociation kinetics of the polymerase from the primed template nucleic acid in the presence of any one of the four nucleotides. Optionally, monitoring the interaction of the polymerase with the primed template nucleic acid molecule in the presence of a nucleotide molecule includes measuring kinetics of the dissociation of the closed-complex (i.e., dissociation of the primed template nucleic acid, the polymerase, and the nucleotide). Optionally, the measured association kinetics differ depending on the identity of the nucleotide molecule. Optionally, the polymerase has a different affinity for each type of nucleotide employed. Optionally, the polymerase has a different dissociation constant for each type of nucleotide in each type of closed-complex. Association, equilibrium and dissociation kinetics are known and can be readily determined by one in the art. See, for example, Markiewicz et al., *Nucleic Acids Research* 40(16):7975-84 (2012); Xia et al., *J. Am. Chem. Soc.* 135 (1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein in their entireties.

The monitoring step can include monitoring the steady state interaction of the polymerase with the primed template nucleic acid in the presence of a first nucleotide, without chemical incorporation of the first nucleotide into the primer of the primed template nucleic acid. Optionally, monitoring includes monitoring the dissociation of the polymerase from the primed template nucleic acid in the presence of a first nucleotide, without chemical incorporation of the first nucleotide into the primer of the primed template nucleic acid. Optionally, monitoring includes monitoring the association of the polymerase with the primed template nucleic acid in the presence of the first nucleotide, without chemical incorporation of the first nucleotide into the primer of the primed template nucleic acid. Again, test nucleotides in these procedures may be native nucleotides (i.e., unlabeled), labeled nucleotides (e.g., fluorescently labeled nucleotides), or nucleotide analogs (e.g., nucleotides modified to include reversible or irreversible terminator moieties).

In some aspects of the sequencing methods provided herein, a reversibly blocked primer prevents the chemical incorporation of the nucleotide into the primer of the primed template nucleic acid. This stabilizes any ternary complex that may have formed. Optionally, a catalytic metal ion (e.g., magnesium ion) is present in the examination reaction mixture that includes the reversibly blocked primed template nucleic acid molecule.

In other aspects of the sequencing methods provided herein, the absence of a catalytic metal ion in the reaction mixture or the absence of a catalytic metal ion in the active site of the polymerase prevents the chemical incorporation of the nucleotide into the primer of the primed template nucleic acid. Optionally, the chelation of a catalytic metal ion in the reaction mixtures of the contacting step prevents the chemical incorporation of the nucleotide into the primer of the primed template nucleic acid. Optionally, a non-catalytic metal ion acts as a stabilizer for the ternary closed-complex in the presence of the next correct nucleotide. Optionally, the substitution of a catalytic metal ion in the reaction mixtures of the contacting step with a non-catalytic metal ion prevents the chemical incorporation of the nucleotide molecule to the primed template nucleic acid. Optionally, the catalytic metal ion is magnesium. The metal ion mechanisms of polymerases postulates that a low concentration of metal ions may be needed to stabilize the polymerase-nucleotide-DNA binding interaction. See, for instance, Section 27.2.2, Berg J M, Tymoczko J L, Stryer L, *Biochemistry 5th Edition*, WH Freeman Press, 2002.

Optionally, a low concentration of a catalytic ion in the reaction mixtures of the examination step (i.e., that are used for binding polymerase in the presence or absence of a test nucleotide) prevents the chemical incorporation of the test nucleotide into the primer of the primed template nucleic acid. Optionally, a low concentration of the catalytic ion (e.g., magnesium ion) is from about 1 µM to less than 100 µM. Optionally, a low concentration is from about 0.5 µM to about 5 µM. Optionally, the reaction mixtures of the examination step include cobalt, and the incorporating step includes contacting with an incorporation reaction mixture containing a higher concentration of cobalt as compared to the concentration of cobalt in the reaction mixtures of the examination step.

The examination step may be controlled, in part, by providing reaction conditions to prevent chemical incorporation of a nucleotide while allowing monitoring of the interaction between the polymerase and the primed template nucleic acid, thereby permitting determination of the identity of the next base of the nucleic acid template strand. Such reaction conditions may be referred to as "examination reaction conditions." Optionally, a ternary complex or closed-complex is formed under examination conditions. Optionally, a stabilized ternary complex or closed-complex is formed under examination conditions or in a pre-chemistry conformation. Optionally, a stabilized closed-complex is in a pre-translocation conformation, wherein the enclosed nucleotide has been incorporated, but the closed-complex does not allow for the incorporation of a subsequent nucleotide. Optionally, the examination conditions accentuate the difference in affinity for polymerase to primed template nucleic acids in the presence of different nucleotides. Optionally, the examination conditions cause differential affinity of the polymerase to the primed template nucleic acid in the presence of different nucleotides. By way of example, the examination conditions that cause differential affinity of the polymerase to the primed template nucleic acid in the presence of different nucleotides include, but are not limited to, high salt and inclusion of potassium glutamate. Concentrations of potassium glutamate that can be used to alter polymerase affinity for the primed template nucleic acid include 10 mM to 1.6 M of potassium glutamate, or any amount in between 10 mM and 1.6 M. Optionally, high salt refers to a concentration of salt from 50 mM to 1,500 mM salt. Preferably, the salt is a salt providing monovalent cations.

Examination typically involves, in the monitoring step, detecting polymerase interaction with a template nucleic acid, or with template nucleic acid and nucleotide in combination. Detection may include optical, electrical, thermal, acoustic, chemical and mechanical means. Optionally, monitoring is performed after a buffer change or a wash step, wherein the wash step removes any non-bound reagents (e.g., unbound polymerases and/or nucleotides) from the region of observation. Optionally, monitoring is performed during a buffer change or a wash step, such that the dissociation kinetics of the polymerase-nucleic acid or polymerase-nucleic acid-nucleotide complexes may be used to determine the identity of the next base. Optionally, monitoring is performed during the course of addition of the examination reaction mixture or first reaction mixture, such that the association kinetics of the polymerase to the nucleic acid may be used to determine the identity of the next base on the nucleic acid. Optionally, monitoring involves distinguishing closed-complexes from binary complexes of polymerase and primed template nucleic acid. Optionally, monitoring is performed under equilibrium conditions where the affinities measured are equilibrium affinities. Multiple examination steps including different or similar examination reagents, may be performed sequentially to ascertain the identity of the next template base. Multiple examination steps may be utilized in cases where multiple template nucleic acids are being sequenced simultaneously in one sequencing reaction, wherein different nucleic acids react differently to the different examination reagents. Optionally, multiple examination steps may improve the accuracy of next base determination.

In an exemplary sequencing reaction, the examination step includes formation and/or stabilization of a closed-complex including a polymerase, a primed template nucleic acid, and the next correct nucleotide. Characteristics of the formation and/or release of the closed-complex are monitored to identify the enclosed nucleotide and therefore the next base in the template nucleic acid. Closed-complex characteristics can be dependent on the sequencing reaction components (e.g., polymerase, primer, template nucleic acid, nucleotide) and/or reaction mixture components and/or conditions. Optionally, the closed-complex is in a pre-chemistry conformation. Optionally, the closed-complex is in a pre-translocation conformation. Optionally, the closed-complex is in a post-translocation conformation.

The examination step involves monitoring the interaction of a polymerase with a primed template nucleic acid in the presence of a test nucleotide. In some embodiments, this can involve monitoring the interaction of a detectably labeled polymerase with the primed template nucleic acid. In other embodiments, this can involve monitoring a detectable signal (e.g., a fluorescent emission) produced by a detectably labeled test nucleotide. In still other embodiments, the system is a label-free system based on monitoring binding of unlabeled polymerase to a surface (e.g., using surface plasmon resonance sensing, or interferometry). The formation of a closed-complex may be monitored. Optionally, the absence of formation of a closed-complex is monitored. Optionally, the dissociation of a closed-complex is monitored. Optionally, the incorporation step involves monitoring incorporation of a nucleotide. Optionally, the incorporation step involves monitoring the absence of nucleotide incorporation.

Any process of the examination and/or incorporation step may be monitored. Optionally, a polymerase has an exogenous label or "tag." Optionally, the detectable tag or label on the polymerase is removable. Optionally, the nucleotide harbors a detectable label (e.g., a covalently attached fluorescent label). Optionally, the nucleotides or polymerases have a detectable label, however, the label is not detected during sequencing. Optionally, no component of the sequencing reaction is detectably labeled with an exogenous label.

Monitoring the variation in affinity of a polymerase for a template nucleic acid in the presence of correct and incorrect nucleotides, under conditions that may or may not allow the incorporation of the nucleotide, may be used to determine the sequence of the nucleic acid. The affinity of a polymerase for a template nucleic acid in the presence of different nucleotides, including modified or labeled nucleotides, can be monitored as the off-rate of the polymerase-nucleic acid interaction in the presence of the various nucleotides. The affinities and off-rates of many standard polymerases to various matched/correct, mismatched/incorrect and modified nucleotides are known in the art. Single molecule imaging of Klenow polymerase reveals that the off-rate for a template nucleic acid for different nucleotide types, where the nucleotide types are prevented from incorporating, are distinctly and measurably different.

Optionally, a nucleotide of a particular type is made available to a polymerase in the presence of a primed template nucleic acid. The reaction is monitored, wherein, if the nucleotide is a next correct nucleotide, the polymerase may be stabilized to form a closed-complex. If the nucleotide is an incorrect nucleotide, a closed-complex may still be formed; however, without the additional assistance of stabilizing agents or reaction conditions (e.g., absence of catalytic ions, polymerase inhibitors, salt), the closed-complex may dissociate. The rate of dissociation is dependent on the affinity of the particular combination of polymerase, template nucleic acid, and nucleotide, as well as reaction conditions. Optionally, the affinity is measured as an off-rate. Optionally, the affinity is different between different nucleotides for the closed-complex. For example, if the next base in the template nucleic acid downstream of the 3'-end of the primer is G, the polymerase-nucleic acid affinity, measured as an off-rate, is expected to be different based on whether dATP, dCTP, dGTP or dTTP are added. In this case, dCTP would have the slowest off-rate, with the other nucleotides providing different off-rates for the interaction. Optionally, the off-rate may be different depending on the reaction conditions, for example, the presence of stabilizing agents (e.g., absence of magnesium or inhibitory compounds) or reaction conditions (e.g., nucleotide modifications or modified polymerases). Once the identity of the next correct nucleotide is determined, 1, 2, 3, 4 or more nucleotide types may be introduced simultaneously to the reaction mixture under conditions that specifically target the formation of a closed-complex. Excess nucleotides may be removed from the reaction mixture and the reaction conditions modulated to incorporate the next correct nucleotide of the closed-complex. This sequencing reaction ensures that only one nucleotide is incorporated per sequencing cycle.

The affinity of a polymerase for a template nucleic acid in the presence of a nucleotide can be measured in a plurality of methods known to one of skill in the art. Optionally, the affinity is measured as an off-rate, where the off-rate is measured by monitoring the release of the polymerase from the template nucleic acid as the reaction is washed by a wash buffer. Optionally, the affinity is measured as an off-rate, where the off-rate is measured by monitoring the release of the polymerase from the template nucleic acid under equilibrium binding conditions, especially equilibrium binding conditions in which the polymerase binding rates are low or diffusion limited. The polymerase binding rates may be diffusion limited at sufficiently low concentrations of polymerase, wherein if the polymerase falls off from the DNA-polymerase complex, it does not load back immediately, thereby allowing for sufficient time to detect that the polymerase has been released from the complex. For a higher affinity interaction, the polymerase is released from the nucleic acid slowly, whereas a low affinity interaction results in the polymerase being released more rapidly. The spectrum of affinities, in this case, translates to different off-rates, with the off-rates measured under dynamic wash conditions or at equilibrium. The smallest off-rate corresponds to the base complementary to the added nucleotide, while the other off-rates vary, in a known fashion, depending on the combination of polymerase and nucleotide selected.

Optionally, the off-rate is measured as an equilibrium signal intensity after the polymerase and nucleotide are provided in the reaction mixture, wherein the interaction with the lowest off-rate (highest affinity) nucleotide produces the strongest signal, while the interactions with other, varying, off-rate nucleotides produce signals of measurably different intensities. As a non-limiting example, a fluorescently labeled polymerase, measured, preferably, under total internal reflection (TIRF) conditions, produces different measured fluorescence intensities depending on the number of polymerase molecules bound to surface-immobilized nucleic acid molecules in a suitably chosen window of time. The intrinsic fluorescence of the polymerase, for instance, tryptophan fluorescence, may also be utilized. A high off-rate interaction produces low measured intensities, as the number of bound polymerase molecules, in the chosen time window is very small, wherein a high off-rate indicates that most of the polymerase is unbound from the nucleic acid.

Any surface localized measurement scheme may be employed including, but not limited to, labeled or fluorescence schemes. Suitable measurement schemes that measure affinities under equilibrium conditions include, but are not limited to, bound mass, refractive index, surface charge, dielectric constant, and other schemes known in the art. Optionally, a combination of on-rate and off-rate engineering yields higher fidelity detection in the proposed schemes. As a non-limiting example, a uniformly low on-rate, base-dependent, varying off-rate results in an unbound polymerase remaining unbound for prolonged periods, allowing enhanced discrimination of the variation in off-rate and measured intensity. The on-rate may be manipulated by lowering the concentration of the added polymerase, nucleotide, or both polymerase and nucleotide.

Optionally, the interaction between the polymerase and the nucleic acid is monitored via a detectable tag attached to the polymerase. The tag may be monitored by detection methods including, but limited to, optical, electrical, thermal, mass, size, charge, vibration, and pressure. The label may be magnetic, fluorescent or charged. For external and internal label schemes, fluorescence anisotropy may be used to determine the stable binding of a polymerase to a nucleic acid in a closed-complex.

By way of example, a polymerase is tagged with a fluorophore, wherein closed-complex formation is monitored as a stable fluorescent signal. The unstable interaction of the polymerase with the template nucleic acid in the presence of an incorrect nucleotide results in a measurably weaker signal compared to the closed-complex formed in the presence of the next correct nucleotide. In certain preferred embodiments, however, the sequencing-by-binding procedure does not rely on detection of any exogenous label (e.g., a fluorescent label) joined to the polymerase. For example, the polymerase can be a native polymerase.

Optionally, a primed template nucleic acid molecule (optionally blocked at its 3'-end) is contacted with polymerase and one or more exogenously labeled nucleotides during the examination step. Monitoring of signal generated as a consequence of the presence of the labeled nucleotide provides information concerning formation and stabilization/destabilization of the ternary complex that includes the labeled nucleotide. For example, if the exogenous label is a fluorescent label, and if the primed template nucleic acid is immobilized to a solid support at a particular locus, then monitoring fluorescent signal associated with that locus can be used for monitoring ternary complex formation and stability under different reaction mixture conditions.

The Identifying Step

The identity of the next correct base or nucleotide can be determined by monitoring the presence, formation and/or dissociation of the ternary complex or closed-complex. The identity of the next base may be determined without chemically incorporating the next correct nucleotide into the 3'-end of the primer. Optionally, the identity of the next base is determined by monitoring the affinity of the polymerase for the primed template nucleic acid in the presence of added nucleotides. Optionally, the affinity of the polymerase for the primed template nucleic acid in the presence of the next correct nucleotide may be used to determine the next correct base on the template nucleic acid. Optionally, the affinity of the polymerase for the primed template nucleic acid in the presence of an incorrect nucleotide may be used to determine the next correct base on the template nucleic acid.

In certain embodiments, a ternary complex that includes a primed template nucleic acid (or a blocked primed template nucleic acid) is formed in the presence of a polymerase and a plurality of nucleotides. Cognate nucleotide participating in the ternary complex optionally is identified by observing destabilization of the complex that occurs when the cognate nucleotide is absent from the reaction mixture. This is conveniently carried out, for example, by exchanging one reaction mixture for another. Here, loss of the complex is an indicator of cognate nucleotide identity. Loss of binding signal (e.g., a fluorescent binding signal associated with a particular locus on a solid support) can occur when the primed template nucleic acid is exposed to a reaction mixture that does not include the cognate nucleotide. Optionally, maintenance of a ternary complex in the presence of a single nucleotide in a reaction mixture also can indicate identity of the cognate nucleotide.

The Incorporation Step

Optionally, the methods provided herein further include an incorporation step. By way of example, the incorporation step includes incorporating a single nucleotide (e.g., an unlabeled nucleotide, a reversible terminator nucleotide, or a detectably labeled nucleotide analog) complementary to the next base of the template nucleic acid into the primer of the primed template nucleic acid molecule. Optionally, the incorporation step includes contacting the primed template nucleic acid molecule, polymerase and nucleotide with an incorporation reaction mixture. The incorporation reaction mixture, typically includes a catalytic metal ion.

The provided method may further include preparing the primed template nucleic acid molecule for a next examination step after the incorporation step. Optionally, the preparing includes subjecting the primed template nucleic acid or the nucleic acid/polymerase complex to one or more wash steps; a temperature change; a mechanical vibration; a pH change; salt or buffer composition changes, an optical stimulation or a combination thereof. Optionally, the wash step includes contacting the primed template nucleic acid or the primed template nucleic acid/polymerase complex with one or more buffers, detergents, protein denaturants, proteases, oxidizing agents, reducing agents, or other agents capable of releasing internal crosslinks within a polymerase or crosslinks between a polymerase and nucleic acid.

Optionally, the method further includes repeating the examination step and the incorporation step to sequence a template nucleic acid molecule. The examination step may be repeated one or more times prior to performing the incorporation step. Optionally, two consecutive examination steps include reaction mixtures with different nucleotide molecules (e.g., different nucleotides that are labeled or unlabeled). Optionally, prior to incorporating the single nucleotide into the primed template nucleic acid molecule, the first reaction mixture is replaced with a second reaction mixture including a polymerase and 1, 2, 3, or 4 types of nucleotide molecules (e.g., different unlabeled nucleotides). Optionally, the nucleotide molecules are native nucleotides selected from dATP, dTTP, dCTP, and dGTP.

The incorporation reaction may be enabled by an incorporation reaction mixture. Optionally, the incorporation reaction mixture includes a different composition of nucleotides than the examination reaction. For example, the examination reaction includes one type of nucleotide and the incorporation reaction includes another type of nucleotide. By way of another example, the examination reaction includes one type of nucleotide and the incorporation reaction includes four types of nucleotides, or vice versa. Optionally, the examination reaction mixture is altered or replaced by the incorporation reaction mixture. Optionally, the incorporation reaction mixture includes a catalytic metal ion, potassium chloride, or a combination thereof.

Nucleotides present in the reaction mixture but not sequestered in a closed-complex may cause multiple nucleotide insertions. Thus, a wash step can be employed prior to the chemical incorporation step to ensure only the nucleotide sequestered within a trapped closed-complex is available for incorporation during the incorporation step. Optionally, free nucleotides may be removed by enzymes such as phosphatases. The trapped polymerase complex may be a closed-complex, a stabilized closed-complex or ternary complex involving the polymerase, primed template nucleic acid and next correct nucleotide.

Optionally, the nucleotide enclosed within the closed-complex of the examination step is incorporated into the 3'-end of the template nucleic acid primer during the incorporation step. Optionally, the nucleotide enclosed within the closed-complex of the examination step is incorporated during the examination step, but the closed-complex does not allow for the incorporation of a subsequent nucleotide; in this instance, the closed-complex is released during an incorporation step, allowing for a subsequent nucleotide to become incorporated.

Optionally, the incorporation step includes replacing a nucleotide from the examination step and incorporating another nucleotide into the 3'-end of the template nucleic acid primer. The incorporation step can further involve releasing a nucleotide from within a closed-complex (e.g., the nucleotide is a modified nucleotide or nucleotide analog) and incorporating a nucleotide of a different kind to the 3'-end of the template nucleic acid primer. Optionally, the released nucleotide is removed and replaced with an incorporation reaction mixture including a next correct nucleotide.

Suitable reaction conditions for incorporation may involve replacing the examination reaction mixture with an incorporation reaction mixture. Optionally, nucleotides present in the examination reaction mixture are replaced with one or more nucleotides in the incorporation reaction mixture. Optionally, the polymerase present during the examination step is replaced during the incorporation step. Optionally, the polymerase present during the examination step is modified during the incorporation step. Optionally, the one or more nucleotides present during the examination step are modified during the incorporation step. The reaction mixture and/or reaction conditions present during the examination step may be altered by any means during the incorporation step. These means include, but are not limited to, removing reagents, chelating reagents, diluting reagents, adding reagents, altering reaction conditions such as conductivity or pH, and any combination thereof. The reagents in the reaction mixture including any combination of polymerase, primed template nucleic acid, and nucleotide may be modified during the examination step and/or incorporation step.

Optionally, the reaction mixture of the incorporation step includes competitive inhibitors, wherein the competitive inhibitors reduce the occurrence of multiple incorporations. In certain embodiments, the competitive inhibitor is a non-incorporable nucleotide. In certain embodiments, the competitive inhibitor is an aminoglycoside. The competitive inhibitor is capable of replacing either the nucleotide or the catalytic metal ion in the active site, such that after the first incorporation the competitive inhibitor occupies the active site preventing a second incorporation. In some embodiments, both an incorporable nucleotide and a competitive inhibitor are introduced in the incorporation step, such that the ratio of the incorporable nucleotide and the inhibitor can be adjusted to ensure incorporation of a single nucleotide at the 3'-end of the primer.

Optionally, the provided reaction mixtures, including the incorporation reaction mixtures, include at least one unlabeled nucleotide molecule that is a non-incorporable nucleotide. In other words, the provided reaction mixtures can include one or more unlabeled nucleotide molecules that are incapable of incorporation into the primer of the primed template nucleic acid molecule. Nucleotides incapable of incorporation include, for example, diphosphate nucleotides. For instance, the nucleotide may contain modifications to the triphosphate group that make the nucleotide non-incorporable. Examples of non-incorporable nucleotides may be found in U.S. Pat. No. 7,482,120, the disclosure of which is incorporated by reference herein in its entirety. Optionally, the primer may not contain a free hydroxyl group at its 3'-end, thereby rendering the primer incapable of incorporating any nucleotide, and, thus making any nucleotide non-incorporable.

A polymerase inhibitor optionally may be included with the reaction mixtures containing test nucleotides in the examination step to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor is a DNA or an RNA aptamer. Optionally, the polymerase inhibitor competes with a catalytic-ion binding site in the polymerase. Optionally, the polymerase inhibitor is a reverse transcriptase inhibitor. The polymerase inhibitor may be an HIV-1 reverse transcriptase inhibitor or an HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

In the provided sequencing methods, the next correct nucleotide is identified before the incorporation step, allowing the incorporation step to not require labeled reagents and/or monitoring. Thus, in the provided methods, a nucleotide, optionally, does not contain an attached detectable tag or label. Optionally, the nucleotide contains a detectable label, but the label is not detected in the method. Optionally, the correct nucleotide does not contain a detectable label; however, an incorrect or non-complementary nucleotide to the next base contains a detectable label.

The examination step of the sequencing reaction may be repeated 1, 2, 3, 4 or more times prior to the incorporation step. The examination and incorporation steps may be repeated until the desired sequence of the template nucleic acid is obtained.

The formation of the closed-complex or the stabilized closed-complex can be employed to ensure that only one nucleotide is added to the template nucleic acid primer per cycle of sequencing, wherein the added nucleotide is sequestered within the closed-complex. The controlled incorporation of a single nucleotide per sequencing cycle enhances sequencing accuracy for nucleic acid regions including homopolymer repeats. Optionally, only reversible terminator nucleotides are incorporated into an extendible primer by the action of a polymerase over the course of several cognate nucleotide identification cycles. The reversible terminator nucleotides can be unlabeled reversible terminator nucleotides (e.g., having 3'-$ONH_2$ reversible terminator moieties)

Reaction Mixtures

Nucleic acid sequencing reaction mixtures, or simply "reaction mixtures," typically include reagents that are commonly present in polymerase-based nucleic acid synthesis reactions.

Reaction mixture reagents include, but are not limited to, enzymes (e.g., the polymerase), dNTPs, template nucleic acids, primer nucleic acids, salts, buffers, small molecules, co-factors, metals, and ions. The ions may be catalytic ions, divalent catalytic ions, non-catalytic ions, non-covalent metal ions, or a combination thereof. The reaction mixture can include salts such as NaCl, KCl, potassium acetate, ammonium acetate, potassium glutamate, $NH_4Cl$, or $NH_4HSO_4$. The reaction mixture can include a source of ions, such as $Mg^{2+}$ or $Mn^{2+}$ Mg-acetate, $Co^{2+}$ or $Ba^{2+}$. The reaction mixture can include tin ions, $Ca^{2+}$, $Zn^{2+}$, $Cu^{2+}$, $Co^{2+}$, $Fe^{2+}$, $Ni^{2+}$, or $Eu^{2+}$. The buffer can include Tris, Tricine, HEPES, MOPS, ACES, MES, phosphate-based buffers, and acetate-based buffers. The reaction mixture can include chelating agents such as EDTA, EGTA, and the like. Optionally, the reaction mixture includes cross-linking reagents. Provided herein are reaction mixtures, optionally, used during the examination step, as well as incorporation reaction mixtures used during nucleotide incorporation that can include one or more of the aforementioned agents. Reaction mixtures, when used during examination, can be referred to herein as examination reaction mixtures. Optionally, the examination reaction mixture includes a high concentration of salt (e.g., a salt providing monovalent cations); a high pH; 1, 2, 3, 4, or more types of unlabeled nucleotides; potassium glutamate; a chelating agent; a polymerase inhibitor; a catalytic metal ion; a non-catalytic metal ion; or any combination thereof. The examination reaction mixture can include 10 mM to 1.6 M of potassium glutamate or any amount in between 10 mM and 1.6 M. Optionally, the incorporation reaction mixture includes a catalytic metal ion; 1, 2, 3, 4, or more types of nucleotides (e.g., unlabeled nucleotides); potassium chloride; a non-catalytic metal ion; or any combination thereof.

Optionally, reaction mixtures in accordance with the disclosed techniques modulate the formation and stabilization of a closed-complex during an examination step. For example, the reaction conditions of the examination step optionally can favor the formation and/or stabilization of a closed-complex encapsulating a nucleotide, and hinder the formation and/or stabilization of a binary complex. The binary interaction between the polymerase and template nucleic acid may be manipulated by modulating sequencing reaction parameters such as ionic strength, pH, temperature, or any combination thereof, or by the addition of a binary complex destabilizing agent to the reaction. Optionally, high salt (e.g., 50 mM to 1,500 mM) and/or pH changes are utilized to destabilize a binary complex. Optionally, the salt used for providing the high salt conditions is a salt that provides monovalent cations. Optionally, a binary complex may form between a polymerase and a template nucleic acid during the examination or incorporation step of the sequencing reaction, regardless of the presence of a nucleotide. Optionally, the reaction conditions favor the stabilization of a closed ternary complex and destabilization of a binary complex. By way of example, the pH of the examination reaction mixture can be adjusted from pH 4.0 to pH 10.0 to favor the stabilization of a closed ternary complex and destabilization of a binary complex. Optionally, the pH of the examination reaction mixture is from pH 4.0 to pH 6.0. Optionally, the pH of the examination reaction mixture is pH 6.0 to pH 10.0.

The provided reaction mixtures and sequencing methods disclosed herein encourage polymerase interaction with the nucleotides and template nucleic acid in a manner that reveals the identity of the next base while controlling the chemical addition of a nucleotide. Optionally, the methods are performed in the absence of detectably labeled nucleotides or in the presence of labeled nucleotides wherein the labels are not detected. Optionally, the reaction mixtures include nucleotides that harbor an exogenous detectable label (e.g., a fluorescent label). Optionally, a plurality of nucleotides in a reaction mixture harbor the same exogenous detectable label. Optionally, a plurality of nucleotides in a reaction mixture harbor different exogenous detectable labels. Optionally, the reaction mixtures can include one or more exogenously labeled polymerase enzymes.

Provided herein are reaction mixtures and methods that facilitate formation and/or stabilization of a closed-complex that includes a polymerase bound to a primed template nucleic acid and a nucleotide enclosed within the polymerase-template nucleic acid complex, under examination reaction mixture conditions. Examination reaction conditions may inhibit or attenuate nucleotide incorporation. Optionally, incorporation of the enclosed nucleotide is inhibited and the complex is stabilized or trapped in a pre-chemistry conformation or a ternary complex. Optionally, the enclosed nucleotide is incorporated and subsequent nucleotide incorporation is inhibited. In this instance, the complex is stabilized or trapped in a pre-translocation conformation. For the sequencing reactions provided herein, the closed-complex is stabilized during the examination step, allowing for controlled nucleotide incorporation. Optionally, a stabilized closed-complex is a complex wherein incorporation of an enclosed nucleotide is attenuated, either transiently (e.g., to examine the complex and then incorporate the nucleotide) or permanently (e.g., for examination only) during an examination step. Optionally, a stabilized closed-complex allows for the incorporation of the enclosed nucleotide, but does not allow for the incorporation of a subsequent nucleotide. Optionally, the closed-complex is stabilized in order to monitor any polymerase interaction with a template nucleic acid in the presence of a nucleotide for identification of the next base in the template nucleic acid.

Optionally, the enclosed nucleotide has severely reduced or disabled binding to the template nucleic acid in the closed-complex. Optionally, the enclosed nucleotide is base-paired to the template nucleic acid at a next base. Optionally, the identity of the polymerase, nucleotide, primer, template nucleic acid, or any combination thereof, affects the interaction between the enclosed nucleotide and the template nucleic acid in the closed-complex.

Optionally, the enclosed nucleotide is bound to the polymerase of the closed-complex. Optionally, the enclosed nucleotide is weakly associated with the polymerase of the closed-complex. Optionally, the identity of the polymerase, nucleotide, primer, template nucleic acid, or any combination thereof, affects the interaction between the enclosed nucleotide and the polymerase in the closed-complex. For a given polymerase, each nucleotide has a different affinity for the polymerase than another nucleotide. Optionally, this affinity is dependent, in part, on the template nucleic acid and/or the primer.

The closed-complex may be transiently formed. Optionally, the enclosed nucleotide is a next correct nucleotide. In some methods, the presence of the next correct nucleotide contributes, in part, to the stabilization of a closed-complex. Optionally, the enclosed nucleotide is not a next correct nucleotide.

Optionally, the examination reaction condition comprises a plurality of primed template nucleic acids, polymerases, nucleotides, or any combination thereof. Optionally, the plurality of nucleotides comprises 1, 2, 3, 4, or more types of different nucleotides, for example dATP, dTTP, dGTP, and dCTP. Optionally, the plurality of template nucleic acids is a clonal population of template nucleic acids.

Reaction conditions that may modulate the stability of a closed-complex include, but are not limited to, the availability of catalytic metal ions, suboptimal or inhibitory metal ions, ionic strength, pH, temperature, polymerase inhibitors, cross-linking reagents, the presence or absence of a reversible terminator moiety on the 3' nucleotide of the primed template nucleic acid molecule, and any combination thereof. Reaction reagents which may modulate the stability of a closed-complex include, but are not limited to, non-incorporable nucleotides, incorrect nucleotides, nucleotide analogs, modified polymerases, template nucleic acids with non-extendible polymerization initiation sites, and any combination thereof.

The examination reaction mixture can include other molecules including, but not limited to, enzymes. Optionally, the examination reaction mixture includes any reagents or biomolecules generally present in a nucleic acid polymerization reaction. Reaction components may include, but are not limited to, salts, buffers, small molecules, metals, and ions. Optionally, salts used in the examination reaction mixture include salts that provide monovalent cations. Optionally, properties of the reaction mixture may be manipulated, for example, electrically, magnetically, and/or with vibration.

Nucleotides and Nucleotide Analogs

Nucleotides useful for carrying out the sequencing-by-binding procedures described herein include native nucleotides, labeled nucleotides (e.g., nucleotides that include an exogenous fluorescent dye or other label not found in native nucleotides), and nucleotide analogs (e.g., nucleotides having a reversible terminator moiety).

There is flexibility in the nature of the nucleotides that may be employed in connection with the presently described technique. A nucleotide may include as its nitrogenous base any of: adenine, cytosine, guanine, thymine, or uracil. Optionally, a nucleotide includes inosine, xanthanine, hypoxanthanine, isocytosine, isoguanine, nitropyrrole (including 3-nitropyrrole) or nitroindole (including 5-nitroindole) base. Useful nucleotides include, but are not limited to, ATP, UTP, CTP, GTP, ADP, UDP, CDP, GDP, AMP, UMP, CMP, GMP, dATP, dTTP, dCTP, dGTP, dUTP, dADP, dTDP, dCDP, dGDP, dUDP, dAMP, dTMP, dCMP, dGMP, and dUMP. Optionally, the phosphate group is modified with a moiety. The moiety may include a detectable label. Optionally, the 3' OH group of the nucleotide is modified with a moiety, where the moiety may be a 3' reversible or irreversible terminator moiety. Optionally, the 2' position of the nucleotide is modified with a moiety, where the moiety may be a 2' reversible or irreversible terminator moiety. Optionally, the base of the nucleotide is modified to include a detectable label (e.g., a detectable moiety). Optionally, the base of the nucleotide is modified to include a reversible terminator moiety. Nucleotides may also contain terminating inhibitors of DNA polymerase, dideoxynucleotides or 2',3' dideoxynucleotides, which are abbreviated as ddNTPs (ddGTP, ddATP, ddTTP, ddCTP, and ddUTP).

Optionally, a closed-complex of an examination step includes a nucleotide analog or modified nucleotide to facilitate stabilization of the closed-complex. Optionally, a nucleotide analog includes a nitrogenous base, five-carbon sugar, and phosphate group and any component of the nucleotide may be modified and/or replaced. Nucleotide analogs may be non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

Nucleotide analogs can include terminators that reversibly prevent nucleotide incorporation to the 3'-end of the primer. One type of reversible terminator is a 3'-O-blocked reversible terminator. The terminator is linked to the oxygen atom of the 3' OH end of the 5-carbon sugar of a nucleotide. Another type of reversible terminator is a 3'-unblocked reversible terminator. The terminator is linked to the nitrogenous base of a nucleotide. For reviews of nucleotide analogs having terminators, see, e.g., Mu, R., et al., "The History and Advances of Reversible Terminators Used in New Generations of Sequencing Technology," Genomics, Proteomics & Bioinformatics 11(1):34-40 (2013), which is incorporated by reference herein in its entirety.

Optionally, nucleotides are substituted for modified nucleotide analogs having terminators that irreversibly prevent nucleotide incorporation to the 3'-end of the primer. Irreversible nucleotide analogs include dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides include a blocking moiety that inhibits or prevents the nucleotide from forming a covalent linkage to a second nucleotide (3' OH of a primer) during the incorporation step of a nucleic acid polymerization reaction. The blocking moiety can be removed from the nucleotide, allowing for nucleotide incorporation.

Optionally, a nucleotide analog present in a closed-complex renders the closed-complex stable. Optionally, the nucleotide analog is non-incorporable. Optionally, the nucleotide analog is released and a native nucleotide is incorporated. Optionally, the closed-complex is released, the nucleotide analog is modified, and the modified nucleotide analog is incorporated. Optionally, the closed-complex is released under reaction conditions that modify and/or destabilize the nucleotide analog in the closed-complex.

Optionally, a nucleotide analog present in a closed-complex is incorporated and the closed-complex is stabilized. The closed-complex may be stabilized by the nucleotide analog, or for example, by any stabilizing methods disclosed herein. Optionally, the nucleotide analog does not allow for the incorporation of a subsequent nucleotide. The closed-complex can be released, for example, by any methods described herein, and the nucleotide analog is modified. The modified nucleotide analog may allow for subsequent incorporation of a nucleotide to its 3'-end.

Optionally, a nucleotide analog is present in the reaction mixture during the examination step. For example, 1, 2, 3, 4 or more nucleotide analogs are present in the reaction mixture during the examination step. Optionally, a nucleotide analog is replaced, diluted, or sequestered during an incorporation step. Optionally, a nucleotide analog is replaced with a native nucleotide. The native nucleotide may include a next correct nucleotide. Optionally, a nucleotide analog is modified during an incorporation step. The modified nucleotide analog can be similar to or the same as a native nucleotide.

Optionally, a nucleotide analog has a different binding affinity for a polymerase than a native nucleotide. Optionally, a nucleotide analog has a different interaction with a next base than a native nucleotide. Nucleotide analogs and/or non-incorporable nucleotides may base-pair with a complementary base of a template nucleic acid.

Optionally, a nucleotide analog is a nucleotide, modified or native, fused to a polymerase. Optionally, a plurality of nucleotide analogs includes fusions to a plurality of polymerases, wherein each nucleotide analog includes a different polymerase.

A nucleotide can be modified to favor the formation of a closed-complex over the formation of a binary complex. A nucleotide may be selected or modified to have a high affinity for a polymerase, wherein the polymerase binds to a nucleotide prior to binding to the template nucleic acid.

Any nucleotide modification that traps the polymerase in a closed-complex may be used in the methods disclosed herein. The nucleotide may be trapped permanently or transiently. Optionally, the nucleotide analog is not the means by which a closed-complex is stabilized. Any closed-complex stabilization method may be combined in a reaction utilizing a nucleotide analog.

Optionally, a nucleotide analog that allows for the stabilization of a closed-complex is combined with reaction conditions that usually release the closed-complex. The conditions include, but are not limited to, the presence of a release reagent (e.g., catalytic metal ion, such as magnesium or manganese). Optionally, the closed-complex is stabilized even in the presence of a catalytic metal ion. Optionally, the closed-complex is released even in the presence of a nucleotide analog. Optionally, the stabilization of the closed-complex is dependent, in part, on the concentrations and/or identity of the stabilization reagent and/or release reagents, and any combination thereof. Optionally, stabilization of a closed-complex containing nucleotide analogs is combined with additional reaction conditions that function to stabilize a closed-complex, including, but not limited to, sequestering, removing, reducing, omitting, and/or chelating a catalytic metal ion; the presence of a polymerase inhibitor, cross-linking agent; and any combination thereof.

Optionally, one or more nucleotides can be labeled with distinguishing and/or detectable tags or labels; however, such tags or labels are not detected during examination, identification of the base or incorporation of the base, and are not detected during the sequencing methods disclosed herein. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase position of the nucleotide. Under suitable reaction conditions, the tagged nucleotides may be enclosed in a closed-complex with the polymerase and the primed template nucleic acid. Alternatively, a tag is attached to the gamma phosphate position of the nucleotide.

Optionally, the labeled nucleotide can include 3-10 or more phosphate groups. Optionally, the labeled nucleotide can be any of adenosine, guanosine, cytidine, thymidine or uridine, or any other type of labeled nucleotide. Optionally, the label can be an energy transfer acceptor reporter moiety. Optionally, the label can be a fluorescent dye. Optionally, the polymerase can be contacted with more than one type of labeled nucleotide (e.g., A, G, C, and/or T/U, or others). Optionally, each type of labeled nucleotide can be operably linked to a different reporter moiety to permit nucleotide identification. Optionally, each type of labeled nucleotide can be operably linked to the same type of reporter moiety. Optionally, the labeled nucleotides are operably linked at the terminal phosphate group with a reporter moiety. Optionally, the labeled nucleotides are operably linked at the base moiety with a reporter moiety. Optionally, the labeled nucleotide can be a non-incorporable nucleotide. Optionally, the non-incorporable nucleotide can bind to the polymerase and primed template nucleic acid molecule in a template-dependent manner, but does not incorporate. Optionally, different types of labeled nucleotides can be employed in the method for detecting the presence of a transiently-bound nucleotide in order to determine the frequency, duration, or intensity, of a transiently-bound nucleotide. For example, a comparison can be made between the frequency/duration/intensity of transiently-bound complementary and non-complementary nucleotides. Under circumstances involving direct excitation of the reporter moiety, the length of the transient binding time of a complementary nucleotide can be longer and/or more frequent compared to that of a non-complementary nucleotide.

Polymerases

Polymerases useful for carrying out the disclosed sequencing-by-binding technique include naturally occurring polymerases and modified variants thereof, including, but not limited to, mutants, recombinants, fusions, genetic modifications, chemical modifications, synthetics, and analogs. Naturally occurring polymerases and modified variants thereof are not limited to polymerases that retain the ability to catalyze a polymerization reaction. Optionally, the naturally occurring and/or modified variations thereof retain the ability to catalyze a polymerization reaction. Optionally, the naturally occurring and/or modified variations have special properties that enhance their ability to sequence DNA, including enhanced binding affinity to nucleic acids, reduced binding affinity to nucleic acids, enhanced catalysis rates, reduced catalysis rates etc. Mutant polymerases include polymerases wherein one or more amino acids are replaced with other amino acids (naturally or non-naturally occurring), and insertions or deletions of one or more amino acids. Modified polymerases include polymerases that contain an external tag, which can be used to monitor the presence and interactions of the polymerase. Optionally, intrinsic signals from the polymerase can be used to monitor their presence and interactions. Thus, the provided methods can include monitoring the interaction of the polymerase, nucleotide and template nucleic acid through detection of an intrinsic signal from the polymerase. Optionally, the intrinsic signal is a light scattering signal. For example, intrinsic signals include native fluorescence of certain amino acids such as tryptophan, wherein changes in intrinsic signals from the polymerase may indicate the formation of a closed-complex.

Thus, in the provided methods, the polymerase is an unlabeled polymerase and monitoring is performed in the absence of a detectable label associated with the polymerase. Some modified polymerases or naturally occurring polymerases, under specific reaction conditions, may incorporate only single nucleotides and may remain bound to the primer-template after the incorporation of the single nucleotide. Optionally, the thumb and finger domains of the polymerase may form transient or covalent crosslinks due to their physical proximity in the closed form of the polymerase. The crosslinks may be formed, for example by native or engineered cysteines at suitable positions on the thumb and finger domains.

The term polymerase and its variants, as used herein, also refers to fusion proteins including at least two portions linked to each other, for example, where one portion includes a peptide that can catalyze the polymerization of nucleotides into a nucleic acid strand is linked to another portion that includes a second moiety, such as, a reporter enzyme or a processivity-modifying domain. For example, T7 DNA polymerase includes a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. Although DNA polymerases differ in detail, they have a similar overall shape of a hand with specific regions referred to as the fingers, the palm, and the thumb; and a similar overall structural transition, including the movement of the thumb and/or finger domains, during the synthesis of nucleic acids.

DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, €, η, ζ, λ, σ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used. Still other useful DNA polymerases, including the 3PDX polymerase are disclosed in U.S. Pat. No. 8,703,461, the disclosure of which is incorporated by reference in its entirety.

RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerases.

Reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and telomerase reverse transcriptase that maintains the telomeres of eukaryotic chromosomes.

Optionally, a polymerase is tagged with a chemiluminescent tag, wherein closed-complex formation is monitored as a stable luminescence signal in the presence of the appropriate luminescence triggers. The unstable interaction of the polymerase with the template nucleic acid in the presence of an incorrect nucleotide results in a measurably weaker signal compared to the closed-complex formed in the presence of the next correct nucleotide. Additionally, a wash step prior to triggering luminescence could remove all polymerase molecules not bound in a stable closed-complex.

Optionally, a polymerase is tagged with an optical scattering tag, wherein closed-complex formation is monitored as a stable optical scattering signal. The unstable interaction of the polymerase with the nucleic acid in the presence of an incorrect nucleotide results in a measurably weaker signal compared to the closed-complex formed in the presence of the next correct nucleotide.

Optionally, the polymerase is tagged with a plasmonic nanoparticle tag, wherein the closed-complex formation is monitored as a shift in plasmonic resonance that is different from the plasmonic resonance in the absence of the closed-complex or the presence of a closed-complex including an incorrect nucleotide. The change in plasmon resonance may be due to the change in local dielectric environment in the closed-complex, or it may be due to the synchronous aggregation of the plasmonic nanoparticles on a cluster of clonally amplified nucleic acid molecules or another means that affects the plasmons differently in the closed-complex configuration.

Optionally, the polymerase is tagged with a Raman scattering tag, wherein the closed-complex formation is monitored as a stable Raman scattering signal. The unstable interaction of polymerase with the nucleic acid in the presence of an incorrect nucleotide results in a measurably weaker signal compared to the closed-complex formed in the presence of the next correct nucleotide.

Optionally, a next correct nucleotide is identified by a tag on a polymerase selected or modified to have a high affinity for nucleotides, wherein the polymerase binds to a nucleotide prior to binding to the template nucleic acid. For example, the DNA polymerase X from the African Swine Fever virus has an altered order of substrate binding, where the polymerase first binds to a nucleotide, then binds to the template nucleic acid. Optionally, a polymerase is incubated with each type of nucleotide in separate compartments, where each compartment contains a different type of nucleotide and where the polymerase is labeled differently with a tag depending on the nucleotide with which it is incubated. In these conditions, unlabeled nucleotides are bound to differently labeled polymerases. The polymerases may be the same kind of polymerase bound to each nucleotide type or different polymerases bound to each nucleotide type. The differentially tagged polymerase-nucleotide complexes may be added simultaneously to any step of the sequencing reaction. Each polymerase-nucleotide complex binds to a template nucleic acid whose next base is complementary to the nucleotide in the polymerase-nucleotide complex. The next correct nucleotide is identified by the tag on the polymerase carrying the nucleotide. The interrogation of the next template base by the labeled polymerase-nucleotide complex may be performed under non-incorporating and/or examination conditions, where once the identity of the next template base is determined, the complex is destabilized and removed, sequestered, and/or diluted and a separate incorporation step is performed in a manner ensuring that only one nucleotide is incorporated.

A common method of introducing a detectable tag on a polymerase optionally involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-hydroxysuccinimide (NHS) chemistry is employed at pH ranges where only the N-terminal amines are reactive (for instance, pH 7), such that only a single tag is added per polymerase.

Optionally, the tag attached to the polymerase is a charge tag, such that the formation of stable closed-complex can be detected by electrical means by measuring changes in local charge density around the template nucleic acids. Methods for detecting electrical charges are well known in the art, including methods such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

Optionally, a charge tag is a peptide tag having an isoelectric point below about 4 or above about 10. Optionally, a polymerase including a peptide tag has a total isoelectric point below about 5 or above about 9. A charge tag may be any moiety which is positively or negatively charged. The charge tag may include additional moieties including mass and/or labels such as dyes. Optionally, the charge tag possesses a positive or negative charge only under certain reaction conditions such as changes in pH.

A polymerase may be labeled with a fluorophore and/or quencher. Optionally, a nucleic acid is labeled with a fluorophore and/or quencher. Optionally, one or more nucleotides are labeled with a fluorophore and/or quencher. Exemplary fluorophores include, but are not limited to, fluorescent nanocrystals; quantum dots; d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl]coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies; Carlsbad Calif.) and Fluorophores Guide (Promega; Madison, Wis.), which are incorporated herein by reference in their entireties. Exemplary quenchers include, but are not limited to, ZEN, IBFQ, BHQ-1, BHQ-2, DDQ-I, DDQ-11, Dabcyl, Qxl quencher, Iowa Black RQ, and IRDye QC-1.

Optionally, a conformationally sensitive dye may be attached close to the active site of the polymerase without affecting the polymerization ability or fidelity of the polymerase; wherein a change in conformation, or a change in polar environment due to the formation of a closed-complex is reflected as a change in fluorescence or absorbance properties of the dye. Common fluorophores such as Cy3 and fluorescein are known to have strong solvatochromatic response to polymerase binding and closed-complex formation, to the extent that the formation of closed-complex can be distinguished clearly from the binary polymerase-nucleic acid complex. Optionally, the closed-complex can be distinguished from binary complexes based on differences in fluorescence or absorbance signals from a conformationally sensitive dye. Optionally, a solvatochromatic dye may be employed to monitor conformational transitions; wherein the change in local polar environment induced by the conformational change can be used as the reporter signal. Solvatochromatic dyes include, but are not limited to, Reichart's dye, IR44, merocyanine dyes (e.g., merocyanine 540), 4-[2-N-substituted-1,4-hydropyridin-4-ylidine)ethylidene] cyclohexa-2,5-dien-1-one, red pyrazolone dyes, azomethine dyes, indoaniline dyes, diazamerocyanine dyes, indigoid dyes, as exemplified by indigo, and others as well as mixtures thereof. Methods to introduce dyes or fluorophores to specific sites of a polymerase are well known in the art. As a non-limiting example, a procedure for site specific labeling of a T7 DNA polymerase with a dye is provided by Tsai et al., in "Site-Specific Labeling of T7 DNA Polymerase with a Conformationally Sensitive Fluorophore and Its Use in Detecting Single-Nucleotide Polymorphisms," *Analytical Biochemistry* 384: 136-144 (2009), which is incorporated by reference herein in its entirety.

Optionally, a polymerase is tagged with a fluorophore at a position that could sense closed-complex formation without interfering with the reaction. The polymerase may be a native or modified polymerase. Modified polymerases include those with one or more amino acid mutations, additions, and/or deletions. Optionally, one or more, but not all, cysteine amino acids are mutated to another amino acid, such as alanine. In this case, the remaining one or more cysteines are used for site-specific conjugation to a fluorophore. Alternatively, one or more amino acids are mutated to a reactive amino acid suitable for fluorophore conjugation, such as cysteines or amino acids including primary amines.

Optionally, binding between a polymerase and a template nucleic acid in the presence of a correct nucleotide may induce a decrease in fluorescence, whereas binding with an incorrect nucleotide causes an increase in fluorescence. Binding between a polymerase and a template nucleic acid in the presence of a correct nucleotide may induce an increase in fluorescence, whereas binding with an incorrect nucleotide causes a decrease in fluorescence. The fluorescent signals may be used to monitor the kinetics of a nucleotide-induced conformational change and identify the next base in the template nucleic acid sequence.

Optionally, the polymerase/nucleic-acid interaction may be monitored by scattering signal originating from the polymerase or tags attached to the polymerase, for instance, nanoparticle tags.

Conditions for Forming and Manipulating Closed-Complexes

As used herein, a closed-complex can be a ternary complex that includes a polymerase, primed template nucleic acid, and nucleotide. The closed-complex may be in a pre-chemistry conformation, wherein a nucleotide is sequestered but not incorporated. The closed-complex may alternatively be in a pre-translocation conformation, wherein a nucleotide is incorporated by formation of a phosphodiester bond with the 3'-end of the primer in the primed template nucleic acid. The closed-complex may be formed in the absence of catalytic metal ions or deficient levels of catalytic metal ions, thereby physically sequestering the next correct nucleotide within the polymerase active site without chemical incorporation. Optionally, the sequestered nucleotide may be a non-incorporable nucleotide. The closed-complex may be formed in the presence of catalytic metal ions, where the closed-complex includes a nucleotide analog which is incorporated, but a PPi is not capable of release. In this instance, the closed-complex is stabilized in a pre-translocation conformation. Optionally, a pre-translocation conformation is stabilized by chemically cross-linking the polymerase. Optionally, the closed-complex may be stabilized by external means. In some instances, the closed-complex may be stabilized by allosteric binding of small molecules, or macromolecules such as antibodies or aptamers. Optionally, closed-complex may be stabilized by pyrophosphate analogs that bind close to the active site with high affinity, preventing translocation of the polymerase.

As used herein, a stabilized closed-complex or stabilized ternary complex refers to a polymerase trapped at the polymerization initiation site (3'-end of the primer) of the primed template nucleic acid by one or a combinations of means, including but not limited to, crosslinking the thumb and finger domains in the closed conformation, binding of an allosteric inhibitor that prevents return of the polymerase to an open conformation, binding of pyrophosphate analogs that trap polymerase in the pre-translocation step, absence of catalytic metal ions in the active site of the polymerase, and addition of a metal ions such as nickel, tin and $Sr^{2+}$ as substitutes for a catalytic metal ion. As such, the polymerase may be trapped at the polymerization initiation site even after the incorporation of a nucleotide. Therefore, the polymerase may be trapped in the pre-chemistry conformation, pre-translocation step, post-translocation step or any intermediate step thereof. Thus, allowing for sufficient examination and identification of the next correct nucleotide or base.

As described herein, a polymerase-based, sequencing-by-binding reaction generally involves providing a primed template nucleic acid with a polymerase and one or more types of nucleotides, wherein the nucleotides may or may not be complementary to the next base of the primed template nucleic acid, and examining the interaction of the polymerase with the primed template nucleic acid under conditions wherein either chemical incorporation of a nucleotide into the primed template nucleic acid is disabled or severely inhibited in the pre-chemistry conformation or one or more complementary nucleotide incorporation occurs at the 3'-end of the primer. Optionally, wherein the pre-chemistry conformation is stabilized prior to nucleotide incorporation, preferably using stabilizers, a separate incorporation step may follow the examination step to incorporate a single nucleotide to the 3'-end of the primer. Optionally, where a single nucleotide incorporation occurs, the pre-translocation conformation may be stabilized to facilitate examination and/or prevent subsequent nucleotide incorporation.

As indicated above, the presently described methods for sequencing a nucleic acid include an examination step. The examination step involves binding a polymerase to the polymerization initiation site of a primed template nucleic acid in a reaction mixture including one or more nucleotides, and monitoring the interaction. Optionally, a nucleotide is sequestered within the polymerase-primed template nucleic acid complex to form a closed-complex, under conditions in which incorporation of the enclosed nucleotide by the polymerase is attenuated or inhibited. Optionally a stabilizer is added to stabilize the ternary complex in the presence of the next correct nucleotide. This closed-complex is in a stabilized or polymerase-trapped pre-chemistry conformation. A closed-complex allows for the incorporation of the enclosed nucleotide but does not allow for the incorporation of a subsequent nucleotide. This closed-complex is in a stabilized or trapped pre-translocation conformation. Optionally, the polymerase is trapped at the polymerization site in its closed-complex by one or a combination of means including, but not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped closed-complex provides information about the identity of the next base on the nucleic acid template.

Optionally, a closed-complex is released from its trapped or stabilized conformation, which may allow for nucleotide incorporation to the 3'-end of the template nucleic acid primer. The closed-complex can be destabilized and/or released by modulating the composition of the reaction conditions. In addition, the closed-complex can be destabilized by electrical, magnetic, and/or mechanical means. Mechanical means include mechanical agitation, for example, by using ultrasound agitation. Mechanical vibration destabilizes the closed-complex and suppresses binding of the polymerase to the DNA. Thus, rather than a wash step where the examination reaction mixture is replaced with an incorporation mixture, mechanical agitation may be used to remove the polymerase from the template nucleic acid, enabling cycling through successive incorporation steps with a single nucleotide addition per step.

Any combination of closed-complex stabilization or closed-complex release reaction conditions and/or methods may be combined. For example, a polymerase inhibitor that stabilizes a closed-complex may be present in the examination reaction with a catalytic ion, which functions to release the closed-complex. In the aforementioned example, the closed-complex may be stabilized or released, depending on the polymerase inhibitor properties and concentration, the concentration of the catalytic metal ion, other reagents and/or conditions of the reaction mixture, and any combination thereof.

The closed-complex can be stabilized under reaction conditions where covalent attachment of a nucleotide to the 3'-end of the primer in the primed template nucleic acid is attenuated. Optionally, the closed-complex is in a pre-chemistry conformation or ternary complex. Optionally, the closed-complex is in a pre-translocation conformation. The formation of this closed-complex can be initiated and/or stabilized by modulating the availability of a catalytic metal ion that permits closed-complex release and/or chemical incorporation of a nucleotide to the primer in the reaction mixture. Exemplary metal ions include, but are not limited to, magnesium, manganese, cobalt, and barium. Catalytic ions may be any formulation, for example, being provided by salts such as $MgCl_2$, $Mg(CH_3CO_2)_2$, and $MnCl_2$.

The selection and/or concentration of the catalytic metal ion may be based on the polymerase and/or nucleotides in the sequencing reaction. For example, the HIV reverse transcriptase utilizes magnesium for nucleotide incorporation (N Kaushik, *Biochemistry* 35:11536-11546 (1996), and H P Patel, *Biochemistry* 34:5351-5363 (1995), which are incorporated by reference herein in their entireties). The rate of closed-complex formation using magnesium versus manganese can be different depending on the polymerase and the identity of the nucleotide. Thus, the stability of the closed-complex may differ depending on catalytic metal ion, polymerase, and/or nucleotide identity. Further, the concentration of catalytic ion necessary for closed-complex stabilization may vary depending on the catalytic metal ion, polymerase, and/or nucleotide identity and can be readily determined using the guidance provided herein. For example, nucleotide incorporation may occur at high catalytic ion concentrations of one metal ion but does not occur at low concentrations of the same metal ion, or vice versa. Therefore, modifying metal ion identity, metal ion concentration, polymerase identity, and/or nucleotide identity allows for controlled examination reaction conditions.

The closed-complex may be formed and/or stabilized by sequestering, removing, reducing, omitting, and/or chelating a catalytic metal ion during the examination step of the sequencing reaction so that closed-complex release and/or chemical incorporation does not occur. Chelation includes any procedure that renders the catalytic metal ion unavailable for nucleotide incorporation, including using EDTA and/or EGTA. A reduction includes diluting the concentration of a catalytic metal ion in the reaction mixture. The reaction mixture can be diluted or replaced with a solution including a non-catalytic ion, which permits closed-complex formation, but inhibits nucleotide incorporation. Non-catalytic ions include, but are not limited to, calcium, strontium, scandium, titanium, vanadium, chromium, iron, cobalt, nickel, copper, zinc, gallium, germanium, arsenic, selenium, rhodium, and strontium. Optionally, $Ni^{2+}$ is provided in an examination reaction to facilitate closed-complex formation. Optionally, $Sr^{2+}$ is provided in an examination reaction to facilitate closed-complex formation. Optionally, a non-catalytic metal ion and a catalytic metal ion are both present in the reaction mixture, wherein one ion is present in a higher effective concentration than the other. In the provided methods, a non-catalytic ion such as cobalt can become catalytic (i.e., facilitate nucleotide incorporation) at high concentrations. Thus, optionally, a low concentration of a non-catalytic metal ion is used to facilitate ternary complex formation and a higher concentration of the non-catalytic metal ion is used to facilitate incorporation.

Non-catalytic ions may be added to a reaction mixture under examination conditions. The reaction may already include nucleotides. Optionally, non-catalytic ions are complexed to one or more nucleotides and complexed nucleotides are added to the reaction mixture. Non-catalytic ions can complex to nucleotides by mixing nucleotides with non-catalytic ions at elevated temperatures (about 80° C.). For example, a chromium nucleotide complex may be added to a mixture to facilitate closed-complex formation and stabilization. Optionally, a chromium nucleotide complex is a chromium monodentate, bidentate, or tridentate complex. Optionally, a chromium nucleotide complex is an α-monodentate, or β-γ-bidentate nucleotide.

Optionally, a closed-complex is formed between a polymerase, primed template nucleic acid, and nucleotide in reaction conditions including $Sr^{2+}$, wherein $Sr^{2+}$ promotes the formation of the closed-complex. The presence of $Sr^{2+}$ can allow for the favorable formation of a closed-complex including a next correct nucleotide over the formation a complex including an incorrect nucleotide. The $Sr^{2+}$ ion may be present at concentrations from about 0.01 mM to about 30 mM. Optionally, $Sr^{2+}$ is present as 10 mM $SrCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each of the dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash step removes unbound nucleotides, and $Mg^{2+}$ is added to the reaction to induce pyrophosphate (PPi) cleavage and nucleotide incorporation. Optionally, the wash step includes $Sr^{2+}$ to maintain the stability of the ternary complex, preventing the dissociation of the ternary complex. The reaction may be repeated until a desired sequence read-length is obtained.

Optionally, a closed-complex is formed between a polymerase, primed template nucleic acid, and nucleotide in reaction conditions including $Ni^{2+}$, wherein $Ni^{2+}$ promotes the formation of the closed-complex. The presence of $Ni^{2+}$ can allow for the favorable formation of a closed-complex including a next correct nucleotide over the formation a complex including an incorrect nucleotide. The $Ni^{2+}$ ion may be present at concentrations from about 0.01 mM to about 30 mM. Optionally, $Ni^{2+}$ is present as 10 mM $NiCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each of the dNTPs (e.g., dATP, dTTP, dCTP, dGTP) in the presence of $Sr^{2+}$ can be different. Therefore, examination can involve measuring the binding affinities of polymerase-template nucleic acids to dNTPs;

wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash removes unbound nucleotides and polymerase, and $Mg^{2+}$ is added to the reaction to induce pyrophosphate (PPi) cleavage and nucleotide incorporation. Optionally, the wash buffer includes $Ni^{2+}$ to maintain the stability of the ternary complex, preventing the dissociation of the ternary complex. The reaction may be repeated until a desired sequence read length is obtained.

Optionally, a closed-complex is formed between a polymerase, primed template nucleic acid, and nucleotide in reaction conditions including non-catalytic concentrations of $Co^{2+}$, wherein $Co^{2+}$ promotes the formation of the closed-complex. The presence of non-catalytic concentrations of $Co^{2+}$ can allow for the favorable formation of a closed-complex including a next correct nucleotide over the formation a complex including an incorrect nucleotide. The $Co^{2+}$ ion may be present at concentrations from about 0.01 mM to about 0.5 mM. Optionally, $Co^{2+}$ is present as 0.5 mM $CoCl_2$. The formation of the closed-complex is monitored under examination conditions to identify the next base in the template nucleic acid of the closed-complex. The affinity of the polymerase (e.g., Klenow fragment of E. coli DNA polymerase I, Bst) for each of the dNTPs (e.g., dATP, dTTP, dCTP, dGTP) in the presence of $Co^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilize the ternary interactions between the polymerase, the primed template nucleic acid, and the next correct nucleotide. After examination, a wash removes unbound nucleotides and polymerase, and $Co^{2+}$ at a catalytic concentration is added to the reaction to induce pyrophosphate (PPi) cleavage and nucleotide incorporation. Optionally, the wash buffer includes non-catalytic amounts of $Co^{2+}$ to maintain the stability of the ternary complex, preventing the dissociation of the ternary complex. The reaction may be repeated until a desired sequence read length is obtained.

Optionally, a catalytic metal ion may facilitate the formation of a closed-complex without subsequent nucleotide incorporation and closed-complex release. Optionally, a concentration of 0.5, 1, 2, 3, 4, 5, 6, 7, 8, 9, or 10 µM $Mg^{2+}$ in a reaction mixture can induce conformational change of a polymerase to form a closed-complex without subsequent nucleotide incorporation, PPi and closed-complex release. Optionally, the concentration of $Mg^{2+}$ is from about 0.5 µM to about 10 µM, from about 0.5 µM to about 5 µM, from about 0.5 µM to about 4 µM, from about 0.5 µM to about 3 µM, from about µM to about 5 µM, from about 1 µM to about 4 µM, and from about 1 µM to about 3 µM.

Optionally, the concentration of available catalytic metal ion in the sequencing reaction which is necessary to allow nucleotide incorporation is from about 0.001 mM to about 10 mM, from about 0.01 mM to about 5 mM, from about 0.01 mM to about 3 mM, from about 0.01 mM to about 2 mM, from about 0.01 mM to about 1 mM, from about 0.05 mM to about 10 mM, from about 0.05 mM to about 5 mM, from about 0.05 mM to about 3 mM, from about 0.05 to about 2 mM, or from about 0.05 mM to about 1 mM. Optionally, the concentration of catalytic metal ion is from 5 mM to 50 mM. Optionally, the concentration of catalytic metal ion is from 5 mM to 15 mM, or about 10 mM.

A non-catalytic ion may be added to the reaction mixture at any stage including before, during, or after any of the following reaction steps: providing a primed template nucleic acid, providing a polymerase, formation of a binary complex, providing a nucleotide, formation of a pre-chemistry closed-complex, nucleotide incorporation, formation of a pre-translocation closed-complex, and formation of a post-translocation conformation. The non-catalytic ion may be added to the reaction mixture during wash steps. The non-catalytic ion may be present through the reaction in the reaction mixture. For example, a catalytic ion is added to the reaction mixture at concentrations which dilute the non-catalytic metal ion, allowing for nucleotide incorporation.

The ability of catalytic and non-catalytic ions to modulate nucleotide incorporation may depend on conditions in the reaction mixture including, but not limited to, pH, ionic strength, chelating agents, chemical cross-linking, modified polymerases, non-incorporable nucleotides, mechanical or vibration energy, and electric fields.

Optionally, the concentration of non-catalytic metal ion in the sequencing reaction necessary to allow for closed-complex formation without nucleotide incorporation is from about 0.1 mM to about 50 mM, from about 0.1 mM to about 40 mM, from about 0.1 mM to about 30 mM, from about 0.1 mM to about 20 mM, from about 0.1 mM to about 10 mM, from about 0.1 mM to about 5 mM, from about 0.1 to about 1 mM, from about 1 mM to about 50 mM, from about 1 to about 40 mM, from about 1 mM to about 30 mM, from about 1 mM to about 20 mM, from about 1 mM to about 10 mM, from about 1 mM to about 5 mM, from about 2 mM to about 30 mM, from about 2 mM to about 20 mM, from about 2 mM to about 10 mM, or any concentration within these ranges.

A closed-complex may be formed and/or stabilized by the addition of a polymerase inhibitor to the examination reaction mixture. Inhibitor molecules phosphonoacetate (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule, near the active site of the enzyme, traps the polymerase in either a pre-translocation or post-translocation step of the nucleotide incorporation cycle, stabilizing the polymerase in its closed-complex conformation before or after the incorporation of a nucleotide, and forcing the polymerase to be bound to the template nucleic acid until the inhibitor molecules are not available in the reaction mixture by removal, dilution or chelation.

Thus, provided is a method for sequencing a template nucleic acid molecule including an examination step including providing a template nucleic acid molecule primed with a primer; contacting the primed template nucleic acid molecule with a first reaction mixture including a polymerase, a polymerase inhibitor and at least one unlabeled nucleotide molecule; monitoring the interaction of the polymerase with the primed template nucleic acid molecule in the presence of the unlabeled nucleotide molecule without incorporation of the nucleotide into the primer of the primed template nucleic acid molecule; and identifying the nucleotide that is complementary to the next base of the primed template nucleic acid molecule by the monitored interaction. The polymerase inhibitor prevents the incorporation of the unlabeled nucleotide molecule into the primer of the primer template nucleic acid.

Optionally, the inhibitor is a non-competitive inhibitor, an allosteric inhibitor, or an uncompetitive allosteric inhibitor. Optionally, the polymerase inhibitor competes with a catalytic ion binding site in the polymerase.

Detection Platforms: Instrumentation for Detecting the Closed-Complex

The interaction between the polymerase and the template nucleic acid in the presence of nucleotides can be monitored with or without the use of an exogenous label. For example, the sequencing reaction may be monitored by detecting the change in refractive index, fluorescence emission, charge detection, Raman scattering detection, ellipsometry detection, pH detection, size detection, mass detection, surface plasmon resonance, guided mode resonance, nanopore optical interferometry, whispering gallery mode resonance, nanoparticle scattering, photonic crystal, quartz crystal microbalance, bio-layer interferometry, vibrational detection, pressure detection and other label-free detection schemes that detect the added mass or refractive index due to polymerase binding in a closed-complex with a template nucleic acid.

Optionally, detecting a change in refractive index is accomplished by one or a combination of means, including, but not limited to, surface plasmon resonance sensing, localized plasmon resonance sensing, plasmon-photon coupling sensing, transmission sensing through sub-wavelength nanoholes (enhanced optical transmission), photonic crystal sensing, interferometry sensing, refraction sensing, guided mode resonance sensing, ring resonator sensing, or ellipsometry sensing. Optionally, nucleic acid molecules may be localized to a surface, wherein the interaction of polymerase with nucleic acids in the presence of various nucleotides may be measured as a change in the local refractive index.

Optionally, the template nucleic acid is tethered to or localized appropriately on or near a surface, such that the interaction of polymerase and template nucleic acid in the presence of nucleotides changes the light transmitted across or reflected from the surface. The surface may contain nanostructures. Optionally, the surface is capable of sustaining plasmons or plasmon resonance. Optionally, the surface is a photonic substrate, not limited to a resonant cavity, resonant ring or photonic crystal slab. Optionally, the surface is a guided mode resonance sensor. Optionally, the nucleic acid is tethered to, or localized appropriately on or near a nanohole array, a nanoparticle or a microparticle, such that the interaction of polymerase and template nucleic acid in the presence of nucleotides changes the absorbance, scattering, reflection or resonance of the light interacting with the microparticle or nanoparticle.

Optionally, a nanohole array on a gold surface is used as a refractive index sensor. The template nucleic acid may be attached to a metal surface by standard thiol chemistry, incorporating the thiol group on one of the primers used in a PCR reaction to amplify the DNA. When the dimensions of the nanohole array are appropriately tuned to the incident light, binding of the polymerase to the template nucleic acid in the presence of nucleotides can be monitored as a change in light transmitted across the nanoholes. For both the labeled and label-free schemes, simple and straightforward measurement of equilibrium signal intensity may reveal the formation of a stable closed-complex.

Optionally, nucleic acid molecules are localized to a surface capable of sustaining surface plasmons, wherein the change in refractive index caused by the polymerase interaction with localized nucleic acids may be monitored through the change in the properties of the surface plasmons, wherein further, said properties of surface plasmons may include surface plasmon resonance. Surface plasmons, localized surface plasmons (LSP), or surface plasmon polaritons (SPP), arise from the coupling of electromagnetic waves to plasma oscillations of surface charges. LSPs are confined to nanoparticle surfaces, while SPPs and are confined to high electron density surfaces, at the interface between high electron mobility surfaces and dielectric media. Surface plasmons may propagate along the direction of the interface, whereas they penetrate into the dielectric medium only in an evanescent fashion. Surface plasmon resonance conditions are established when the frequency of incident electromagnetic radiation matches the natural frequency of oscillation of the surface electrons. Changes in dielectric properties at the interface, for instance due to binding or molecular crowding, affects the oscillation of surface electrons, thereby altering the surface plasmon resonance wavelength. Surfaces capable of surface plasmon resonance include, in a non-limiting manner, nanoparticles, clusters and aggregates of nanoparticles, continuous planar surfaces, nanostructured surfaces, and microstructured surfaces. Materials such as gold, silver, aluminum, high conductivity metal oxides (e.g., indium tin oxide, zinc oxide, tungsten oxide) are capable of supporting surface plasmon resonance at their surfaces.

Optionally, a single nucleic acid molecule, or multiple clonal copies of a nucleic acid, are attached to a nanoparticle, such that binding of polymerase to the nucleic acid causes a shift in the localized surface plasmon resonance (LSPR). Light incident on the nanoparticles induces the conduction electrons in them to oscillate collectively with a resonant frequency that depends on the nanoparticles' size, shape and composition. Nanoparticles of interest may assume different shapes, including spherical nanoparticles, nanorods, nanopyramids, nanodiamonds, and nanodiscs. As a result of these LSPR modes, the nanoparticles absorb and scatter light so intensely that single nanoparticles are easily observed by eye using dark-field (optical scattering) microscopy. For example, a single 80-nm silver nanosphere scatters 445-nm blue light with a scattering cross-section of $3\times10^{-2}$ $m^2$, a million-fold greater than the fluorescence cross-section of a fluorescein molecule, and a thousand fold greater than the cross-section of a similarly sized nanosphere filled with fluorescein to the self-quenching limit. Optionally, the nanoparticles are plasmon-resonant particles configured as ultra-bright, nanosized optical scatters with a scattering peak anywhere in the visible spectrum. Plasmon-resonant particles are advantageous as they do not bleach. Optionally, plasmon-resonant particles are prepared, coated with template nucleic acids, and provided in a reaction mixture including a polymerase and one or more nucleotides, wherein a polymerase-template nucleic acid-particle interaction is detected. One or more of the aforementioned steps may be based on or derived from one or more methods disclosed by Schultz et al., in *PNAS* 97:996-1001 (2000), which is incorporated by reference herein in its entirety.

The very large extinction coefficients at resonant wavelength enables noble-metal nanoparticles to serve as extremely intense labels for near-surface interactions. Optionally, polymerase interaction with nanoparticle-localized DNA results in a shift in the resonant wavelength. The change in resonant wavelength due to binding or binding interactions can be measured in one of many ways. Optionally, the illumination is scanned through a range of wavelengths to identify the wavelength at which maximum scattering is observed at an imaging device. Optionally, broadband illumination is utilized in conjunction with a dispersive element near the imaging device, such that the resonant peak is identified spectroscopically. Optionally, the nanoparticle system may be illuminated at its resonant wavelength, or near its resonant wavelength, and any binding interactions may be observed as a drop in intensity of light scattered as the new resonant wavelength shifts away from the illumination wavelength. Depending on the positioning of the illuminating wavelength, interactions may even appear as an increase in nanoparticle scattering as the resonance peak shifts towards the illumination wavelength. Optionally, DNA-attached-nanoparticles may be localized to a surface, or, alternatively, the DNA-attached-nanoparticles may be suspended in solution. A comprehensive review of biosensing using nanoparticles is described by Anker et al., in *Nature Materials* 7: 442-453 (2008), which is incorporated in its entirety herein by reference.

Optionally, nano-features capable of LSPR are lithographically patterned on a planar substrate. The two-dimensional patterning of nano-features has advantages in multiplexing and high-throughput analysis of a large number of different nucleic acid molecules. Optionally, gold nanoposts are substrates for surface plasmon resonance imaging detection of polymerase-template nucleic acid interactions, wherein the nucleic acids are attached to the nanoposts. Nanostructure size and period can influence surface plasmon resonance signal enhancement, optionally, providing a 2, 3, 4, 5, 6, 7, 8-fold or higher signal amplification when compared to control films.

Optionally, surface plasmon resonance may be sustained in planar surfaces. A number of commercial instruments based on the Kretschmann configuration (e.g., Biacore, Uppsala, Sweden) and surface plasmon resonance imaging (e.g., GWC Technologies; Madison, Wis.; or Horiba; Kyoto, Japan) are available and have well established protocols for attaching DNA to their surfaces, as single spots and in multiplexed array patterns. In the Kretschmann configuration, a metal film, typically gold, is evaporated onto the side of a prism and incident radiation is launched at an angle to excite the surface plasmons. An evanescent wave penetrates through the metal film exciting plasmons on the other side, where it may be used to monitor near-surface and surface interactions near the gold film. At the resonant angle, the light reflected from the prism-gold interface is severely attenuated. Assuming fixed wavelength illumination, binding interactions may be examined by monitoring both the intensity of the reflected light at a fixed angle close to the resonant angle, as well as by monitoring the changes in angle of incidence required to establish surface plasmon resonance conditions (minimum reflectivity). When a 2D imaging device such as a CCD or CMOS camera is utilized to monitor the reflected light, the entire illumination area may be imaged with high resolution. This method is called surface plasmon resonance imaging (SPRi). It allows high throughput analysis of independent regions on the surface simultaneously. Broadband illumination may also be used, in a fixed angle configuration, wherein the wavelength that is coupled to the surface plasmon resonance is identified spectroscopically by looking for dips in the reflected spectrum. Surface interactions are monitored through shifts in the resonant wavelength.

Surface plasmon resonance is a well-established method for monitoring protein-nucleic acid interactions, and there exist many standard protocols both for nucleic acid attachment as well as for analyzing the data. Illustrative references from the literature include Cho et al., "Binding Kinetics of DNA-Protein Interaction Using Surface Plasmon Resonance," *Protocol Exchange*, May 22, 2013; and Brockman et al., "A Multistep Chemical Modification Procedure To Create DNA Arrays on Gold Surfaces for the Study of Protein-DNA Interactions with Surface Plasmon Resonance Imaging," *Journal of the American Chemical Society* 121: 8044-51 (1999), both of which are incorporated by reference herein in their entireties.

Polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, extraordinary optical transmission (EOT) through a nanoholes array may be used to monitor nucleic-acid/polymerase interactions. Light transmitted across sub-wavelength nanoholes in plasmonic metal films is higher than expected from classical electromagnetic theory. This enhanced optical transmission may be explained by considering plasmonic resonant coupling to the incident radiation, whereby at resonant wavelength, a larger than anticipated fraction of light is transmitted across the metallic nanoholes. The enhanced optical transmission is dependent on the dimensions and pitch of the nanoholes, properties of the metal, as well as the dielectric properties of the medium on either side of the metal film bearing the nanoholes. In the context of a biosensor, the transmissivity of the metallic nanohole array depends on the refractive index of the medium contacting the metal film, whereby, for instance, the interaction of polymerase with nucleic acid attached to the metal surface may be monitored as a change in intensity of light transmitted across the nanoholes array. Instrumentation and alignment requirements when using the EOT/plasmonic nanohole array approach of surface plasmon resonance may be employed using very compact optics and imaging elements. Low power LED illumination and a CMOS or CCD camera may suffice to implement robust EOT plasmonic sensors. An exemplary nanohole array-based surface plasmon resonance sensing device is described by Escobedo et al., in "Integrated Nanohole Array Surface Plasmon Resonance Sensing Device Using a Dual-Wavelength Source," *Journal of Micromechanics and Microengineering* 21: 115001 (2011), which is herein incorporated by reference in its entirety.

The plasmonic nanohole array may be patterned on an optically opaque layer of gold (greater than 50 nm thickness) deposited on a glass surface. Optionally, the plasmonic nanohole array may be patterned on an optically thick film of aluminum or silver deposited on glass. Optionally, the nanohole array is patterned on an optically thick metal layer deposited on low refractive index plastic. Patterning plasmonic nanohole arrays on low refractive index plastics enhances the sensitivity of the device to refractive index changes by better matching the refractive indices on the two sides of the metal layer. Optionally, refractive index sensitivity of the nanohole array is increased by increasing the distance between holes. Optionally, nanohole arrays are fabricated by replication, for example, by embossing, casting, imprint-lithography, or template-stripping. Optionally, nanohole arrays are fabricated by self-assembly using colloids. Optionally, nanohole arrays are fabricated by projection direct patterning, such as laser interference lithography.

A nano-bucket configuration may be preferable to a nanohole configuration. In the nanohole configuration, the bottom of the nano-feature is glass or plastic or other appropriate dielectric, whereas in the nano-bucket configuration, the bottom of the nano-feature includes a plasmonic metal. The nano-bucket array advantageously is relatively simple to fabricate while maintaining the transmission sensitivity to local refractive index.

Optionally, the nanohole array plasmonic sensing is combined with lens-free holographic imaging for large area imaging in an inexpensive manner. Optionally, a plasmonic biosensing platform includes a plasmonic chip with nanohole arrays, a light-emitting diode source configured to illuminate the chip, and a CMOS imager chip to record diffraction patterns of the nanoholes, which is modulated by molecular binding events on the surface. The binding events may be the formation of a closed-complex between a polymerase and a template nucleic acid in the presence of a nucleotide.

The methods to functionalize surfaces (for nucleic acid attachment) for surface plasmon resonance sensing may be directly applied to EOT nanohole arrays as both sensing schemes employ similar metal surfaces to which nucleic acids need to be attached.

Optionally, the refractive index changes associated with polymerase/nucleic acid interaction may be monitored on nanostructured surfaces that do not support plasmons. Optionally, guided mode resonance may be used to monitor the polymerase/nucleic-acid interaction. Guided-mode resonance or waveguide-mode resonance is a phenomenon wherein the guided modes of an optical waveguide can be excited and simultaneously extracted by the introduction of a phase-matching element, such as a diffraction grating or prism. Such guided modes are also called "leaky modes," as they do not remain guided and have been observed in one and two-dimensional photonic crystal slabs. Guided mode resonance may be considered a coupling of a diffracted mode to a waveguide mode of two optical structured placed adjacent or on top of each other. For instance, for a diffraction grating placed on top of an optical waveguide, one of the diffracted modes may couple exactly into the guided mode of the optical waveguide, resulting in propagation of that mode along the waveguide. For off-resonance conditions, no light is coupled into the waveguide, so the structure may appear completely transparent (if dielectric waveguides are used). At resonance, the resonant wavelength is strongly coupled into the waveguide and may be couple out of the structure depending on downstream elements from the grating-waveguide interface. In cases where the grating coupler is extended over the entire surface of the waveguide, the light cannot be guided, as any light coupled in is coupled out at the next grating element. Therefore, in a grating waveguide structure, resonance is observed as a strong reflection peak, whereas the structure is transparent to off-resonance conditions. The resonance conditions are dependent on angle, grating properties, polarization and wavelength of incident light. For cases where the guided mode propagation is not present, for instance due to a grating couple to the entire surface of the waveguide, the resonant mode may also be called leaky-mode resonance, in light of the strong optical confinement and evanescent propagation of radiation in a transverse direction from the waveguide layer. Change in dielectric properties near the grating, for instance due to binding of biomolecules affects the coupling into the waveguide, thereby altering the resonant conditions. Optionally, where nucleic acid molecules are attached to the surface of grating waveguide structures, the polymerase/nucleic-acid interaction may be monitored as a change in wavelength of the leaky mode resonance.

A diffraction element may be used directly on a transparent substrate without an explicit need for a waveguide element. The change in resonance conditions due to interactions near the grating nanostructure may be monitored as resonant wavelength shifts in the reflected or transmitted radiation.

Reflected light from a nucleic acid attached guided mode resonant sensor may be used to monitor the polymerase/nucleic-acid interaction. A broadband illumination source may be employed for illumination, and a spectroscopic examination of reflected light could reveal changes in local refractive index due to polymerase binding.

Optionally, a broadband illumination may be used and the transmitted light may be examined to identify resonant shifts due to polymerase interaction. A linearly polarized narrow band illumination may be used, and the transmitted light may be filtered through a cross-polarizer; wherein the transmitted light is completely attenuated due to the crossed polarizers excepting for the leaky mode response whose polarization is modified. This implementation converts refractive index monitoring to a simple transmission assay that may be monitored on inexpensive imaging systems. Published material describe the assembly of the optical components. See, Nazirizadeh et al., "Low-Cost Label-Free Biosensors Using Photonic Crystals Embedded between Crossed Polarizers," *Optics Express* 18: 19120-19128 (2010), which is incorporated herein by reference in its entirety.

In addition to nanostructured surfaces, plain, unstructured surfaces may also be used advantageously for monitoring refractive index modulations. Optionally, interferometry may be employed to monitor the interaction of polymerase with nucleic acid bound to an un-structured, optically transparent substrate. Nucleic acid molecules may be attached to the top surface of a glass slide by any means known in the art, and the system illuminated from the bottom surface of the glass slide. There are two reflection surfaces in this configuration, one reflection from the bottom surface of the glass slide, and the other from the top surface which has nucleic acid molecules attached to it. The two reflected waves may interfere with each other causing constructive or destructive interference based on the path length differences, with the wave reflected from the top surface modulated by the changes in dielectric constant due to the bound nucleic acid molecules (and subsequently by the interaction of polymerase with the bound nucleic acid molecules). With the reflection from the bottom surface unchanged, any binding to the nucleic acid molecules may be reflected in the phase difference between the beams reflected from the top and bottom surfaces, which in turn affects the interference pattern that is observed. Optionally, bio-layer interferometry is used to monitor the nucleic acid/polymerase interaction. Bio-layer interferometry may be performed on commercial devices such as those sold by Pall Forte Bio corporation (Menlo Park, Calif.).

Optionally, the reflected light from the top surface is selectively chosen by using focusing optics. The reflected light from the bottom surface is disregarded because it is not in the focal plane. Focusing only on the nucleic-acid-attached top surface, the light collected by the focusing lens includes a planar wave, corresponding to the partially reflected incident radiation, and a scattered wave, corresponding to the radiations scattered in the collection direction by molecules in the focal plane. These two components may be made to interfere if the incident radiation is coherent. This scattering based interferometric detection is extremely sensitive and can be used to detect down to single protein molecules.

Optionally, a field-effect transistor (FET) is configured as a biosensor for the detection of a closed-complex. A gate terminal of the FET is modified by the addition of template nucleic acids. The binding of a polymerase including a charged tag results in changes in electrochemical signals. Binding of a polymerase with a next correct nucleotide to the template nucleic acid provides different signals than polymerase binding to a template nucleic acid in the presence of other incorrect nucleotides, where each incorrect nucleotide may also provide a different signal. Optionally, polymerase interactions with a template nucleic acid are monitored using FET without the use of a an exogenous label on the polymerase, primed template nucleic acid, or nucleotide. Optionally, the pH change that occurs due to release of $H^+$ ions during the incorporation reaction is detected using a FET. Optionally, the polymerase includes a tag that generates continuous $H^+$ ions that is detected by the FET. Optionally, the continuous $H^+$ ion generating tag is an ATP synthase. Optionally, the continuous $H^+$ ion generation tag is palladium, copper or another catalyst. Optionally, the release of a PPi after nucleotide incorporation is detected using FET. For example, one type of nucleotide may be provided to a reaction at a time. Once the next correct nucleotide is added and conditions allow for incorporation, PPi is cleaved, released, and detected using FET, therefore identifying the next correct nucleotide and the next base. Optionally, template nucleic acids are bound to walls of a nanotube. Optionally, a polymerase is bound to a wall of a nanotube. FET is advantageous for use as a sequencing sensor due to its small size and low weight, making it appropriate for use as a portable sequencing monitoring component. Details of FET detection of molecular interactions are described by Kim et al., in "An FET-Type Charge Sensor for Highly Sensitive Detection of DNA Sequence," *Biosensors and Bioelectronics, Microsensors and Microsystems* 20: 69-74 (2004), doi:10.1016/j.bios.2004.01.025; and by Star et al., in "Electronic Detection of Specific Protein Binding Using Nanotube FET Devices," *Nano Letters* 3: 459-63 (2003), doi:10.1021/nl0340172, which are incorporated by reference herein in their entireties.

By way of example, the polymerase includes a fluorescent tag. To monitor polymerase-nucleic acid interaction with high signal-to-noise, evanescent illumination or confocal imaging may be employed. The formation of a closed-complex on localized template nucleic acids may be observed as an increased fluorescence compared to the background, for instance, whereas in some instances it may be also be observed as a decreased fluorescence due to quenching or change in local polar environment. Optionally, a fraction of polymerase molecules may be tagged with a fluorophore while another fraction may be tagged with a quencher in the same reaction mixture; wherein, the formation of closed-complex on a localized, clonal population of nucleic acid is revealed as decrease in fluorescence compared to the background. The clonal population of nucleic acids may be attached to a support surface such as a planar substrate, microparticle, or nanoparticle. Optionally, a polymerase is tagged with a fluorophore, luminophore, chemiluminophore, chromophore, or bioluminophore.

Optionally, a plurality of template nucleic acids is tethered to a surface and one (or more) dNTPs are flowed in sequentially. The spectrum of affinities reveals the identity of the next correct nucleotide and therefore the next base in the template nucleic acid. Optionally, the affinities are measured without needing to remove and replace reaction mixture conditions (i.e., a wash step). Autocorrelation of the measured intensities of the binding interaction, for instance, could readily reveal the dynamics of nucleic acid sequence. Optionally, examination includes monitoring the affinity of the polymerase to the primed template nucleic acid in the presence of nucleotides. Optionally, the polymerase binds transiently with the nucleic acid and the binding kinetics and affinity provides information about the identity of the next base on the template nucleic acid. Optionally, a closed-complex is formed, wherein the reaction conditions involved in the formation of the closed-complex provide information about the next base on the nucleic acid.

Any technique that can measure dynamic interactions between a polymerase and nucleic acid may be used to measure the affinities and enable the sequencing reaction methods disclosed herein.

Systems for Detecting Nucleotide-Specific Ternary Complex Formation

The provided methods can be performed using a platform, where any component of the nucleic acid polymerization reaction is localized to a surface. Optionally, the template nucleic acid is attached to a planar substrate, a nanohole array, a microparticle, or a nanoparticle.

Optionally, all reaction components are freely suspended in the reaction mixture, and not immobilized to a solid support substrate.

Optionally, the template nucleic acid is immobilized to a surface. The surface may be a planar substrate, a hydrogel, a nanohole array, a microparticle, or a nanoparticle. Optionally, the reaction mixtures contain a plurality of clonally amplified template nucleic acid molecules. Optionally, the reaction mixtures contain a plurality of distinguishable template nucleic acids.

Provided herein, inter alia, are systems for performing sequencing reactions involving the examination of the interaction between a polymerase and a primed template nucleic acid in the presence of nucleotides to identify the next base in the template closed-complex by one or a combination of means including, but not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped polymerase complex provides information about the identity of the next base on the nucleic acid template.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanostructure. Optionally, the system includes one or more reagents and instructions necessary to bind template DNA molecules onto a nanostructure. For example, the system provides a nanostructure, such as a chip, configured for use with surface plasmon resonance to determine binding kinetics. An example of such a chip is a CM5 Sensor S chip (GE Healthcare; Piscatawany, N.J). The system may provide instrumentation such as a surface plasmon resonance instrument. The system may provide streptavidin and/or biotin. Optionally, the system provides biotin-DNA, DNA ligase, buffers, and/or DNA polymerase for preparation of biotinylated template DNA. Optionally, the system provides a gel or reagents (e.g., phenol:chloroform) for biotinylated DNA purification. Alternatively, the system provides reagents for biotinylated template DNA characterization, for example, mass spectrometry or HPLC. Optionally, the system includes streptavidin, a chip, reagents, instrumentation, and/or instructions for immobilization of streptavidin on a chip. Optionally, a chip is provided in the system already configured for template DNA coating, wherein the chip is immobilized with a reagent capable of binding template nucleic acids or modified template nucleic acids (e.g., biotinylated template DNA). Optionally, the system provides reagents for chip regeneration.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanoparticle. Optionally, the system includes one or more reagents and instructions necessary to bind template DNA molecules onto a nanoparticle. The nanoparticle may be configured for the electrochemical detection of nucleic acid-polymerase interaction, for instance, by using gold nanoparticles. Optionally, the DNA-nanoparticle conjugates are formed between aqueous gold colloid solutions and template DNA molecules including, for example, free thiol or disulfide groups at their ends. The conjugates may include same nucleic acid sequence. Optionally, the nanoparticle conjugates are stabilized against flocculation and precipitation at high temperature (e.g., greater than 60° C.) and high ionic strength (e.g., 1M $Na^+$). Optionally, the system provides reagents for preparing template DNA molecules for nanoparticle attachment, including, generating template DNA molecules with disulfides or thiols. Disulfide-containing template nucleic acids may be synthesized using, for example, a 3'-thiol modifier controlled-pore glass (CPG) or by beginning with a universal support CPG and adding a disulfide modifier phosphoramidite as the first monomer in the sequence. The system may provide nucleic acid synthesis reagents and/or instructions for obtaining disulfide-modified template nucleic acids. Thiol-containing template nucleic acids may also be generated during nucleic acid synthesis with a 5'-tritylthiol modifier phosphoramidite. The system may provide reagents and/or instructions for nanoparticle conjugate purification using for example, electrophoresis or centrifugation. Optionally, nanoparticle conjugates are used to monitor polymerase-template nucleic acid interactions colorimetrically. In this instance, the melting temperature of the nanoparticle conjugate increases in the presence of strong polymerase binding. Therefore, the strength of DNA binding can be determined by the change in this melting transition, which is observable by a color change. The systems optionally include reagents and equipment for detection of the melting transition.

Also provided is a system for performing one or more steps of any sequencing method disclosed herein. Optionally, the system includes components and reagents necessary to perform a polymerase and template nucleic acid binding assay in the presence of nucleotides, using a detectable polymerase. Optionally, the polymerase is detectably labeled. Optionally, the polymerase is detected using intrinsic properties of the polymerase, for example, aromatic amino acids. Optionally, the polymerase and template nucleic acids present in the system are configured for use in solution, without conjugation to a support. The detectable label on the polymerase may be a fluorophore, wherein fluorescence is used to monitor polymerase-template nucleic acid binding events. Optionally, the detectable polymerase may be used in combination with template nucleic acids in solution, or template nucleic acids conjugated to a support structure. Optionally, one or more cysteine residues of the polymerase is labeled with Cy3-maleimide. Optionally, the system includes reagents and/or instructions necessary to prepare fluorescently labeled polymerase molecules. The system may include reagents and/or instructions for purification of fluorescently labeled polymerases.

Procedural Features of the Methods

Following the examination step, where the identity of the next base has been identified via formation of a closed-complex, the reaction conditions may be reset, recharged, or modified as appropriate, in preparation for the optional incorporation step or an additional examination step. Optionally, the identity of the next base has been identified without chemically incorporating a nucleotide. Optionally, the identity of the next base is identified with chemical incorporation of a nucleotide, wherein a subsequent nucleotide incorporation has been inhibited. Optionally, all components of the examination step, excluding the template nucleic acid being sequenced, are removed or washed away, returning the system to the pre-examination condition. Optionally, partial components of the examination step are removed. Optionally, additional components are added to the examination step.

Optionally, reversible terminator nucleotides are used in the incorporation step to ensure one, and only one nucleotide is incorporated per cycle. No labels are required on the reversible terminator nucleotides as the base identity is known from the examination step. Non-fluorescently labeled reversible terminators are readily available from commercial suppliers. Non-labeled reversible terminator nucleotides are expected to have much faster incorporation kinetics compared to labeled reversible terminators due to their smaller steric footprint, and similar size to natural nucleotides.

Disclosed herein, in part, are reagent cycling sequencing methods, wherein sequencing reagents are introduced, one after another, for every cycle of examination and/or incorporation. Optionally, the sequencing reaction mixture includes a polymerase, a primed template nucleic acid, and at least one type of nucleotide. Optionally, the nucleotide and/or polymerase are introduced cyclically to the sequencing reaction mixture. Optionally, the sequencing reaction mixture includes a plurality of polymerases, primed template nucleic acids, and nucleotides. Optionally, a plurality of nucleotides and/or a plurality of polymerases are introduced cyclically to the sequencing reaction mixture. Optionally, the examination step of the sequencing reaction has a different composition than the incorporation step of the sequencing reaction.

Optionally, one or more nucleotides are sequentially added to and removed from the sequencing reaction. Optionally, 1, 2, 3, 4, or more types of nucleotides are added to and removed from the reaction mixture. For example, one type of nucleotide is added to the sequencing reaction, removed, and replaced by another type of nucleotide. Optionally, a nucleotide type present during the examination step is different from a nucleotide type present during the incorporation step. Optionally, a nucleotide type present during one examination step is different from a nucleotide type present during a sequential examination step (i.e., the sequential examination step is performed prior to an incorporation step). Optionally, 1, 2, 3, 4 or more types of nucleotides are present in the examination reaction mixture and 1, 2, 3, 4, or more types of nucleotides are present in the incorporation reaction mixture.

Optionally, a polymerase is cyclically added to and removed from the sequencing reaction. One or more different types of polymerases may be cyclically added to and removed from the sequencing reaction. Optionally, a polymerase type present during the examination step is different from a polymerase type present during the incorporation step. A polymerase type present during one examination step may be different from a polymerase type present during a sequential examination step (i.e., the sequential examination step is performed prior to an incorporation step).

Optionally, conditions such as the presence of reagents, pH, temperature, and ionic strength are varied throughout the sequencing reaction. Optionally, a metal is cyclically added to and removed from the sequencing reaction. For example, a catalytic metal ion may be absent during an examination step and present during an incorporation step. Alternatively, a polymerase inhibitor may be present during an examination step and absent during an incorporation step. Optionally, reaction components that are consumed during the sequencing reaction are supplemented with the addition of new components at any point during the sequencing reaction.

Nucleotides can be added one type at a time, with the polymerase, to a reaction condition that favors closed-complex formation. The polymerase binds only to the template nucleic acid if the next correct nucleotide is present. A wash step after every nucleotide addition ensures all excess polymerases and nucleotides not involved in a closed-complex are removed from the reaction mixture. If the nucleotides are added one at a time, in a known order, the next base on the template nucleic acid is determined by the formation of a closed-complex when the added nucleotide is the next correct nucleotide. The closed-complex may be identified by both the conformational change and the increased stability of the polymerase-template nucleic acid-nucleotide interaction. Optionally, the stability of the closed-complex formed in the presence of the next correct nucleotide is at least an order of magnitude greater than the unstable interactions of the polymerase with the template nucleic acid in the presence of incorrect nucleotides. The use of a wash step ensures that there are no unbound nucleotides and polymerases and that the only nucleotides present in the reaction are those sequestered in a closed-complex with a polymerase and a template nucleic acid. Once the next base on the template nucleic acid is determined, the next correct nucleotide sequestered in the closed-complex may be incorporated by flowing in reaction conditions that favor dissociation or destabilization of the closed-complex and extending the template nucleic acid primer strand by one base (incorporation). Therefore, the wash step ensures that the only nucleotide incorporated is the next correct nucleotide from the closed-complex. This reagent cycling method may be repeated and the nucleic acid sequence determined. This reagent cycling method may be applied to a single template nucleic acid molecule, or to collections of clonal populations such as PCR products or rolling-circle amplified DNA. Many different templates can be sequenced in parallel if they are arrayed, for instance, on a solid support. Optionally, the wash step destabilizes binary complex formation. Optionally, the washing is performed for a duration of time that ensures that the binary complex is removed, leaving the stabilized closed-complex in the reaction mixture. Optionally, the wash step includes washing the reaction with a high ionic strength or a high pH solution.

Optionally, the incorporation step is a three stage process. In the first stage, all four nucleotide types are introduced into a reaction including a primed template nucleic acid, with a high fidelity polymerase, in reaction conditions which favor the formation of a closed-complex, and the next correct nucleotides are allowed to form stable closed-complexes with the template nucleic acid. In a second stage, excess nucleotides and unbound polymerase are washed away. In a third stage, reaction conditions are modified so that the closed-complex is destabilized and the sequestered nucleotides within the closed-complex become incorporated into the 3'-end of the template nucleic acid primer. In an alternative approach, the second stage is modified to remove completely any of the high-fidelity polymerase and cognate nucleotide that may have been present in the closed-complex, and the removed components are then replaced with a second polymerase and one or more nucleotides (e.g., reversible terminator nucleotides). Formation of tight polymerase-nucleic acid complexes in the incorporation step can be enabled by standard techniques such as fusing a non-specific DNA binding domain to the polymerase (e.g., the Phusion polymerase, which is available from Thermo Fisher Scientific; Waltham, Mass.), and utilizing high concentrations of nucleotides to ensure correct nucleotides are always present in the closed-complex.

Polymerase molecules bind to primed template nucleic acid molecules in a fingers-closed conformation in the presence of the next correct nucleotide even in the absence of divalent metal ions that are typically required for polymerase synthesis reactions. The conformational change traps the nucleotide complementary to the next template base within the active site of the polymerase. Optionally, the formation of the closed-complex may be used to determine the identity of next base on the template nucleic acid. Optionally, the primed template nucleic acids may be contacted serially by different nucleotides in the presence of polymerase, in the absence of catalytic divalent metal ions; wherein the formation of a closed-complex indicates the nucleotide currently in contact with the template nucleic acid is the complementary nucleotide to the next base on the nucleic acid. A known order of nucleotides (in the presence of polymerase and absence of catalytic metal ions) brought into contact with the template nucleic acid ensures facile identification of the complementary nucleotide based on the particular position in the order that induces closed-complex formation. Optionally, an appropriate wash step may be performed after every nucleotide addition to ensure removal of all excess enzymes and nucleotides, leaving behind only the polymerase that is bound to nucleic acids in a closed-complex with the next correct nucleotide at the active site. The closed-complex may be identified by means that reveal the conformational change of the polymerase in the closed conformation or by means that reveal the increased stability of the polymerase/nucleic-acid/next-correct-nucleotide complex compared to binary polymerase-nucleic acid complexes or compared to unstable interactions between the polymerase, primed template nucleic acid and incorrect nucleotides.

Optionally, the process of identifying the next complementary nucleotide (examination step) includes the steps of contacting immobilized primed template nucleic acids with an examination mixture including polymerase and nucleotides of one kind under conditions that inhibit the chemical incorporation of the nucleotide, removing unbound reagents by a wash step, detecting the presence or absence of polymerase closed-complex on the immobilized nucleic acids, and repeating these steps serially, with nucleotides of different kinds until a closed-complex formation is detected. The closed-complex may be identified by both the conformational change and the increased stability of the polymerase/nucleic-acid/next-correct-nucleotide complex. The wash step between successive nucleotide additions may be eliminated by the use of detection mechanisms that can detect the formation of the closed-complex with high fidelity, for instance, evanescent wave sensing methods or methods that selectively monitor signals from the closed-complex. The examination steps noted above may be followed by an incorporation step including, contacting the closed-complex with catalytic metal ions to covalently add the nucleotide sequestered in the closed-complex to the 3'-end of the primer. Optionally, the incorporation step may include, contacting the immobilized nucleic acids with a pre-incorporation mixture including a combination of multiple types of nucleotides and polymerase under conditions that inhibit the chemical incorporation of the nucleotides; wherein the pre-incorporation mixture may contain additives and solution conditions to ensure highly efficient closed-complex formation (e.g., low-salt conditions). The methods may also include performing a wash step to remove unbound reagents and providing the immobilized complexes with an incorporation mixture, including catalytic metal ions, to chemically incorporate nucleotides sequestered within the active site of the polymerase. The pre-incorporation mixture ensures highly efficient closed-complex formation, while the wash step and incorporation mixture ensure the addition of a single nucleotide to the 3'-end of the primer. Optionally, the incorporation step may occur directly after examination an addition of one type of nucleotide. For instance, a repeated pattern used for sequencing may include the following flow pattern (i) dATP+/polymerase, (ii) Wash, (iii) $Mg^{2+}$, (iv) Wash, (v) dTTP+/polymerase, (vi) Wash, (vii) $Mg^{2+}$, (viii) Wash, (ix) dCTP+/polymerase, (x) Wash (xi) $Mg^{2+}$, (xii) Wash, (xiii) dGTP+/polymerase, (xiv) Wash, (xv) $Mg^{2+}$, (xvi) Wash. Optionally, the repeated pattern used for sequencing may include (i) dATP+/polymerase, (ii) Wash, (iii) dTTP+/polymerase, (iv) Wash, (v) dGTP+/polymerase, (vi) Wash, (vii) dCTP+/polymerase, (viii) Wash, (ix) Pre-incorporation mixture, (x) Wash, (xi) Mg, (xii) Wash. The wash steps typically contain metal ion chelators and other small molecules to prevent accidental incorporations during the examination steps. After the incorporation step, the primer strand is typically extended by one base. Repeating this process, sequential nucleobases of a nucleic acid may be identified, effectively determining the nucleic acid sequence. Optionally, the examination step is performed at high salt conditions, for example, under conditions of 50 mM to 1,500 mM salt (e.g., a salt providing monovalent cations).

For sequencing applications, it can be advantageous to minimize or eliminate fluidics and reagents exchange. Removing pumps, valves and reagent containers can allow for simplified manufacturing of smaller devices. Disclosed herein, in part, are "all-in" sequencing methods, wherein the need to introduce reagents one after another, for every cycle of examination and/or incorporation, is eliminated. Reagents are added only once to the reaction, and sequencing-by-synthesis is performed by manipulating reagents already enclosed within the sequencing reaction. A scheme such as this requires a method to distinguish different nucleotides, a method to synchronize incorporation of nucleotides across a clonal population of nucleic acids and/or across different nucleic acid molecules, and a method to ensure only one nucleotide is added per cycle.

Optionally, the sequencing reaction mixture includes a polymerase, a primed template nucleic acid, and at least one type of nucleotide. Optionally, the sequencing reaction mixture includes a plurality of polymerases, primed template nucleic acids, and nucleotides. As provided herein, a polymerase refers to a single polymerase or a plurality of polymerases. As provided herein, a primed template nucleic acid or template nucleic acid refers to a single primed template nucleic acid or single template nucleic acid, or a plurality of primed template nucleic acids or a plurality of template nucleic acids. As provided herein, a nucleotide refers to one nucleotide or a plurality of nucleotides. As provided herein, a single nucleotide is one nucleotide. Optionally, the sequencing reaction nucleotides include, but are not limited to, 1, 2, 3, or 4 of the following nucleotides: dATP, dGTP, dCTP, dTTP, and dUTP.

Optionally, the examination step and the incorporation step take place in a single sequencing reaction mixture.

Optionally, 1, 2, 3, 4 or more types of nucleotides (e.g., dATP, dGTP, dCTP, dTTP) are present in the reaction mixture together at the same time, wherein one type of nucleotide is a next correct nucleotide. The reaction mixture further includes at least one polymerase and at least one primed template nucleic acids. Optionally, the template nucleic acid is a clonal population of template nucleic acids. Optionally, the polymerase, primed template nucleic acid, and the nucleotide form a closed-complex under examination reaction conditions.

In the provided methods, four types of nucleotides can be present at distinct and different concentrations wherein the diffusion and binding times of the polymerase to the template nucleic acid are different for each of the four nucleotides, should they be the next correct nucleotide, due to the different concentrations of the four nucleotides. For example, the nucleotide at the highest concentration would bind to its complementary base on the template nucleic acid at a fast time, and the nucleotide at the lowest concentration would bind to its complementary base on the template nucleic acid at a slower time; wherein binding to the complementary base on the template nucleic acid refers to the polymerase binding to the template nucleic acid with the next correct nucleotide in a closed closed-complex. The identity of the next correct nucleotide is therefore determined by monitoring the rate or time of binding of polymerase to the template nucleic acid in a closed-complex. Optionally, the four types of nucleotides may be distinguished by their concentration, wherein the different concentrations of the nucleotides result in measurably different on-rates for the polymerase binding to the nucleic acid. Optionally, the four types of nucleotides may be distinguished by their concentration, wherein the different concentrations of the nucleotides result in measurably different on-rates for the formation of a stabilized closed-complex.

Optionally, the polymerase is labeled. In some instances, the polymerase is not labeled (i.e., does not harbor an exogenous label, such as a fluorescent label) and any label-free detection method disclosed herein or known in the art is employed. Optionally, the binding of the polymerase to the nucleic acid is monitored via a detectable feature of the polymerase. Optionally, the formation of a stabilized closed-complex is monitored via a detectable feature of the polymerase. A detectable feature of the polymerase may include, but is not limited to, optical, electrical, thermal, colorimetric, mass, and any combination thereof.

Optionally, 1, 2, 3, 4, or more nucleotides types (e.g., dATP, dTTP, dCTP, dGTP) are tethered to 1, 2, 3, 4, or more different polymerases; wherein each nucleotide type is tethered to a different polymerase and each polymerase has a different exogenous label or a detectable feature from the other polymerases to enable its identification. All tethered nucleotide types can be added together to a sequencing reaction mixture forming a closed-complex including a tethered nucleotide-polymerase; the closed-complex is monitored to identify the polymerase, thereby identifying the next correct nucleotide to which the polymerase is tethered. The tethering may occur at the gamma phosphate of the nucleotide through a multi-phosphate group and a linker molecule. Such gamma-phosphate linking methods are standard in the art, where a fluorophore is attached to the gamma phosphate linker. Optionally, different nucleotide types are identified by distinguishable exogenous labels. Optionally, the distinguishable exogenous labels are attached to the gamma phosphate position of each nucleotide.

Optionally, the sequencing reaction mixture includes a catalytic metal ion. Optionally, the catalytic metal ion is available to react with a polymerase at any point in the sequencing reaction in a transient manner. To ensure robust sequencing, the catalytic metal ion is available for a brief period of time, allowing for a single nucleotide complementary to the next base in the template nucleic acid to be incorporated into the 3'-end of the primer during an incorporation step. In this instance, no other nucleotides, for example, the nucleotides complementary to the bases downstream of the next base in the template nucleic acid, are incorporated. Optionally, the catalytic metal ion magnesium is present as a photocaged complex (e.g., DM-Nitrophen) in the sequencing reaction mixture such that localized UV illumination releases the magnesium, making it available to the polymerase for nucleotide incorporation. Furthermore, the sequencing reaction mixture may contain EDTA, wherein the magnesium is released from the polymerase active site after catalytic nucleotide incorporation and captured by the EDTA in the sequencing reaction mixture, thereby rendering magnesium incapable of catalyzing a subsequent nucleotide incorporation.

Thus, in the provided methods, a catalytic metal ion can be present in a sequencing reaction in a chelated or caged form from which it can be released by a trigger. For example, the catalytic metal ion catalyzes the incorporation of the closed-complex next correct nucleotide, and, as the catalytic metal ion is released from the active site, it is sequestered by a second chelating or caging agent, disabling the metal ion from catalyzing a subsequent incorporation. The localized release of the catalytic metal ion from its cheating or caged complex is ensured by using a localized uncaging or un-chelating scheme, such as an evanescent wave illumination or a structured illumination. Controlled release of the catalytic metal ions may occur for example, by thermal means. Controlled release of the catalytic metal ions from their photocaged complex may be released locally near the template nucleic acid by confined optical fields, for instance by evanescent illumination such as waveguides or total internal reflection microscopy. Controlled release of the catalytic metal ions may occur for example, by altering the pH of the solution near the vicinity of the template nucleic acid. Chelating agents such as EDTA and EGTA are pH dependent. At a pH below 5, divalent cations $Mg^{2+}$ and $Mn^{2+}$ are not effectively chelated by EDTA. A method to controllably manipulate the pH near the template nucleic acid allows the controlled release of a catalytic metal ion from a chelating agent. Optionally, the local pH change is induced by applying a voltage to the surface to which the nucleic acid is attached. The pH method offers an advantage in that that metal goes back to its chelated form when the pH is reverted back to the chelating range.

Optionally, a catalytic metal ion is strongly bound to the active site of the polymerase, making it necessary to remove the polymerase from the template nucleic acid after a single nucleotide incorporation. The removal of polymerase may be accomplished by the use of a highly distributive polymerase, which falls off the 3'-end of the strand being synthesized (e.g., primer) after the addition of every nucleotide. The unbound polymerase may further be subjected to an electric or magnetic field to remove it from the vicinity of the nucleic acid molecules. Any metal ions bound to the polymerase may be sequestered by chelating agents present in the sequencing reaction mixture, or by molecules which compete with the metal ions for binding to the active site of the polymerase without disturbing the formation of the closed-complex. The forces which remove or move the polymerase away from the template nucleic acid (e.g., electric field, magnetic field, and/or chelating agent) may be terminated, allowing for the polymerase to approach the template nucleic acid for another round of sequencing (i.e., examination and incorporation). The next round of sequencing, in a non-limiting example, includes the formation of a closed-complex, removing unbound polymerase away from the vicinity of the template nucleic acid and/or closed-complex, controlling the release of a catalytic metal ion to incorporate a single nucleotide sequestered within the closed-complex, removing the polymerase which dissociates from the template nucleic acid after single incorporation away from the vicinity of the template nucleic acid, sequestering any free catalytic metal ions through the use of chelating agents or competitive binders, and allowing the polymerase to approach the template nucleic acid to perform the next cycle of sequencing.

Described above are polymerase-nucleic acid binding reactions for the identification of a nucleic acid sequence. However, nucleic acid sequence identification may include information regarding nucleic acid modifications, including methylation and hydroxymethylation. Methylation may occur on cytosine bases of a template nucleic acid. DNA methylation may stably alter the expression of genes. DNA methylation is also indicated in the development of various types of cancers, atherosclerosis, and aging. DNA methylation therefore can serve as an epigenetic biomarker for human disease.

Optionally, one or more cytosine methylations on a template nucleic acid are identified during the sequencing by binding methods provided herein. The template nucleic acid may be clonally amplified prior to sequencing, wherein the amplicons include the same methylation as their template nucleic acid. Amplification of the template nucleic acids may include the use of DNA methyltransferases to achieve amplicon methylation. The template nucleic acids or amplified template nucleic acids are provided to a reaction mixture including a polymerase and one or more nucleotide types, wherein the interaction between the polymerase and nucleic acids is monitored. Optionally, the interaction between the polymerase and template nucleic acid in the presence of a methylated cytosine is different than the interaction in the presence of an unmodified cytosine. Therefore, based on examination of a polymerase-nucleic acid interaction, the identity of a modified nucleotide is determined.

Optionally, following one or more examination and/or incorporation steps, a subset of nucleotides is added to reduce or reset phasing. Thus, the methods can include one or more steps of contacting a template nucleic acid molecule being sequenced with a composition comprising a subset of nucleotides and an enzyme for incorporating the nucleotides into the strand opposite the template strand of the nucleic acid molecule. The contacting can occur under conditions to reduce phasing in the nucleic acid molecule. Optionally, the step of contacting the template nucleic acid molecule occurs after an incorporation step and/or after an examination step. Optionally, the contacting occurs after 1, 2, 3, 4, 5, 6, 7, 8, 9, 10, 15, 20, 25, 30, 35, 40, 45, 50, 60, 65, 70, 75, 80, 85, 90, 95, or 100 rounds or more of sequencing, i.e., rounds of examination and incorporation. Optionally, the contacting occurs after 30 to 60 rounds of sequencing. Optionally, the contacting occurs after every round of sequencing (i.e., after one set of examination and incorporation steps). Optionally, multiple contacting steps occur after every round of sequencing, wherein each contacting step may comprise different subsets of nucleotides. Optionally, the method further comprises one or more washing steps after contacting. Optionally, the subset comprises two or three nucleotides. Optionally, the subset comprises three nucleotides. Optionally, the subset of nucleotides is selected from three of dATP, dGTP, dCTP, dTTP or a derivative thereof. Optionally, the three nucleotides comprise adenosine, cytosine, and guanine. Optionally, the three nucleotides comprise adenosine, cytosine, and thymine. Optionally, the three nucleotides comprise cytosine, guanine and thymine. Optionally, the three nucleotides comprise adenosine, guanine and thymine. Optionally, each round of contacting comprises the same subset or different subsets of nucleotides. Optionally, sequencing of a nucleic acid template is monitored and the contacting with the subset of nucleotides occurs upon detection of phasing. See also for example, U.S. Pat. No. 8,236,532, which is incorporated herein by reference in its entirety.

Optionally, the sequencing reaction involves a plurality of template nucleic acids, polymerases and/or nucleotides, wherein a plurality of closed-complexes is monitored. Clonally amplified template nucleic acids may be sequenced together wherein the clones are localized in close proximity to allow for enhanced monitoring during sequencing. Optionally, the formation of a closed-complex ensures the synchronicity of base extension across a plurality of clonally amplified template nucleic acids. The synchronicity of base extension allows for the addition of only one base per sequencing cycle.

EXAMPLES

The following Example demonstrates how monitored destabilization of ternary complexes can be used in a sequencing-by-binding procedure. Ternary complexes were prepared using a primed template nucleic acid molecule, a polymerase, and a plurality of nucleotides. Wash steps that progressively omitted nucleotides, one at a time, were used to identify cognate and non-cognate nucleotides without incorporation of any nucleotide into the primer. In this Example, polymerase was omitted from the wash buffer. Optionally, polymerase can be included in the wash buffer with similarly good results. Identification of cognate and non-cognate nucleotides was based on assessment of formation and/or maintenance of ternary complexes. A single incorporation step employing reversible terminator nucleotides facilitated single nucleotide incorporation. A first polymerase was used for conducting the examination step with native nucleotides, and a second polymerase was used in the incorporation step. The reversible terminator moiety of the blocked primer was removed by chemical treatment prior to the next examination step. All steps were repeated in a cyclical fashion.

Example 1 describes a procedure wherein cognate nucleotides of ternary complexes were identified by dissociation of those ternary complexes, without incorporation of any nucleotide into the primer of the primed template nucleic acid. More particularly, ternary complexes were destabilized when washed with a buffer that did not include the cognate nucleotide.

Example 1

Sequencing-by-Binding Using Monitored Dissociation of a Ternary Complex

A FORTEBIO® (Menlo Park, Calif.) Octet instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid onto fiber optic tips functionalized with streptavidin (SA) according to standard procedures. Four different template sequences (i.e., wildtype, G12C, G12R, and G13D) were used to demonstrate interrogation of mutations in codons 12 and 13 of the KRAS sequence. Template sequences and targets were selected to exemplify detection of each of four different nucleotides by the procedure. Two different positions in the wildtype (WT) sequence were used for making comparisons. Relevant sequences were as follows, where underlining identifies the base position being interrogated.

| Codon 12 | |
|---|---|
| Wildtype | GGT |
| G12C | TGT |
| G12R | CGT |
| Codon 13 | |
| Wildtype | GGC |
| G13D | GAC |

Tips were washed in a buffered solution that included 30 mM Tris (pH 8.0), 220 mM KCl, 160 mM potassium glutamate, and 0.01% Tween-20 before commencing the cycling protocol. A ternary complex was formed by contacting the immobilized primed template nucleic acid with a buffered solution that included a polymerase and the combination of four native dNTPs (dTTP, dGTP, dCTP, dATP), each of the dNTPs being present at a concentration of 100 µM, for a period of about 30-100 seconds at 37° C. Polymerases used in the procedure were either Bst 2.0 (NEB; Ipswich, Mass.) at 360 U/ml, or Bsu DNA polymerase large fragment (New England BioLabs; Ipswich, Mass.) at 136 U/ml. The solution used for preparing ternary complexes further included 30 mM Tris-HCl (pH 8.0), 220 mM KCl, 160 mM potassium glutamate, 0.01% Tween-20, 1 mM β-mercaptoethanol, and 2 mM $SrCl_2$.

Cognate and non-cognate nucleotides were identified by observing the dissociation of a ternary complex following a series of wash steps. All wash solutions used in the procedure included 30 mM Tris-HCl (pH 8.0), 220 mM KCl, 160 mM potassium glutamate, 2 mM $SrCl_2$, 0.01% Tween-20, 1 mM β-mercaptoethanol. Nucleotides, when present, were included at concentrations of 100 µM each. Tips were first washed for 5-20 seconds using a buffered solution that included three dNTPs (dGTP, dCTP, and dATP) while omitting one dNTP (dTTP) from the collection used to produce the ternary complex. Tips were next washed for 5-20 seconds in a buffered solution that included two dNTPs (dCTP, dATP) while omitting one dNTP (dGTP) from the collection used in the previous wash. Tips were next washed for 5-20 seconds in a buffered solution that included one dNTP (dATP) while omitting one dNTP (dCTP) from the collection used in the previous wash. Tips were finally washed for 5-20 seconds in a buffered solution that did not include any dNTP, again being consistent with the pattern of omitting the single nucleotide (dATP) that had been included in the previous wash step. While not used in this procedure, the initial wash step optionally can employ the complete set of nucleotides used for preparing the ternary complex (e.g., all four dNTPs in this Example).

Figure 2:
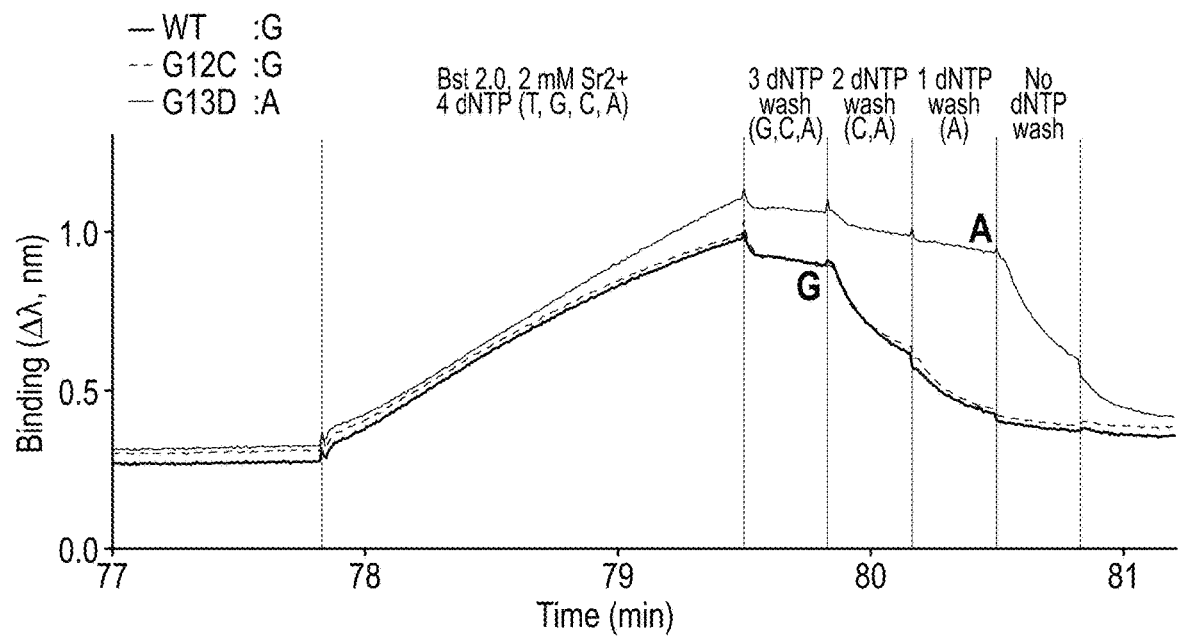
FIG. 2 is an interferometry trace for interrogation of the second base of codon 13 in KRAS WT (GGC) and G13D (GAC) sequences. Two different correct bases are shown at the same position for the two different template nucleic acids. The next correct nucleotides harboring the correct bases are highlighted in bold.

Results presented in FIGS. 1 and 2 illustrate sequencing runs carried out using the protocol described above. FIG. 1 shows examination traces for the nucleotide mutation at codon 12 (GGT), which ordinarily encodes glycine (WT). The first G in this codon can be mutated to T or C, which results in codons encoding cysteine (G12C) or arginine (G12R), respectively. Ternary complexes were first generated in the presence of all 4 dNTPs (dTTP, dGTP, dCTP, dATP) using each different primed template nucleic acid. Complexes were subsequently washed using a buffer that included three dNTPs (dGTP, dCTP, dATP), but not dTTP. Ternary complexes dissociated and the binding signal was lost when the cognate base was a T (as in G12C). As shown in FIG. 1, the observed dissociation was specific for omission of the cognate nucleotide, meaning that other ternary complexes (e.g., including primed template nucleic acids for templates G12R and WT) remained intact when the wash buffer included dGTP, dCTP, and dATP. When nucleotides present in the next wash were limited to dCTP and dATP, there was substantially no further reduction in the binding signal for the G12C trial, because the ternary complex already had dissociated. However, the ternary complex that included the WT primed template nucleic acid dissociated and the binding signal was lost since dGTP had been omitted from the wash buffer, and since dGTP was the cognate nucleotide in that example. Again the cognate nucleotide of the WT template was identified by dissociation of the ternary complex that included that nucleotide. When the wash buffer included only dATP and not dCTP, the ternary complex that included G12R dissociated, thereby identifying dCTP as the cognate nucleotide for that complex. Finally, a wash buffer that did not include any of the four nucleotides showed no further signal reductions for any of the three templates shown in FIG. 1. FIG. 2 shows examination traces for codon 13 (GGC), which ordinarily encodes glycine (WT), but which can be mutated to encode aspartate (G13D) by changing the second position of the codon to an A (i.e., GAC). When the cognate dGTP nucleotide was omitted from the wash buffer, ternary complexes that included the WT primed template nucleic acid dissociated and binding signal was lost. Likewise, elimination of the cognate dATP nucleotide from the wash buffer (i.e., the final wash buffer that did not include any dNTP) led to dissociation of ternary complexes that included the G13D primed template nucleic acid.

Taken together, the results presented in FIGS. 1 and 2 confirmed that a nucleotide that included a base complementary to the next base of a template strand immediately downstream of the primer in a primed template nucleic acid could be identified by a process that involved monitoring dissociation of ternary complexes. More specifically, dissociation of a ternary complex indicated that the cognate nucleotide had been eliminated from the complex. On the other hand, persistence of a ternary complex in the absence of a test nucleotide indicated the test nucleotide was not the cognate nucleotide. Notably, monitoring optionally can involve assessment of binding signals at the start and finish of the individual steps (i.e., endpoint monitoring).

Described below is an approach employing initial formation of nucleotide-independent binary complexes, followed by addition of nucleotides to produce ternary complexes. Complexes formed in the procedure were subjected to a series of wash steps, during which time ternary complex maintenance and dissociation was monitored. For example, binary complexes that included primed template nucleic acid and polymerase can be contacted with a reaction mixture including four native nucleotides. Serial washes (e.g., using 3, 2, 1, and 0 nucleotides) can be used with monitoring to establish when nucleotide-specific ternary complexes dissociate. The nucleotide required to maintain integrity of the ternary complex (i.e., the nucleotide that, when removed, causes dissociation of the complex) corresponds to the cognate nucleotide. The following Example illustrates the technique using binding of two nucleotides, rather than four nucleotides to form ternary complexes. Two sets of two nucleotides were required to test the full complement of four dNTPs. By this approach, only one of the two sets of two nucleotides for each primed template nucleic acid formed a ternary complex. The other set of two nucleotides, which did not include the cognate nucleotide, did nothing to modify the binary complex. Results presented below evidenced the distinction between sets of nucleotides capable of forming ternary complexes, and sets of nucleotides that did not alter the preformed nucleotide-independent binary complexes.

Example 2 describes a procedure wherein cognate nucleotides corresponding to each of dATP, dTTP, dGTP, and dCTP were identified by a process involving initial formation of binary complexes, followed by monitoring of formation and/or dissociation of ternary complexes. Notably, failure to detect a ternary complex in the presence of a plurality of nucleotides indicated that none of the nucleotides among the plurality corresponded to the cognate nucleotide.

Example 2

Preliminary Formation of Binary Complexes Followed by Formation and Dissociation of Ternary Complexes Identifies Cognate and Non-Cognate Nucleotides A FORTEBIO® (Menlo Park, Calif.) Octet instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid onto fiber optic tips functionalized with streptavidin (SA) according to standard procedures. Four different template sequences (i.e., wildtype, G12C, G12R, and G13D) were used to demonstrate interrogation of mutations in codons 12 and 13 of the KRAS sequence. Template sequences and targets were selected to exemplify detection of each of four different nucleotides by the invented procedure. Two different positions in the wildtype (WT) sequence were used for making comparisons. Relevant sequences were as follows, where underlining identifies the base position being interrogated.

| Codon 12 | |
|---|---|
| Wildtype | GGT |
| G12C | TGT |
| G12R | CGT |

| Codon 13 | |
|---|---|
| Wildtype | GGT |
| G13D | GAC |

Tips were washed in a buffered solution containing 200 mM KCl, 160 mM potassium glutamate, and 0.01% Tween-20 before commencing the cycling protocol. Nucleotide-independent binary complexes were formed by contacting tips harboring immobilized primed template nucleic acid with a solution that included 30 mM Tris-HCl (pH 8.0), 220 mM KCl, 160 mM potassium glutamate, 2 mM SrCl$_2$, 0.01% Tween-20, 1 mM β-mercaptoethanol, and Bst 2.0 (NEB; Ipswich, Mass.) DNA polymerase, but that did not include any added nucleotide. Next, the enzyme-containing solution was replaced with a second reaction mixture that included dTTP and dGTP, each at a concentration of 100 μM, to permit nucleotide binding and ternary complex formation if either nucleotide corresponded to the cognate nucleotide. The nucleotide-containing solution further included 30 mM Tris-HCl (pH 8.0), 220 mM KCl, 160 mM potassium glutamate, 0.01% Tween-20, 1 mM β-mercaptoethanol, and 2 mM SrCl$_2$. An optional wash step was conducted using a buffer that included all (i.e., two) of the nucleotides used in the nucleotide binding step. Next, tips were washed with a buffer that omitted one of the nucleotides (dTTP) from the previous wash step. Any polymerase and nucleotide remaining in ternary complexes were removed with 30 mM Tris-HCl (pH 8.0), 320 mM KCl, 20 mM EDTA, 0.01% Tween-20, 1 mM β-mercaptoethanol. Optionally, an additional wash step could have been included immediately before the wash that removed nucleotide and ternary complexes to permit dissociation of residual ternary complexes by the same mechanism used for nucleotide interrogation (i.e., omission of cognate nucleotide from the buffer used for examination). The process was repeated using the remaining two nucleotides (i.e., dCTP and dATP) in place of the first set of nucleotides, and using appropriate wash buffers according to the cycling intervals indicated in FIGS. 3A-3D.

Results of the procedure are illustrated in FIGS. 3A-3D. In all instances, results illustrate a two-part procedure wherein binary complexes were formed before contacting nucleotides. Binary complexes were contacted with the first two nucleotides (dTTP and dGTP) to investigate possible ternary complex formation. Complexes were then subjected to wash steps that progressively omitted one of the nucleotides being tested for the ability to promote ternary complex formation. The second part of the procedure repeated the first part while substituting the remaining two nucleotides (dCTP and dATP) in place of the first two nucleotides.

Figure 3A:
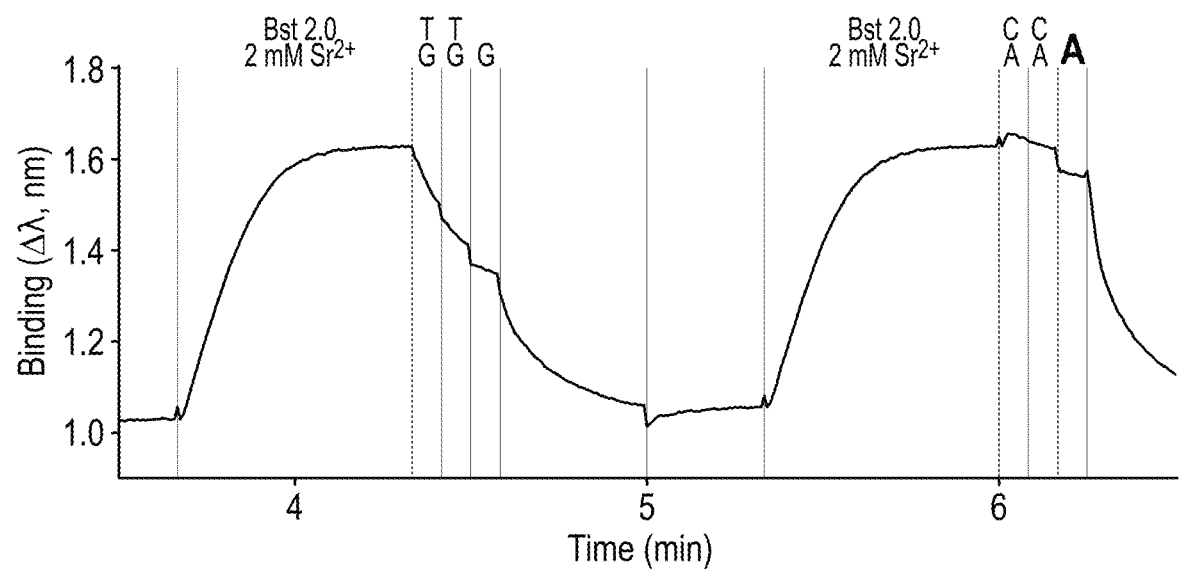
FIGS. 3A-3D are interferometry traces for the double interrogation protocol, wherein binary complexes formed between the primed template nucleic acid molecule and polymerase were contacted with a plurality of nucleotides in the absence of polymerase. The next correct nucleotides harboring correct bases are highlighted in bold. The next correct nucleotide for the trace shown in FIG. 3A is dATP. The next correct nucleotide for the trace shown in FIG. 3B is dTTP. The next correct nucleotide for the trace shown in FIG. 3C is dGTP. The next correct nucleotide for the trace shown in FIG. 3D is dCTP.

FIG. 3A shows results obtained in a system wherein the next correct nucleotide was dATP. Binary complexes formed between the primed template nucleic acid and polymerase were contacted with a solution that included dTTP and dGTP, but did not include polymerase to maintain binary complexes in the absence of cognate nucleotide. Binding signal decreased immediately and steadily after washes that included dTTP and dGTP, or dGTP alone. The failure to increase or even maintain the binding signal indicated that a ternary complex did not form. The absence of ternary complex formation indicated that neither dTTP nor dGTP was the cognate nucleotide. The second part of the procedure involved formation of binary complexes, followed by contact with dCTP and dATP, and washing with buffers that included either dCTP and dATP, or dATP alone. The increase in signal observed following contact with the combination of dCTP and dATP indicated that a ternary complex had formed, and that one of dCTP and dATP was the cognate nucleotide. The fact that a binding complex was maintained in the absence of dCTP, and in the presence of dATP indicated that dCTP was the non-cognate nucleotide and that dATP was the cognate nucleotide.

Figure 3B:
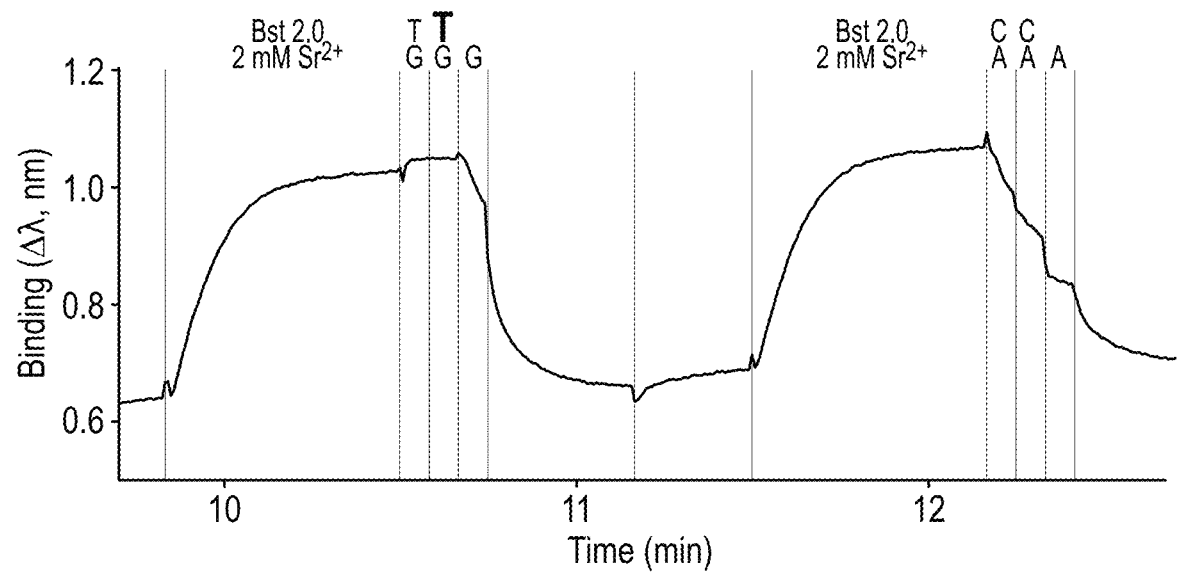

FIG. 3B shows results obtained in a system wherein the next correct nucleotide was dTTP. Binary complexes formed between the primed template nucleic acid and polymerase were contacted with a solution that included dTTP and dGTP, but did not include polymerase needed to maintain binary complexes in the absence of cognate nucleotide. Binding signal increased slightly upon contact with the solution that included dTTP and dGTP, thereby indicating that one of dTTP and dGTP was the cognate nucleotide. Binding signal was maintained substantially constant until dTTP was omitted from the wash buffer, at which point complexes dissociated. This indicated dTTP was the cognate nucleotide. In the second part of the procedure, wherein dCTP and dATP were tested for possible ternary complex formation, the binding signal decreased as soon as polymerase was withdrawn (i.e., contact with a solution including dCTP and dATP, but not including polymerase). Absent substantial maintenance of the binding signal, or a positive slope of a line joining the first and last measured data points of the interval corresponding to contact with dCTP and dATP (as would characterize a signal increase), it was confirmed that neither dCTP nor dATP was the cognate nucleotide.

Figure 3C:
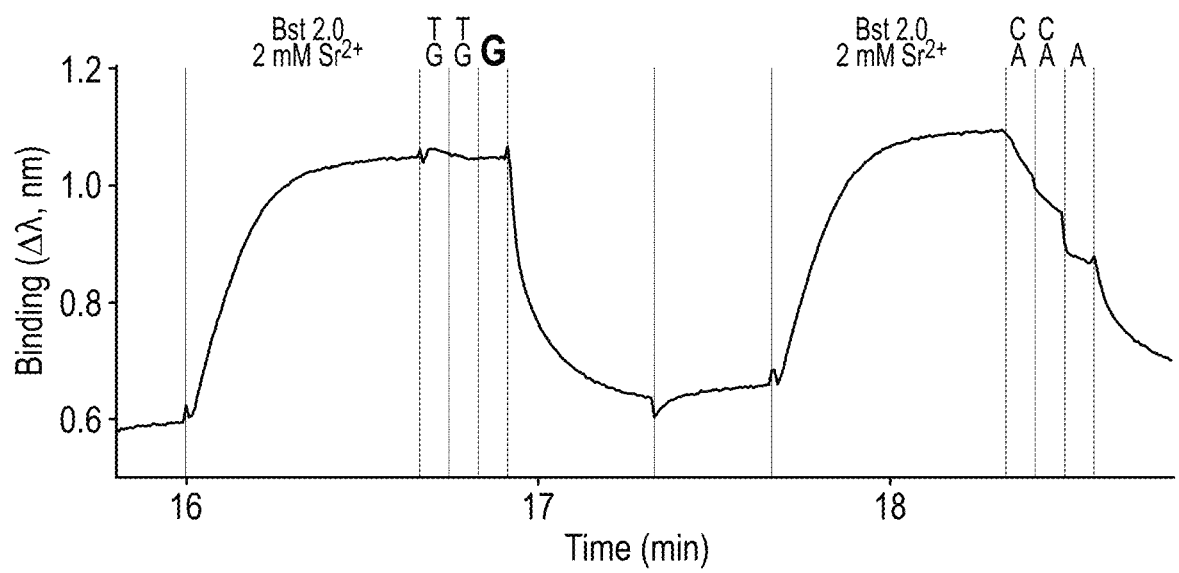

FIG. 3C shows results obtained in a system wherein the next correct nucleotide was dGTP. Binary complexes formed between the primed template nucleic acid and polymerase were contacted with a solution that included dTTP and dGTP, but did not include polymerase needed to maintain binary complexes in the absence of cognate nucleotide. Binding signal increased slightly upon contact with the solution that included dTTP and dGTP, thereby indicating that one of dTTP and dGTP was the cognate nucleotide. Binding signal was maintained substantially constant as long as dGTP was included in the wash buffer, thereby indicating that dGTP was the cognate nucleotide. In the second part of the procedure, wherein dCTP and dATP were tested for possible ternary complex formation, the binding signal decreased as soon as polymerase was withdrawn (i.e., contact with a solution including dCTP and dATP, but not including polymerase). Absent substantial maintenance of the binding signal, or a positive slope of a line joining the first and last measured data points of the interval corresponding to contact with dCTP and dATP, it was confirmed that neither dCTP nor dATP was the cognate nucleotide.

Figure 3D:
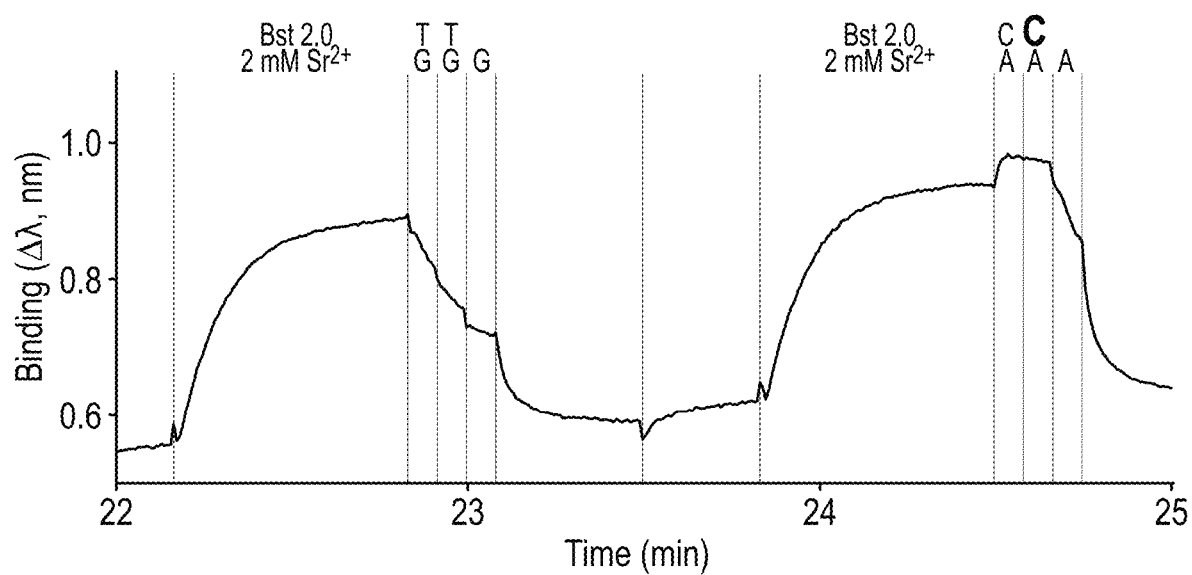

FIG. 3D shows results obtained in a system wherein the next correct nucleotide was dCTP. Binary complexes formed between the primed template nucleic acid and polymerase were contacted with a solution that included dTTP and dGTP, but did not include the polymerase needed to maintain binary complexes in the absence of cognate nucleotide. Binding signal decreased immediately and steadily after washes that included dTTP and dGTP, or dGTP alone. Absent substantial maintenance of the binding signal, or a positive slope of a line joining the first and last measured data points of the interval corresponding to contact with dTTP and dGTP, it was confirmed that neither dTTP nor dGTP was the cognate nucleotide. The second part of the procedure involved formation of binary complexes followed by contact with dCTP and dATP, at which point a positive slope was observed between the first and last points of the interval that involved contact with dCTP and dATP, thereby indicating that one of dCTP and dATP was the cognate nucleotide. Binding signal maintained substantially constant until dCTP was omitted from the wash buffer, at which point the binding signal decreased to indicate loss of ternary complexes. Accordingly, dCTP was the cognate nucleotide.

The following Examples illustrate examination steps that employed catalytic amounts of $Mg^{2+}$ ion in combination with a primer having a 3'-blocking group. The blocking group of the primer was removed after measuring binding of the primed template nucleic acid molecule to polymerase in the presence of each different native nucleotide. The measured binding was sufficient to identify which of the nucleotides represented the cognate nucleotide for a particular position. In the next step of the workflow, a reversible terminator nucleotide was incorporated without any intervening examination step (i.e., without intervening binding, detection or identification of any nucleotide). Notably, examination and incorporation steps were carried out using two different polymerase enzymes. Optionally, a single polymerase, such as the 3PDX polymerase disclosed in U.S. Pat. No. 8,703,461 for the purpose of interrogating nucleotide analogs and incorporating reversible terminator nucleotides, also may be used.

Example 3 describes examination of a primed template nucleic acid molecule, where the primer strand was blocked from extension at its 3'-end. The examination step (i.e., involving measuring interaction between the primed template nucleic acid molecule, the polymerase, and a test nucleotide) was conducted in the presence of a catalytic metal ion with the intention of enhancing discriminatory activity of the polymerase enzyme. Results presented below demonstrated efficient identification of the next correct nucleotide, and even the following next correct nucleotide.

Example 3

Examination of a Primed Template Nucleic Acid Molecule Having a 3'-Blocked Primer in the Presence of Catalytic Concentrations of Magnesium Ion A FORTEBIO® (Menlo Park, Calif.) Octet instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid molecule onto fiber optic tips functionalized with streptavidin (SA) according to standard procedures. A 3'-blocked primer was prepared by incorporating a cognate reversible terminator nucleotide that included a 3'-$ONH_2$ blocking group, using Therminator DNA polymerase (New England BioLabs Inc.; Ipswich, Mass.) according to the manufacturer's instructions. A description of the reversible terminator nucleotide can be found in U.S. Pat. No. 7,544,794, the disclosure of which is incorporated by reference. Binding of incoming nucleotides was investigated using 68 units/mL of Bsu DNA polymerase (New England BioLabs Inc.; Ipswich, Mass.) in a buffer that further included 30 mM Tris (pH 8.0), 220 mM KCl, 160 mM potassium glutamate, 1 mM $MgCl_2$, 0.01% Tween-20, and 1 mM β-mercaptoethanol. Ternary complex formation indicating cognate nucleotide binding was investigated by contacting the primed template nucleic acid molecule having the 3'-blocked primer with the Bsu DNA polymerase and one of four native dNTP nucleotides (dATP, dGTP, dCTP, and dTTP) for a period of 20 seconds. Each of the different nucleotides was used at a concentration of 100 μM during the examination procedure. Thereafter, biosensors were washed with a solution that included 20 mM EDTA for 25 seconds to chelate magnesium ions. The biosensors were then equilibrated with regeneration buffer that included 30 mM Tris (pH 8.0), 220 mM KCl, 160 mM potassium glutamate, 1 mM $MgCl_2$, 0.01% Tween-20, 1 mM β-mercaptoethanol. The same steps were repeated for the remaining nucleotides in sequence until collecting all binding curves for all four dNTPs. After completing examination of the different nucleotides, and acquiring measurement data for identifying the next correct nucleotide, the biosensor was transferred into a cleavage buffer solution (1 M sodium acetate pH 4.5 and 500 mM $NaNO_2$) for 60 seconds to remove the blocking group from the 3'-end of the primer. Biosensors were next equilibrated with a regeneration buffer (20 mM Tris pH 8.0, 10 mM KCl, and 0.01% Tween-20). Correct nucleotide was subsequently incorporated using the Therminator polymerase at a concentration of 30 units/mL in a buffer that included 20 mM Tris (pH 8.8), 10 mM ammonium sulfate, 10 mM KCl, 2 mM $MgCl_2$, 0.1% Triton-X-100, and all four reversible terminator nucleotides at a concentration of 100 μM each. All buffers were prepared with HPLC grade water and the incorporation buffer included HPLC water with 10 wt % OH—$NH_2$. The incorporation step was carried out for 60 seconds, after which time the bound polymerase was washed away from the biosensor with 20 mM EDTA for 5 seconds before commencing the next examination cycle, as described above.

Figure 4A:
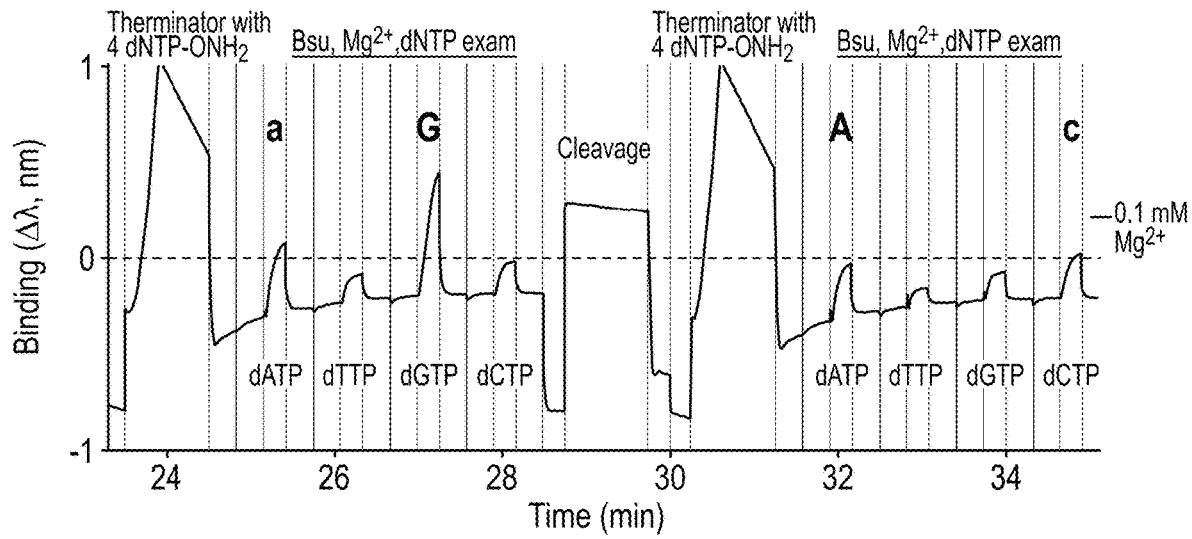
FIGS. 4A-4B are interferometry traces for the examination and incorporation cycles of the expected sequence (GAC) in example sequencing runs. Binding signals for all four dNTPs at the same position are illustrated in the presence of 0.1 mM $MgCl_2$ (FIG. 4A) or 1 mM $MgCl_2$ (FIG. 4B). All examination cycles were conducted after incorporating the correct 3'-blocked nucleotide, but before cleavage of the 3'-$ONH_2$ reversible terminator moiety to reveal an extendable 3'-OH group. Bases for the next correct incoming nucleotides (n+1) are highlighted using bold uppercase base identifiers for their respective positions in the sequence. Additionally, the second correct bases (n+2) are highlighted using bold lowercase base identifiers on their respective binding signal peaks. The order of nucleotide examination was: dATP, dTTP, dGTP, and dCTP.
Figure 4B:
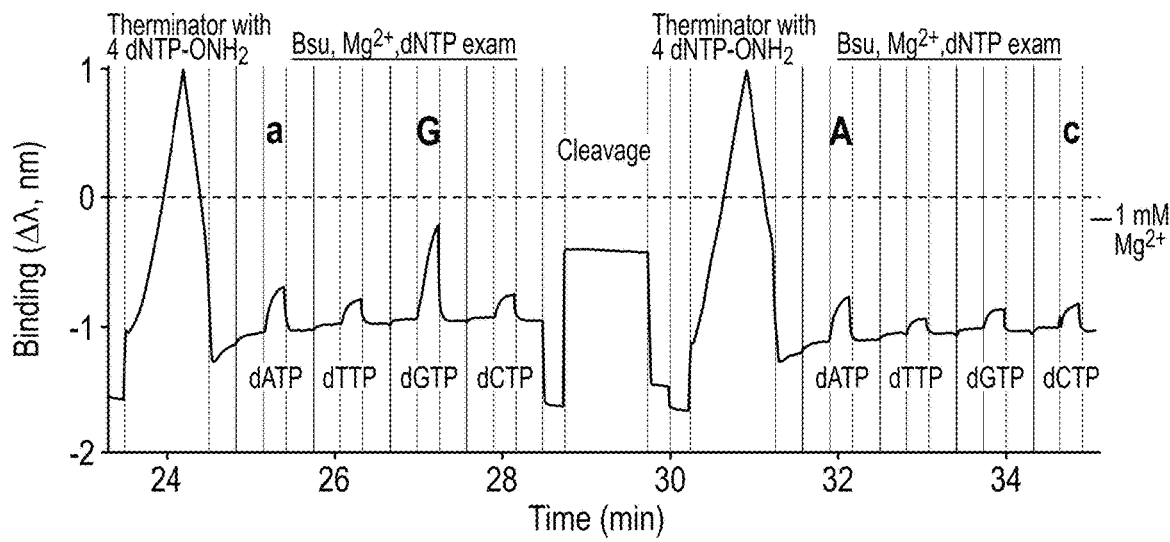

FIG. 4 shows the traces for all four nucleotides followed by the cleavage traces and incorporation traces, as discussed above. The expected base sequence in this example was GAC. As described above, a 3'-$ONH_2$ blocked primer was first formed by incorporating a reversible terminator using the Therminator polymerase. Next, for each cycle of examination the blocked primed template nucleic acid molecule was contacted with polymerase and a different nucleotide (dATP or dTTP or dGTP or dCTP) in the presence of catalytic magnesium ions for 20 seconds. High binding signals were observed if the examined nucleotide included the complementary base to the next base of the template strand. In addition to this peak, a second-high binding signal was also observed for the second correct complementary base to the second next base of the template strand. After all four nucleotides had been examined, a cleavage reaction removed the 3' blocking group from the primer. After removing the cleavage reagent with two wash steps (corresponding to the two steps with progressively reduced binding signals immediately following the cleavage step), a single incorporation reaction was carried out to add the next reversible terminator nucleotide. The procedure can be used for identifying the next correct nucleotide (next incoming nucleotide at the n+1 position), and can be repeated a plurality of times to determine the sequence of the template nucleic acid. As well, the results showed how the correct nucleotide at the n+2 position also could be determined. This observation was reproduced for all the positions in the sequence. Optionally, serial incorporation of two reversible terminators can be carried out without intervening examination steps using different types of nucleotides (i.e., other than reversible terminators) to speed the process of sequence determination.

The foregoing procedure employed a plurality of examination reactions to obtain the information needed for identifying a cognate nucleotide before conducting an incorporation reaction using reversible terminator nucleotides. Generally speaking, data processing for base calling need not be contemporaneous with the examination and incorporation reactions using this approach. Optionally, base calling algorithms can employ recorded measurement data acquired during the examination steps. Further, it is to be understood that while examination and incorporation steps in the illustrated protocol used two different enzymes to demonstrate procedural flexibility, these steps optionally can be carried out using the same polymerase enzyme. Still further, the reversibly blocked primer employed in the examination step permitted use of a catalytic metal ion during that step. Optionally, however, non-catalytic metal ions, or mixtures of non-catalytic and catalytic metal ions, can be substituted in place of the catalytic metal ions when using a primed template nucleic acid molecule having a 3'-blocked primer.

Example 4 describes a dissociation-based sequencing protocol, wherein an incorporation reaction that was conducted after a plurality of examination reactions facilitated rapid nucleotide identification. Interaction of a polymerase and a primed template nucleic acid molecule having a reversibly blocked primer (referred to herein as a "blocked primed template nucleic acid molecule") were measured or monitored continuously to document the binding reaction mechanism. Periodic (e.g., end-point) measurements may be simpler to execute, and can be used to obtain similarly good results. After measuring interaction of a polymerase with the blocked primed template nucleic acid molecule to determine whether or not a nucleotide under investigation was the cognate nucleotide for a particular position, the reversible terminator moiety of the blocked primed template nucleic acid molecule was removed before incorporating the next reversible terminator nucleotide. The primed template nucleic acid molecule having a free 3'-hydroxyl moiety never contacted any nucleotide other than those comprising reversible terminator moieties. As in the preceding Example, incorporation of reversible terminator nucleotides was performed using a polymerase different from the one used for examining transient binding of nucleotides (i.e., investigating ternary complex formation). However, as discussed above, a single polymerase enzyme may also be used to perform both of these functions in a simplified procedure.

Example 4

Dissociation-Based Sequencing-by-Binding Employing Examination of Reversibly Blocked Primers in the Presence of Catalytic Concentrations of Magnesium Ions A FORTEBIO® (Menlo Park, Calif.) Octet instrument employing biolayer interferometry to measure binding reactions at the surface of a fiber optic tip was used in a multiwell plate format to illustrate the sequencing technique. Template strands biotinylated at their 5'-ends were used to immobilize primed template nucleic acid molecule onto fiber optic tips functionalized with streptavidin (SA) according to standard procedures. A 3'-blocked primer was prepared by incorporating a cognate reversible terminator nucleotide that included a 3'-$ONH_2$ blocking group, using Therminator DNA polymerase (New England BioLabs Inc.; Ipswich, Mass.) according to the manufacturer's instructions. A description of the reversible terminator nucleotide can be found in U.S. Pat. No. 7,544,794, the disclosure of which is incorporated by reference. Binding of incoming nucleotides was investigated using either Bsu DNA polymerase or Bst 2.0 DNA polymerase, both of which were obtained from New England BioLabs Inc. (Ipswich, Mass.). The Bsu DNA polymerase was used at a concentration of 400 U/mL, while the Bst 2.0 DNA polymerase was used at a concentration of 600 U/mL, each in a buffer that further included 30 mM Tris (pH 8.0), 220 mM KCl, 160 mM potassium glutamate, 1 mM $MgCl_2$, 0.01% Tween-20, and 1 mM β-mercaptoethanol. Sensor tips having blocked primed template nucleic acid molecules immobilized thereon were initially contacted with polymerase in the absence of any nucleotide for a period of 20 seconds. Next, sensor tips were removed from the polymerase-containing solution and contacted for a period of 10 seconds with a solution that included the polymerase and a paired set of two nucleotides (e.g., dTTP and dATP), each of the nucleotides being present at a concentration of 100 μM. Cognate nucleotide corresponding to the next correct nucleotide participated in formation of a ternary complex during this step. Next, sensor tips were washed for 30 seconds with a solution that included 20 mM EDTA to chelate $Mg^{2+}$ ions and remove polymerase and nucleotide from the sensor tip. Next, sensor tips were removed from the EDTA-containing solution and contacted for a period of 10 seconds with a solution that included the polymerase and a second paired set of two nucleotides (e.g., dCTP and dGTP), each of the nucleotides being present at a concentration of 100 μM. Again, cognate nucleotide corresponding to the next correct nucleotide participated in formation of a ternary complex during this step. Next, sensor tips were washed for 30 seconds with a solution that included 20 mM EDTA to chelate $Mg^{2+}$ ions and remove polymerase and nucleotide from the sensor tip. At this point all binding results required for identifying the next correct nucleotide had been acquired, without performing any incorporation reaction. The biosensor was then transferred into a cleavage buffer solution (1 M sodium acetate (pH 5.5) and 500 mM $NaNO_2$) for 60 seconds to remove the blocking group from the 3'-end of the primer. Biosensors were next equilibrated with a regeneration buffer (20 mM Tris (pH 8.0), 10 mM KCl, and 0.01% Tween-20). Reversible terminator nucleotides corresponding to next correct bases were incorporated into the primer using the Therminator polymerase (New England BioLabs Inc.) at 30 units/mL in a buffer that included 20 mM Tris (pH 8.8), 10 mM $(NH_4)_2SO_4$, 10 mM KCl, 5 mM $MgCl_2$, and 0.1% Triton-X-100, and further included all four reversible terminators at 100 μM concentrations each. All buffers were prepared with HPLC grade water and the incorporation buffer included HPLC water with 1 wt % OH—$NH_2$. The incorporation step was allowed to proceed for 60 seconds. Polymerase was removed by washing with 20 mM EDTA for 30 seconds before the new cycles of polymerase binding were begun.

Figure 5A:
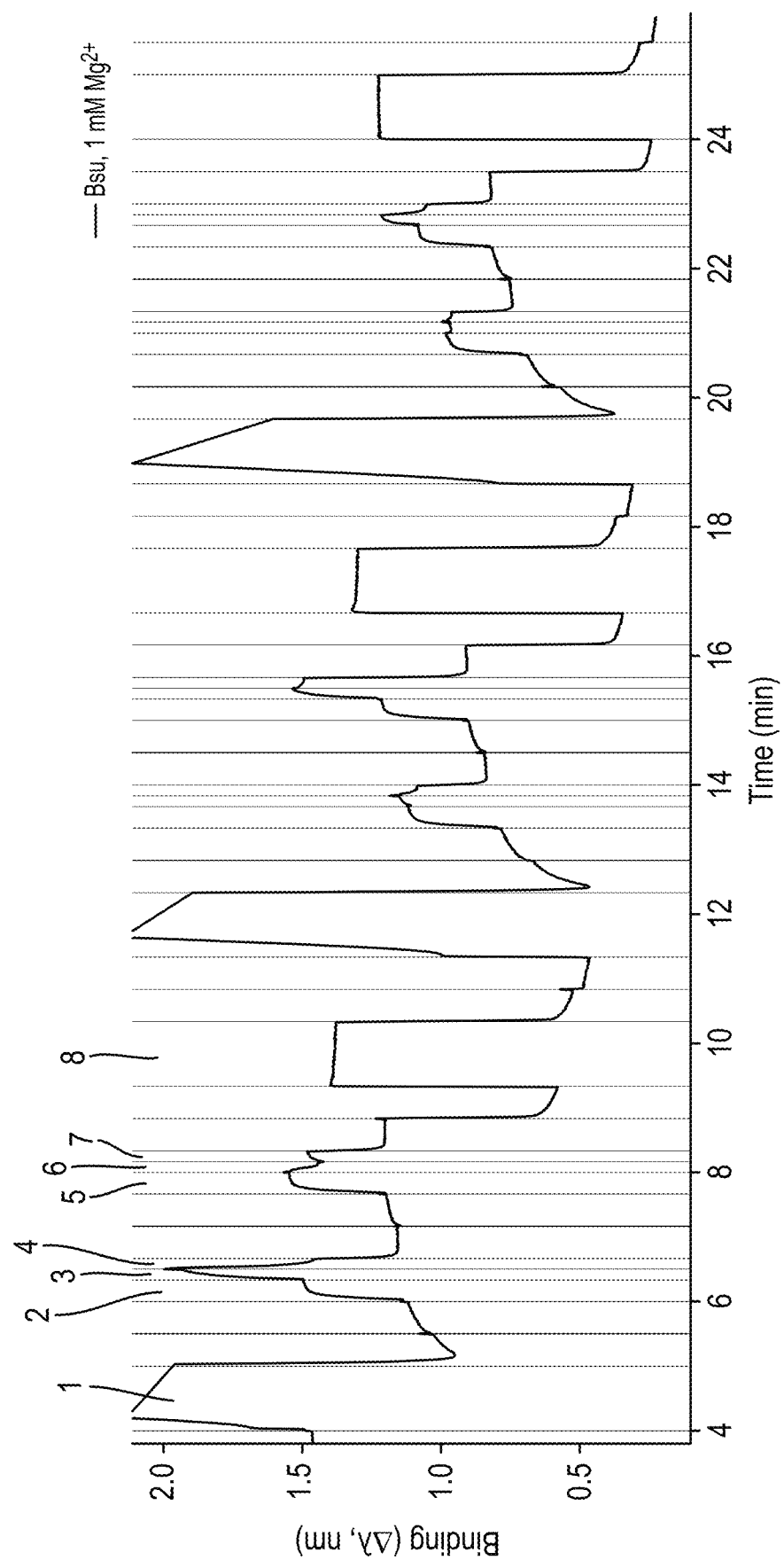
FIGS. 5A-5B are interferometry traces for the examination and incorporation cycles of an expected sequence (TGC), where binding signals for all four dNTPs are shown for a single interrogated position in the presence of 1 mM $MgCl_2$.

FIG. 5A illustrates three complete cycles of reversible terminator incorporation/examination/removal of the reversible terminator moiety, where Bsu DNA polymerase was used to conduct the examination steps. Numbers have been assigned to each step within the different cycles for convenience. Referring now to cycle 1 (representative of the entire procedure), step 1 corresponded to incorporation of a reversible terminator moiety into the primer. The very high signal observed in this step was not informative with respect to nucleotide identity. Steps 2 and 3 corresponded respectively to an EDTA wash step (to remove any bound polymerase), and a regenerating buffer wash step (to remove EDTA and adjust buffer conditions). Polymerase binding in the absence of nucleotide in step 4 increased the binding signal. The signal was further increased in step 5, after the blocked primed template nucleic acid contacted a reaction mixture that included dATP and dTTP in addition to the polymerase from step 4. The substantial increase in binding signal observed during step 5 reflected ternary complex formation, and indicated that one of dATP and dTTP was the cognate nucleotide for the position being interrogated. Washing with a solution that included, in addition to the polymerase of step 4, dATP but not dTTP led to a substantial reduction of the binding signal in step 6. This indicated that the ternary complex became unstable and was disrupted in the absence of dTTP. Accordingly, dTTP was identified as the next correct nucleotide. Steps 7 and 8 corresponded respectively to another EDTA wash step (to remove any bound polymerase) and another regenerating buffer wash step (to remove EDTA and adjust buffer conditions). In step 9, contacting the blocked primed template nucleic acid molecule with the same polymerase used in step 4, again in the absence of nucleotide, increased the binding signal. The binding signal did not substantially increase in step 10, after the blocked primed template nucleic acid molecule contacted a solution that included dGTP and dCTP in addition to the polymerase of step 4. The absence of a substantial increase in binding signal indicated that a ternary complex did not form. Accordingly, neither of dGTP and dCTP was the cognate nucleotide for that position. In step 11, washing with a solution that included the polymerase of step 4 and dGTP but not dCTP did not substantially change the binding signal, as expected (i.e., because neither dGTP nor dCTP was the cognate nucleotide for this position). Another EDTA wash in step 12 removed any bound polymerase, and a subsequent wash changed buffer conditions in step 13. Cleavage of the reversible terminator moiety in step 14 revealed a free 3'-OH group on the primer that was available to participate in phosphodiester bond formation. Two wash steps in steps 15 and 16 prepared the primed template nucleic acid molecule to receive the next reversible terminator nucleotide by an enzymatic incorporation reaction.

Figure 5B:
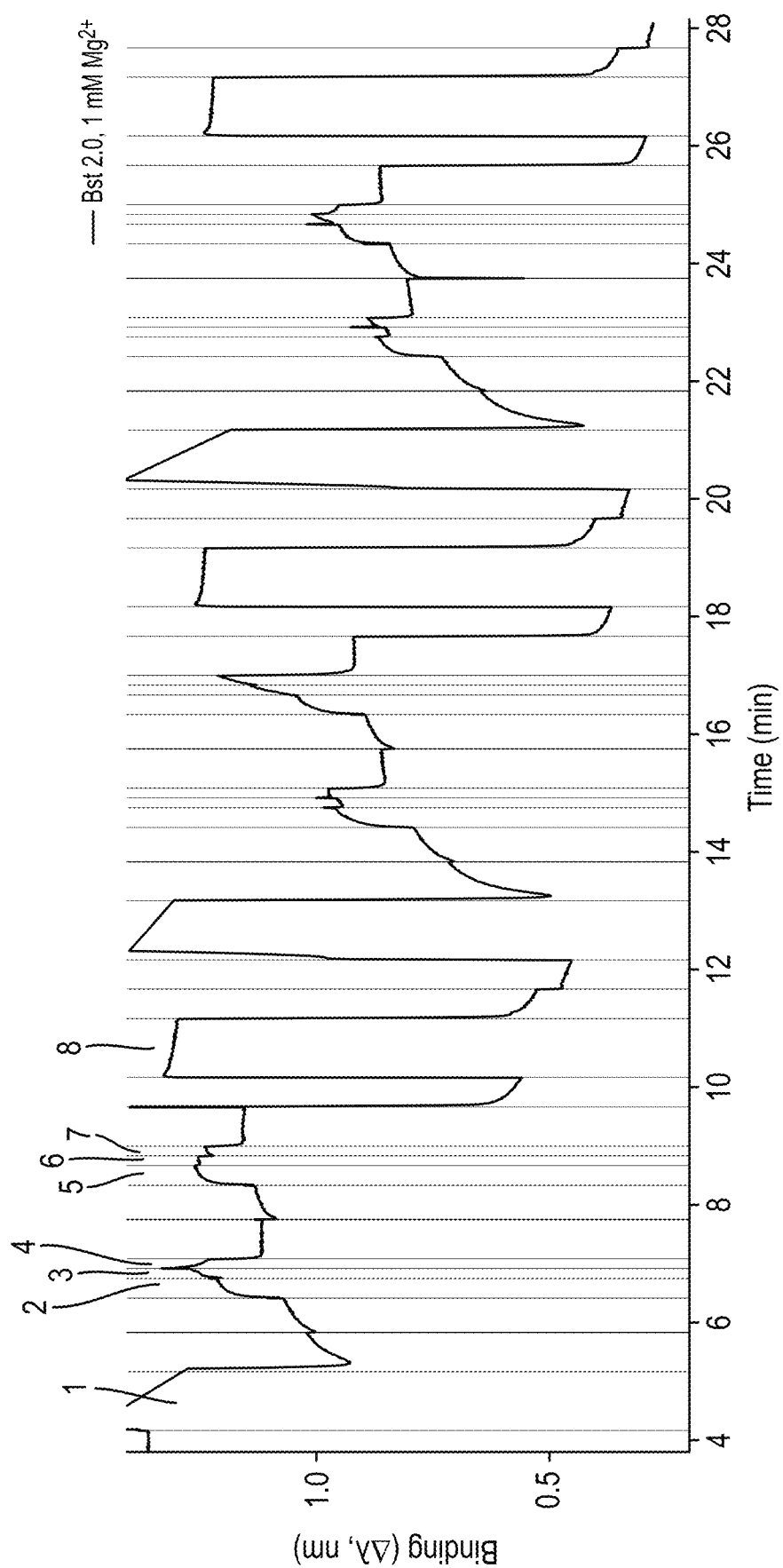

FIG. 5B illustrates three complete cycles of reversible terminator incorporation/examination/removal of the reversible terminator moiety, where Bst 2.0 DNA polymerase was used to conduct the examination steps. The results were consistent with those presented in FIG. 5A, that were obtained using a different DNA polymerase in the examination steps.

Disclosed above are materials, compositions, and components that can be used for, can be used in conjunction with, can be used in preparation for, or are products of the disclosed methods and compositions. It is to be understood that when combinations, subsets, interactions, groups, etc. of these materials are disclosed, and that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure, including steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein, and the material for which they are cited, are hereby specifically incorporated by reference in their entireties. All publications, patents, and patent applications mentioned in this specification are herein incorporated by reference to the same extent as if each individual publication, patent, or patent application was specifically and individually indicated to be incorporated by reference.

It is to be understood that the headings used herein are for organizational purposes only and are not meant to limit the description or claims.

A number of embodiments have been described. Nevertheless, it will be understood that various modifications may be made. Accordingly, other embodiments are within the scope of the claims.

What is claimed is:

1. A method for identifying a nucleotide of a nucleic acid, comprising:
    (a) providing a solid support that is attached to a primed template nucleic acid molecule, wherein the solid support is in contact with a first reaction mixture that comprises a polymerase and a plurality of different nucleotide types,
        wherein the primed template nucleic acid molecule, the polymerase and one of the plurality of different nucleotide types form a stabilized ternary complex on the solid support;
    (b) progressively removing nucleotide types of the plurality of different nucleotide types from contact with the primed template nucleic acid molecule on the solid support;
    (c) monitoring stability of the ternary complex on the solid support during the progressive removal of the nucleotide types, without incorporating any nucleotide into the primer; and
    (d) identifying the nucleotide that comprises the base complementary to the next base of the template strand using results from step (c).

2. The method of claim 1, wherein the progressively removing of step (b) comprises exchanging the first reaction mixture with a second reaction mixture that does not include a first nucleotide type of the plurality of different nucleotide types.

3. The method of claim 2, wherein the monitoring of step (c) comprises observing dissociation of the ternary complex in the second reaction mixture and step (d) comprises identifying the first nucleotide type as the nucleotide that comprises the base complementary to the next base of the template strand.

4. The method of claim 1, further comprising (e) incorporating a nucleotide into the primer of the primed template nucleic acid molecule, thereby forming an extended primed template nucleic acid molecule.

5. The method of claim 4, further comprising repeating steps (a) through (e) using the extended primed template nucleic acid molecule instead of the primed template nucleic acid molecule.

6. The method of claim 4, wherein the nucleotide that is incorporated into the primer of the extended primed template nucleic acid molecule comprises a reversible terminator moiety.

7. The method of claim 6, further comprising removing the reversible terminator moiety from the extended primed template nucleic acid molecule and repeating steps (a) through (e) using the extended primed template nucleic acid molecule instead of the primed template nucleic acid molecule.

8. The method of claim 4, wherein the nucleotide that is incorporated into the primer of the extended primed template nucleic acid molecule is a non-labeled nucleotide.

9. The method of claim 1, wherein the nucleotides in the plurality of different nucleotide types comprise exogenous labels.

10. The method of claim 9, wherein step (c) comprises detecting dissociation of the exogenous labels from the primed template nucleic acid molecule on the solid support.

11. The method of claim 9, wherein each type of nucleotide in the plurality of different nucleotide types is linked to a different type of label.

12. The method of claim 9, wherein the different types of nucleotides in the plurality of different nucleotide types are linked to the same type of label.

13. The method of claim 1, wherein the polymerase comprises an exogenous label and wherein step (c) comprises detecting the exogenous label.

14. The method of claim 13, wherein step (c) comprises detecting dissociation of the exogenous labels from the primed template nucleic acid molecule on the solid support.

15. The method of claim 1, wherein the first reaction mixture comprises cognates for four different base types in the template nucleic acid.

16. The method of claim 1, wherein the solid support is covalently attached to the primed template nucleic acid molecule.

* * * * *